(12) United States Patent
Khalaf et al.

(10) Patent No.: US 8,012,967 B2
(45) Date of Patent: Sep. 6, 2011

(54) MINOR GROOVE BINDERS

(75) Inventors: Abedawn Khalaf, Glasgow (GB); Colin Suckling, Glasgow (GB); Roger Waigh, Glasgow (GB)

(73) Assignee: University of Strathclyde, Glasgow (GB)

( * ) Notice: Subject to any disclaimer, the term of this patent is extended or adjusted under 35 U.S.C. 154(b) by 14 days.

(21) Appl. No.: 12/443,529

(22) PCT Filed: Sep. 28, 2007

(86) PCT No.: PCT/GB2007/003698
§ 371 (c)(1), (2), (4) Date: Aug. 13, 2009

(87) PCT Pub. No.: WO2008/038018
PCT Pub. Date: Apr. 3, 2008

(65) Prior Publication Data
US 2010/0016311 A1    Jan. 21, 2010

(30) Foreign Application Priority Data

Sep. 30, 2006 (GB) .................................. 0619325.4

(51) Int. Cl.
*A61K 31/5355* (2006.01)
*C07D 413/14* (2006.01)

(52) U.S. Cl. .................. 514/235.2; 514/235.5; 544/124; 544/128; 544/141

(58) Field of Classification Search .................. None
See application file for complete search history.

(56) References Cited

U.S. PATENT DOCUMENTS

| | | |
|---|---|---|
| 1,886,481 A | 11/1932 | Hartmann et al. |
| 4,912,199 A | 3/1990 | Lown et al. |
| 4,919,199 A | 4/1990 | Hahn |
| 5,273,991 A | 12/1993 | Lee et al. |
| 5,637,621 A | 6/1997 | Bolonick et al. |
| 5,670,534 A | 9/1997 | Animati et al. |
| 5,698,674 A | 12/1997 | Bruice et al. |
| 5,753,629 A | 5/1998 | Beria et al. |
| 5,767,142 A | 6/1998 | LaVoie et al. |
| 5,801,155 A | 9/1998 | Kutyavin et al. |
| 5,985,909 A | 11/1999 | Denny et al. |
| 6,008,247 A | 12/1999 | Boykin et al. |
| 6,060,608 A | 5/2000 | Boger |
| 6,084,102 A | 7/2000 | Kutyavin et al. |
| 6,090,947 A | 7/2000 | Dervan et al. |
| 6,127,554 A | 10/2000 | Boykin et al. |
| 6,143,901 A | 11/2000 | Dervan |
| 6,172,104 B1 | 1/2001 | Tidwell et al. |
| 6,221,589 B1 | 4/2001 | Lane et al. |
| 6,251,933 B1 | 6/2001 | Denny et al. |
| 6,326,395 B1 | 12/2001 | Tidwell et al. |
| 6,426,408 B1 | 7/2002 | Kutyavin et al. |
| 6,472,537 B1 | 10/2002 | Baird et al. |
| 6,506,906 B1 | 1/2003 | Dervan |
| 6,545,162 B1 | 4/2003 | Dervan et al. |
| 6,555,693 B2 | 4/2003 | Ge et al. |
| 6,562,806 B1 | 5/2003 | Thurston et al. |
| 6,589,971 B1 | 7/2003 | Neidle et al. |
| 6,608,192 B1 | 8/2003 | Thurston et al. |
| 6,613,787 B2 | 9/2003 | Wilson et al. |
| 6,635,417 B1 | 10/2003 | Dervan |
| 6,649,652 B2 | 11/2003 | Boykin et al. |
| 6,660,255 B1 | 12/2003 | Gottesfeld et al. |
| 6,660,742 B2 | 12/2003 | Lee |
| 6,693,189 B2 | 2/2004 | Holt et al. |
| 2002/0169296 A1 | 11/2002 | Laemmli et al. |
| 2003/0120069 A1 | 6/2003 | Thurston et al. |
| 2003/0187026 A1 | 10/2003 | Li et al. |
| 2003/0195196 A1 | 10/2003 | Thurston et al. |
| 2004/0092736 A1 | 5/2004 | Thurston et al. |

FOREIGN PATENT DOCUMENTS

| | | |
|---|---|---|
| DE | 2331444 A1 | 1/1975 |
| EP | 164593 A1 | 12/1985 |
| EP | 0343893 A1 | 11/1989 |
| EP | 1413582 A1 | 4/2004 |
| FR | 2656608 A1 | 7/1991 |
| GB | 1473704 | 5/1977 |
| JP | 11189594 | 7/1999 |
| JP | 2001181279 A | 7/2001 |
| JP | 2003089652 A | 3/2003 |
| WO | 9728123 A1 | 8/1997 |
| WO | 9730975 A2 | 8/1997 |
| WO | 9821202 A1 | 5/1998 |
| WO | 9831673 A1 | 7/1998 |

(Continued)

OTHER PUBLICATIONS

Golub et al. "Molecular Classification of Cancer: Class Discovery and Class Prediction by Gene Expression Monitoring." Science (1999), vol. 286, 521-537.*
Lala et al. "Role of nitric oxide in tumor progression: Lessons from experimental tumors." Cancer and Metastasis Reviews (1998), 17(1), 91-106.*
Johnson et al. "Relationships between drug activity in NCI preclinical in vitro and in vivo models and early clinical trials." British Journal of Cancer (2001), 84(10), 1424-1431.*
Sausville et al. "Contributions of Human Tumor Xenografts to Anticancer Drug Development." Cancer Res. 2006, 66(7), Apr. 1, 2006.*
"cancer." MedLine Plus. (2009). Accessed Mar. 17, 2009. <http://www.nlm.nih.gov/medlineplus/cancer.html>.*

(Continued)

*Primary Examiner* — Rebecca Anderson
*Assistant Examiner* — Alicia L Otton
(74) *Attorney, Agent, or Firm* — Caesar, Rivise, Bernstein, Cohen & Pokotilow, Ltd.

(57) ABSTRACT

There is provided compounds of formula (I), wherein $R^1$, $R^{11}$, $R^{12}$, $Q^a$, X, $Q^b$, $Q^c$, A and D have meanings given in the description, or a pharmaceutically acceptable salt or solvate thereof, which compound, salt or solvate binds to the minor groove of DNA.

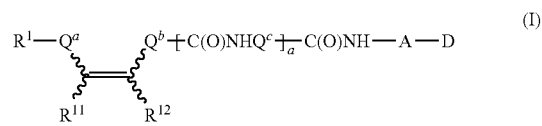

29 Claims, No Drawings

FOREIGN PATENT DOCUMENTS

| WO | 0119792 A1 | 3/2001 |
|---|---|---|
| WO | 0174898 A2 | 10/2001 |
| WO | 0183482 A1 | 11/2001 |
| WO | 0196313 A1 | 12/2001 |
| WO | 0200632 A1 | 1/2002 |
| WO | 0200650 A3 | 1/2002 |
| WO | 02095022 A2 | 11/2002 |
| WO | 02100832 A1 | 12/2002 |
| WO | 02101007 A2 | 12/2002 |
| WO | 03059881 A3 | 7/2003 |
| WO | WO 03/059881 * | 7/2003 |
| WO | 03070450 A1 | 8/2003 |
| WO | 03072058 A2 | 9/2003 |
| WO | 03078450 A2 | 9/2003 |
| WO | 2005012257 A1 | 2/2005 |

OTHER PUBLICATIONS

Human Immunodeficiency Virus I from Merck manual, pp. 1-16. Accessed Aug. 27, 2009.*
Respiratory Viruses Introduction from Merck manual, pp. 1-2. Accessed Aug. 27, 2009.*
Acute Viral Hepatitis from Merck manual, pp. 1-8. Accessed Aug. 27, 2009.*
Mosch B, Morawski M, Mittag A, Lenz D, Tarnok A, Arendt T, "Aneuploidy and DNA replication in the Normal Human Brain and Alzheimer's Disease," The Journal of Neuroscience, 2007, 27(26): 6859-6867.*
Dementia from Merck manual, pp. 1-17. Accessed Jul. 29, 2009.*
Mattson MP, "Pathways towards and away from Alzheimer's disease," Nature, Aug. 2004, 430: 631-639.*
Introduction to Cancer from Merck manual, p. 1. Accessed Mar. 5, 2008.*
Clinical Aspects of Cancer from Merck manual, pp. 1-4. Accessed Mar. 5, 2008.*
Auerbach R, Akhtar N, Lewis RL, Shinners BL, "Angiogenesis assays: Problems and pitfalls," Cancer and Metastasis Reviews, 2000, 19: 167-172.*
Gura T, "Systems for Identifying New Drugs Are Often Faulty," Science, 1997, 278: 1041-1042.*
Jain RK, "Barriers to Drug Delivery in Solid Tumors," Scientific American, 1994, 58-65.*
Tao et al. JACS , vol. 122, pp. 1602-1608, (2000).*
Steckelberg, James. MayoClinic. What's the difference between a bacterial infection and a viral infection? Accessed Oct. 22, 2010.*
Morissette et al. "High-throughput crystallization: polymorphs, salts, co-crystals and solvates of pharmaceutical solids." Advanced Drug Delivery Reviews 2004, 56, 275-300.*
Souillac, et al., Characterization of Delivery Systems, Differential Scanning Calorimetry, pp. 217-218 (in Encyclopedia of Controlled Drug Delivery, 1999, John Wiley & Sons, pp. 212-227).*
Vippagunta, Sudha R. "Crystalline Solids." Advanced Drug Delivery Reviews 48(2001): 3-26.*
Tao, et al., "Highly Cooperative DNA Dialkylation by the Homodimer of Imidazole-Pyrrole Diamide-CPI Conjugate with Vinyl Linker", J. Am. Chem. Soc., vol. 122, pp. 1602-1608 (2000).
International Search Report for PCT/GB2007/003698.
Abrescia, N.G.A., et al., J. Mol. Biol., 1999, 294, 657.
Anthony, N.G., et al., Bioorg. Med. Chem. Letters, 14, 1353-1356 (2004).
Bailly C., et al. Biochemistry 31, 8349 (1992).
Bando T., et al., Bioconjugate Chem. 17, 715-720 (2006).
Bando T., et al., Chem. & Biol. 10, 751-758 (2003).
Bando T., et al., Chem. Eur. J. 8, 4781-4790 (2002).
Bando T., et al., J. Am. Chem. Soc. 123, 5158-5159 (2001).
Bando T., et al., J. Am. Chem. Soc. 125, 3471-3485 (2003).
Bando T., et al., J. Am. Chem. Soc. 126, 3406-3407 (2004).
Bando T., et al., J. Am. Chem. Soc. 126. 8948-8955 (2004).
Bando T., et al., J. Am. Chem. Soc. 127, 13890-13895 (2005).
Dervan, Bioorg. Med. Chem. 9, 2215 (2001).
Drummond A.J., et al., Recent Res. Devel. Phytochem. 4, 143-152 (2000).
Dwyer T.J., et al., J. Am. Chem. Soc. 114(15), 5911 (1992).
Dyatkina N.B., et al., J. Med. Chem. 45, 805 (2002).
Fishleigh R.V., et al., J. Med. Chem. 43, 3257-3266 (2000).
Freydank, A.C., et al., Tetrahedron, 2002, 58, 1425-1432.
Geierstanger B.H., et al., Science 266, 646 (1994).
Gemmell C.G., et al., J. Med. Microbiol. 46, 208-213 (1997).
Gerlier D., et al., J. Immunol. Methods 94, 57-63 (1986).
Hamdan I.I., et al., Nucleic Acid Res. 26, 3053-3058 (1998).
Hampshire A.J., et al., Bioorg. Med. Chem. Letters, 16, 3469-3474 (2006).
Inami, K., et al., Bull. Chem. Soc. Jpn., 1985, 58, 352.
James P.L./, et al., Nucleic Acids Research, 32, 3410-3417 (2004).
Kaizerman, J.A, et al., J. Med. Chem. 2003, 46, 3914.
Khalaf A., et al., Tetrahedron 56, 5225 (2000).
Khalaf A.I., et al., J. Med. Chem. 47, 2133-2156 (2004).
Lee M., et al., Biochemistry 32, 4237 (1993).
Mrksich M., et al., Proc. Natl. Acad. Sci. USA 89, 7586 (1992).
Neamati N., et al., Molecular Pharmacology 54, 280 (1998).
Plouvier B., et al., Anti-Cancer Drug Design 10, 155 (1995).
Plouvier B., et al., Bioconjugate Chem. 5, 475 (1994).
Rao K.E., et al., Anti-Cancer Drug Design 5, 3 (1990).
Reddy et al., Pharmacology & Therapeutics 84, 1 (1999).
Ryabinin V.A., et al., Bioorg. Med. Chem. 8, 985 (2000).
Sharma S.K., et al., Bioorg. Med. Chem. Lett. 11, 769 (2001).
Sharma S.K., et al., Bioorg. Med. Chem. Lett. 12, 2007 (2002).
Sondhi et al., Curr. Med. Chem. 4, 313 (1997).
Suckling C.J., Expert Opin. Ther. Patents, 14(12) (2004).
Suckling C.J., et al., Tetrahedron, 2000, 56, 5225.
Vasdyutina, V.L., et al., Mol. Biol. 34, 356 (2000).
Wasserman, H.H., et al., Tetrahedron, 2003, 59, 6771-6784.
Wemmer, Biopolymers 52, 197 (2001).
Yamamoto Y., et al., Tet. Lett. 37(43), 7801-7804 (1996).
Yang Y., et al., biochem. Biophys. Res. Commun. 222, 764 (1996).
Zhao R., et al., Bioorg. Med. Chem. Lett. 6(18), 2169 (1996).
Corona Viruses and Severe Acute Respiratory Syndrome (SARS), Merck manual, p. 1, 2009.
Bloomfield et al., Nucleic Acids: Structure, Properties and Functions, pp. 176-180 and 561-564 (2000).
Bugreev et al., Antisense & Nuclear Acid Drug Development, 11:137-147 (2001).
Bunkenborg et al., Bioconjugate Chem., vol. 13, pp. 927-936 (2002).
Burli et al., Bioinorganic and Medicinal Chemistry Letters, 12:2591-2594 (2002).
Dickinson et al., Proc. Natl. Acad. Sci. USA, vol. 95, pp. 12890-12895 (1998).
Ding et al., Acta Chemica Scandinavica, vol. 48, pp. 498-505 (1994).
Frau et al., Nucleosides, Nucleotides and Nucleic Acids, vol. 20(1&2), pp. 145-156 (2001).
Grehn et al., J. Med. Chem., vol. 26, pp. 1042-1049 (1983).
Han et al., Current Medicinal Chemistry, vol. 8, pp. 551-581 (2001).
Rao et al., J. Org. Chem., vol. 55, pp. 728-737 (1990).
Sharma et al., Tetrahedron, vol. 58:3417-3421 (2002).
Sharma et al., J. Org. Chem., vol. 65, pp. 1102-1107 (2000).
Trauger et al., J. Am. Chem. Soc., vol. 120, pp. 3534-3535 (1998).
Turchin et al., Soviet J. Biorg. Chem., vol. 4, pp. 780-791 (1978).
Wurtz et al., Biochemistry, vol. 41, pp. 7604-7609 (2002).
Xie et al., J. Med. Chem., 39:1049:1055 (1996).
Zhou et al., Bioinorganic and Medicinal Chemistry Letters, 7(19):2455-2456, (1997).

* cited by examiner

MINOR GROOVE BINDERS

FIELD OF THE INVENTION

This invention relates to synthetic compounds that have affinity for nucleic acids, and in particular to compounds that bind to the minor groove of DNA.

BACKGROUND

The listing or discussion of a prior-published document in this specification should not necessarily be taken as an acknowledgement that the document is part of the state of the art or is common general knowledge.

Because of its fundamental role in molecular biological processes, DNA represents an important target for drug action. Compounds that can recognise defined sequences of DNA have a wide variety of potential uses, such as the modulation of gene expression.

The outer surface of double-helical DNA has two channels, namely the major and minor grooves. Both of these grooves contain chemical information by way of arrangements of hydrogen-bond donors and acceptors, electrostatic charges, dipoles, hydrophobic regions and so on.

The major groove contains approximately twice the information content of the minor groove in terms of the number of potential hydrogen-bonding contacts. In view of this, the major groove is the preferred recognition site for cellular proteins such as control proteins, promoters and repressors.

In contrast, the minor groove is normally (with a few exceptions) relatively unoccupied. The vulnerability of the minor groove makes it a particularly useful target for compounds that bind to DNA. Indeed, perhaps for this very reason, the minor groove is the binding site for certain naturally occurring antibiotics (such as netropsin and distamycin).

Netropsin and distamycin are oligopeptides based on pyrrole amino acid monomers. These compounds both bind to DNA with dissociation constants in the order of $10^{-5}$ M. They also show a preference for AT-rich regions of DNA. Although they have intrinsic biological activity, netropsin and distamycin also have many limitations including toxicity, moderate affinity and limited selectivity. A number of workers have therefore prepared synthetic analogues of netropsin and distamycin, with a view to overcoming these disadvantages. Many of these compounds are reviewed by Sondhi et al (*Curr. Med. Chem.* 4, 313 (1997)), Reddy et al. (*Pharmacology & Therapeutics* 84, 1 (1999)), Wemmer (*Biopolymers* 52, 197 (2001)) and Dervan (*Bioorg. Med. Chem.* 9, 2215 (2001)).

Compounds designed to bind to DNA regions containing GC base pairs are described in, for example: *Anti-Cancer Drug Design* 5, 3 (1990); *Proc. Natl. Acad. Sci. USA* 89, 7586 (1992); *Biochemistry* 32, 4237 (1993); *Science* 266, 647 (1994); *Anti-Cancer Drug Design* 10, 155 (1995); *Bioorg. Med. Chem.* 8, 985 (2000); and *Mol. Biol.* 34, 357 (2000). Various other netropsin and distamycin analogues are described in: *J. Am. Chem. Soc.* 114(15), 5911 (1992); *Biochemistry* 31, 8349 (1992); *Bioconjugate Chem.* 5, 475 (1994); *Biochem. Biophys. Res. Commun.* 222, 764 (1996); *J. Med. Chem.* 43, 3257 (2000); and *Tetrahedron* 56, 5225 (2000). Further, the use of certain netropsin and distamycin analogues as antimicrobial, antiviral and/or antitumor agents is described in *Molecular Pharmacology* 54, 280 (1998), *Bioorg. Med. Chem. Lett.* 6(18), 2169 (1996), *J. Med. Chem.* 45, 805 (2002), *Bioorg. Med. Chem. Lett.* 12, 2007 (2002), international patent applications WO 97/28123, WO 98/21202, WO 01/74898 and WO 02/00650, as well as in U.S. Pat. Nos. 4,912,199, 5,273,991, 5,637,621, 5,698,674 and 5,753,629. Methods of synthesising analogues of netropsin and distamycin are described in U.S. Pat. No. 6,090,947.

Cellular uptake of distamycin analogues is described in *Bioorg. Med. Chem. Lett.* 11, 769 (2001).

Further compounds designed to bind to DNA are described in U.S. Pat. No. 6,143,901, which discloses oligomers of between 6 and 30 heterocyclic groups, in which the group linking the heterocycles may be methyleneamino, amido, thioamido, iminydyl or ethenylene. Amido (and its heteroanalogues) is described as the preferred linking group. There is no preference given in U.S. Pat. No. 6,143,901 in relation to the number or location of ethenylene linking groups, should such groups be present. Moreover, there is no suggestion that ethenylene-containing compounds may have any advantages over compounds containing other linkers (e.g. amido).

Analogues of distamycin are described in *Tet. Lett.* 37(43), 7801-7804 (1996), wherein an amide group linking two pyrroles of an oligopyrrole compound is replaced with either a diketo or alkenylene linker. The resulting compounds are described as having significantly lower binding affinity for DNA compared to the analogous amido-linked compounds.

Minor groove binding compounds comprising an acrylamide-type linker between the 2-position of a pyrrole group and a terminal basic group are described in *J. Am. Chem. Soc.* 122, 1602-1608 (2000), ibid. 123, 5158-5159 (2001), ibid. 125, 3471-3485 (2003), ibid. 126, 3406-3407 (2004), *Chem. Eur. J.* 8, 4781-4790 (2002), *Chem. & Biol.* 10, 751-758 (2003) and *Bioconjugate Chem.* 17, 715-720 (2006).

Further minor groove binding compounds comprising an acrylamide-type linker between the 3-position of a pyrrole group and a terminal aromatic group are described in *J. Med. Chem.* 47, 2133-2156 (2004).

None of the above-mentioned documents disclose or suggest compounds having affinity for DNA, which compounds comprise oligomers of cyclic groups in which an alkenylene moiety directly connects a cyclic group at the "amino" terminus to the adjacent cyclic group and at least one of the cyclic groups connected via the alkenylene moiety is other than a pyrrole (or 5-membered heterocycle).

DESCRIPTION OF THE INVENTION

According to the invention, there are provided compounds of formula I,

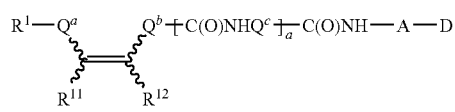

wherein
the wavy lines indicate optional cis- or trans-stereochemistry;
$R^1$ represents
  H,
  $R^{1a}C(O)$—NH—,
  $NO_2$ or
  —$N(R^{1a})R^{2b}$;
$R^{1a}$ represents
  aryl (which latter group is optionally substituted by one or more substituents selected from OH, halo, cyano, nitro, $N(R^{2a})R^{2b}$, $C_{1-4}$ alkyl and $C_{1-4}$ alkoxy),
  aromatic or part-aromatic $C_{13-14}$ tricyclic carbocyclyl (which latter group is optionally substituted by one or more substituents selected from OH, halo, cyano, nitro, $N(R^{2a})R^{2b}$, $C_{1-4}$ alkyl and $C_{1-4}$ alkoxy, and which latter group, if part-aromatic, is optionally substituted in the non-aromatic part by one or two oxo groups) or $C_{1-12}$ alkyl (which latter group is optionally substituted and/or terminated by one or more substituents selected from halo and aryl (which latter group is optionally substituted by one or more substituents selected from OH, halo, cyano, nitro, $N(R^{2a})R^{2b}$, $C_{1-4}$ alkyl and $C_{1-4}$ alkoxy));

a represents 1, 2, 3 or 4;

A represents $C_{2-6}$ alkylene or $A^1$-C(O)N(H)-$A^2$, wherein $A^2$ is attached to the group D;

$A^1$ represents $C_{1-4}$ alkylene;

$A^2$ represents $C_{2-5}$ alkylene;

D represents $Het^1$, —$N(R^{3a})R^{3b}$, —$C(=NR^{3c})N(R^{3d})R^{3e}$ or —$N(R^{3f})C(=NR^{3g})N(H)R^{3h}$;

$Het^1$ represents a four- to twelve-membered heterocyclic group containing at least one N atom and optionally one or more heteroatoms selected from N, O and S, which heterocyclic groups are optionally substituted by one or more substituents selected from =O, OH, halo, cyano, nitro, $N(R^{2a})R^{2b}$, $C_{1-4}$ alkyl and $C_{1-4}$ alkoxy;

$R^{3a}$ and $R^{3b}$ independently represent H, $C_{1-6}$ alkyl or $Het^2$;

$R^{3c}$ to $R^{3h}$ independently represent H or $C_{1-6}$ alkyl;

$Het^2$ independently represents a four- to twelve-membered heterocyclic group containing one or more heteroatoms selected from N, O and S, which heterocyclic group is optionally substituted by one or more substituents selected from =O, OH, halo, cyano, nitro, $N(R^{2a})R^{2b}$, $C_{1-4}$ alkyl and $C_{1-4}$ alkoxy;

each $Q^a$ to $Q^c$ independently represents, at each occurrence when used herein, naphthyl (optionally substituted by one or more substituents selected from OH, halo, cyano, nitro, $N(R^{2a})R^{2b}$, $C_{1-4}$ alkyl and $C_{1-4}$ alkoxy), $Het^3$, or a structural fragment of formula Ia, Ib, Ic, Id, Ie or If,

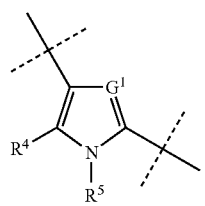

Ia

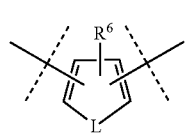

Ib

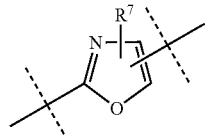

Ic

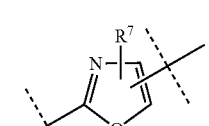

Id

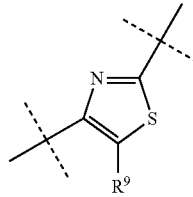

Ie

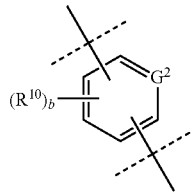

If wherein the dashed lines indicate the positions of attachment of the fragments;

$R^4$ represents H or $C_{1-6}$ alkyl;

$R^5$ represents $C_{1-12}$ alkyl;

$R^6$, $R^7$, $R^8$ and $R^9$ independently represent H or $C_{1-12}$ alkyl;

$R^{10}$ represents, independently at each occurrence, OH, halo, cyano, nitro, $N(R^{2a})R^{2b}$, $C_{1-4}$ alkyl, —S—$C_{1-4}$ alkyl and $C_{1-4}$ alkoxy;

b represents 0, 1, 2 or 3;

$G^1$ and $G^2$ independently represent CH or N, or $G^2$ alternatively represents C—$R^{10}$;

L represents O or S;

$Het^3$ represents a nine- or ten-membered, bicyclic heterocyclic group containing one or more heteroatoms selected from N, O and S, which group is optionally substituted by one or more substituents selected from =O, halo, cyano, nitro, $N(R^{2a})R^{2b}$, $Het^a$, $C_{1-4}$ alkyl and $OR^a$;

$R^a$ represents H, $C_{1-4}$ alkyl, aryl (which latter group is optionally substituted by one or more substituents selected from OH, halo, cyano, nitro, $N(R^{2a})R^{2b}$, $C_{1-4}$ alkyl and $C_{1-4}$ alkoxy) or $Het^b$;

$Het^a$ and $Het^b$ independently represent four- to twelve-membered heterocyclic groups containing one or more heteroatoms selected from N, O and S, which heterocyclic groups are optionally substituted by one or more substituents selected from =O, OH, halo, cyano, nitro, $N(R^{2a})R^{2b}$, $C_{1-4}$ alkyl and $C_{1-4}$ alkoxy;

$R^{11}$ and $R^{12}$ independently represent, at each occurrence when used herein, H, $C_{1-6}$ alkyl or aryl (which latter group is optionally substituted by one or more substituents selected from OH, halo, cyano, nitro, $N(R^{2a})R^{2b}$, $C_{1-4}$ alkyl and $C_{1-4}$ alkoxy);

$R^{2a}$ and $R^{2b}$ independently represent, at each occurrence when used herein, H or $C_{1-4}$ alkyl, or $R^{2a}$ represents —C(O)$R^{13}$;

$R^{13}$ represents H or $C_{1-4}$ alkyl; and unless otherwise specified alkyl, alkylene, alkenylene, cycloalkylene, phenylene and naphthylene groups, as well as the alkyl part of alkoxy groups, may be substituted by one or more halo atoms;

or a pharmaceutically acceptable derivative thereof, provided that the compound contains at least one $Q^a$ or $Q^b$ group that is other than a structural fragment of formula Ia in which $G^1$ represents CH, which compounds are referred to hereinafter as "the compounds of the invention".

Unless otherwise specified, alkyl groups and alkoxy groups as defined herein may be straight-chain or, when there is a sufficient number (i.e. a minimum of three) of carbon atoms, be branched-chain and/or cyclic. Further, when there is a sufficient number (i.e. a minimum of four) of carbon atoms, such alkyl and alkoxy groups may also be part cyclic/acyclic. Such alkyl and alkoxy groups may also be saturated or, when there is a sufficient number (i.e. a minimum of two) of carbon atoms, be unsaturated and/or interrupted by one or more oxygen and/or sulfur atoms. Unless otherwise specified, alkyl and alkoxy groups may also be substituted by one or more halo, and especially fluoro, atoms.

Unless otherwise specified, alkylene groups as defined herein may be straight-chain or, when there is a sufficient number (i.e. a minimum of two) of carbon atoms, be branched-chain. Such alkylene chains may also be saturated or, when there is a sufficient number (i.e. a minimum of two) of carbon atoms, be unsaturated and/or interrupted by one or more oxygen and/or sulfur atoms. Unless otherwise specified, alkylene groups may also be substituted by one or more halo atoms.

The term "aryl", when used herein, includes $C_{6-10}$ aryl groups such as phenyl, naphthyl and the like. When substituted, aryl groups are preferably substituted by between one and three substituents.

When used herein, the term "heterocyclic group" includes 4- to 12-membered (e.g. 5- to 10-membered) heterocyclic groups containing one or more heteroatoms selected from N, O and S. The term therefore includes such groups that are mono- or bicyclic, and which may be saturated, part-unsaturated, aromatic or, where appropriate, part-aromatic. Preferred heterocyclic groups include aromatic or part-aromatic groups such as pyrrolyl, imidazolyl, thiazolyl, oxazolyl, benzoxazolyl, furanyl, thienyl, pyridyl and coumarinyl. Particularly preferred heterocyclic groups include pyrrolyl, imidazolyl, thiazolyl and oxazolyl.

By "substituted in the heterocyclic part", we mean that each of the essential branched, cyclic or part cyclic $C_{3-5}$ alkyl groups is a direct substituent on the heterocyclic ring (whether attached to the ring via a heteroatom or otherwise) of each heterocyclic monomer bearing such a group.

The term "aromatic or part-aromatic $C_{13-14}$ tricyclic carbocyclyl", when used herein includes fluorenyl, anthracenyl, 9,10-dihydroanthracenyl, phenanthrenyl, 9,10-dihydrophenanthrenyl and the like.

The term "halo", when used herein, includes fluoro, chloro, bromo and iodo.

Het ($Het^1$ to $Het^3$, $Het^a$ and $Het^b$) groups that may be mentioned include those containing 1 to 4 heteroatoms (selected from the group oxygen, nitrogen and/or sulfur) and in which the total number of atoms in the ring system are between five and twelve. Het ($Het^1$ to $Het^3$, $Het^a$ and $Het^b$) groups may be fully saturated, partly unsaturated, wholly aromatic, partly aromatic and/or bicyclic in character. Heterocyclic groups that may be mentioned include 1-azabicyclo[2.2.2]octanyl, benzimidazolyl, benzo[c]isoxazolidinyl, benzisoxazolyl, benzodioxanyl, benzodioxepanyl, benzodioxolyl, benzofuranyl, benzofurazanyl, benzomorpholinyl, 2,1,3-benzoxadiazolyl, benzoxazolidinyl, benzoxazolyl, benzopyrazolyl, benzo[e]pyrimidine, 2,1,3-benzothiadiazolyl, benzothiazolyl, benzothienyl, benzothiophenyl, benzotriazolyl, benzoxazolyl, chromanyl, chromenyl, cinnolinyl, coumarinyl, 2,3-dihydrobenzimidazolyl, 2,3-dihydrobenzo[b]furanyl, 1,3-dihydrobenzo[c]-furanyl, 1,3-dihydro-2,1-benzisoxazolyl 2,3-dihydropyrrolo[2,3-b]pyridinyl, dioxanyl, furanyl, hexahydropyrimidinyl, hydantoinyl, imidazolyl, imidazo[1,2-a]pyridinyl, imidazo[2,3-b]thiazolyl, indolyl, isoquinolinyl, isoxazolidinyl, isoxazolyl, maleimido, morpholinyl, oxadiazolyl, 1,2- or 1,3-oxazinanyl, oxazolyl, phthalazinyl, piperazinyl, piperidinyl, purinyl, pyranyl, pyrazinyl, pyrazolyl, pyridinyl, pyrimidinyl, pyrrolidinonyl, pyrrolidinyl, pyrrolinyl, pyrrolo[2,3-b]pyridinyl, pyrrolo[5,1-b]pyridinyl, pyrrolo[2,3-c]pyridinyl, pyrrolyl, quinazolinyl, quinolinyl, sulfolanyl, 3-sulfolenyl, 4,5,6,7-tetrahydrobenzimidazolyl, 4,5,6,7-tetrahydrobenzopyrazolyl, 5,6,7,8-tetrahydrobenzo[e]-pyrimidine, tetrahydrofuranyl, tetrahydropyranyl, 3,4,5,6-tetrahydropyridinyl, 1,2,3,4-tetrahydropyrimidinyl, 3,4,5,6-tetrahydropyrimidinyl, thiadiazolyl, thiazolidinyl, thiazolyl, thienyl, thieno[5,1-c]pyridinyl, thiochromanyl, triazolyl, 1,3,4-triazolo[2,3-b]pyrimidinyl, xanthenyl and the like.

Values of $Het^1$ that may be mentioned include pyrrolodin-1-yl or, particularly, morpholin-4-yl.

Values of $Het^3$ that may be mentioned include isoquinolinyl or, particularly, quinolinyl (e.g. when $Q^a$ represents $Het^3$, then values of $Het^3$ that may be mentioned include quinolin-2-yl or quinolin-3-yl, wherein the numbering of the position of the attachment is determined relative to the position of attachment to —C($R^{11}$)).

Values of $Het^b$ that may be mentioned include benzotriazolyl (e.g. benzotriazol-1-yl).

Pharmaceutically acceptable derivatives include salts and solvates. Salts which may be mentioned include acid addition salts.

Compounds of formula I may exhibit tautomerism. All tautomeric forms and mixtures thereof are included within the scope of the invention.

Compounds of formula I may also contain one or more asymmetric carbon atoms and may therefore exhibit optical and/or diastereoisomerism. Diastereoisomers may be separated using conventional techniques, e.g. chromatography or fractional crystallisation. The various stereoisomers may be isolated by separation of a racemic or other mixture of the compounds using conventional, e.g. fractional crystallisation or HPLC, techniques. Alternatively the desired optical isomers may be made by reaction of the appropriate optically active starting materials under conditions which will not cause racemisation or epimerisation, or by derivatisation, for example with a homochiral acid followed by separation of the diastereomeric esters by conventional means (e.g. HPLC, chromatography over silica). All stereoisomers are included within the scope of the invention.

The compounds of the invention may be provided in a form rendering them bioavailable. When used herein, the term "bioavailable" includes compounds that, following administration, are in a form in which they can interact with a biological system, thereby providing a measurable therapeutic response. The term may thus be understood to include compounds that are provided to DNA in a form and/or level that is sufficient to provide a measurable desired or required therapeutic response.

Bioavailability of a compound may be predicted by a number of means known to those skilled in the art, including a measurement of a partition coefficient of the compound between water (for example at a pH of between 5 and 9) and an organic, water-immiscible solvent (e.g. octanol), which measurement can be used to predict the behaviour in body tissues of the compound in question (for a discussion of which see *J. Med. Chem.* 43, 3257-3266 (2000)).

Bioavailability may be achieved by providing compounds of the invention in a form (e.g. a pharmaceutical formulation) in which they are presented to DNA at an appropriate concentration to provide a measurable therapeutic response. Bioavailability may alternatively be achieved by changing the physicochemical properties of the active species, for example by improving water solubility by using techniques known to those skilled in the art (e.g. by the introduction of additional basic groups, such as described in *J. Med. Chem.* 43, 3257-3266 (2000)).

The compounds of the invention may have a high affinity for at least one DNA sequence. When used herein, the term "high affinity for at least one DNA sequence" includes compounds that, when bound to a minor groove of at least one DNA oligomer or polymer, have a dissociation constant of less than $10^{-5}$ M, preferably less than $10^{-6}$ M (such as $10^{-7}$ M) and particularly less than $10^{-8}$ M. In this respect, dissociation constants may be measured under conditions known to those skilled in the art, for example in water at room temperature (e.g. at or around 20° C.) in the presence of a buffer (e.g. a buffer that stabilises the pH at 7.5, such as a borate (e.g. at 0.02 M) or Tris/HCl (e.g. at 0.01 M) buffer) and at a DNA concentration of between 10 and 30 μM (e.g. 20 μM). Alternatively, dissociation constants may be estimated by a comparison of the binding affinity of a compound to a set DNA sequence with the binding affinity of a well-known compound (e.g. distamycin) to that same sequence.

Unless otherwise specified, the term "DNA" refers to double-stranded DNA. Further, when used herein, the term "DNA sequence" includes any part of (or the whole of) a DNA oligomer or polymer spanning three or more base pairs.

Embodiments of the invention that may be mentioned relate to compounds of formula I in which:
$R^{11}$ and $R^{12}$ independently represent, at each occurrence when used herein, H or $C_{1-6}$ alkyl (e.g. both $R^{11}$ and $R^{12}$ represent H).

Particular embodiments of the invention relate to compounds of formula I in which:
(a) the compound of formula I contains at least one $Q^a$ or $Q^b$ group that is other than a structural fragment of formula Ia;
(b) the compound of formula I contains at least one $Q^a$ or $Q^b$ group that represents
naphthyl (optionally substituted by one or more substituents selected from OH, halo, cyano, nitro, $N(R^{2a})R^{2b}$, $C_{1-4}$ alkyl and $C_{1-4}$ alkoxy),
$Het^3$,
or a structural fragment of formula Id or, particularly, If.

Other particular embodiments of the invention relate to compounds of formula I in which:
(i) $Q^a$ represents a structural fragment of formula Ia or If (e.g. a structural fragment of formula If), $Het^3$ or naphthyl (which latter group is optionally substituted by one or more substituents selected from OH, halo, cyano, nitro, $N(R^{2a})R^{2b}$, $C_{1-4}$ alkyl and $C_{1-4}$ alkoxy, but particularly unsubstituted naphthyl);
(ii) $Q^b$ represents $Het^3$ or, particularly, a structural fragment of formula Ia, Id or If.

Still other particular embodiments of the invention relate to compounds of formula I in which:
(I) when $Q^a$ represents a structural fragment of formula Ia, $Q^b$ represents $Het^3$ or, particularly, a structural fragment of formula Id or If (e.g. a structural fragment of formula If);
(II) one of $Q^a$ and $Q^b$ represents a structural fragment of formula If, and the other of $Q^a$ and $Q^b$ represents
naphthyl (optionally substituted by one or more substituents selected from OH, halo, cyano, nitro, $N(R^{2a})R^{2b}$, $C_{1-4}$ alkyl and $C_{1-4}$ alkoxy),
$Het^3$,
or a structural fragment of formula Ia, Ib, Ic, Id, Ie or If,
or $Q^a$ represents $Het^3$ and $Q^b$ represents
naphthyl (optionally substituted by one or more substituents selected from OH, halo, cyano, nitro, $N(R^{2a})R^{2b}$, $C_{1-4}$ alkyl and $C_{1-4}$ alkoxy),
$Het^3$ or
a structural fragment of formula Ia, Ib, Ic, Id, Ie or If;
(III) $Q^b$ represents $Het^3$, a structural fragment of formula Id or, particularly, If.

Yet further particular embodiments of the invention relate to compounds of formula I in which:
$R^1$ represents $NO_2$, —$N(R^{2a})R^{2b}$ or, particularly, H;
$R^{1a}$ represents H or $C_{1-8}$ alkyl;
a represents 1, 2 or 3 (e.g. 1 or 2);
A represents $C_{2-6}$ alkylene (e.g. $C_{2-3}$ n-alkylene);
D represents $Het^1$ or —$N(R^{3a})R^{3b}$;
$Het^1$ represents a five- to seven-membered heterocyclic group containing at least one N atom and optionally one or more heteroatoms selected from N, O and S, which heterocyclic groups are optionally substituted by one or more substituents selected from $C_{1-4}$ alkyl and $C_{1-4}$ alkoxy (e.g. $Het^1$ represents a six-membered heterocycle containing one N atom and either an O- or an S-atom, thus forming, for example, a thiomorpholine or, particularly, morpholine ring);
$R^{3a}$ and $R^{3b}$ represent $C_{1-4}$ alkyl (e.g. methyl);
$Q^a$ and $Q^b$ independently represent
naphthyl (optionally substituted by one or more substituents selected from halo, nitro, $N(R^{2a})R^{2b}$, $C_{1-3}$ alkyl and $C_{1-3}$ alkoxy) (e.g. unsubstituted naphthyl, such as unsubstituted naphth-2-yl),
$Het^3$,
or a structural fragment of formula Ia, Id or If,
$Q^c$ represents a structural fragment of formula Ia, Ib, Ic, Id or If (e.g. a structural fragment of formula Ia or Id);
$R^4$ represents H;
$R^5$ represents $C_{1-6}$ alkyl (e.g. methyl);
$R^8$ represents H or, particularly, $C_{1-8}$ alkyl (e.g. $C_{3-7}$ alkyl, such as isopropyl or, particularly, 3-methylbut-1-yl);
$R^{10}$ represents, independently at each occurrence, OH, halo, nitro, $N(R^{2a})R^{2b}$, $C_{1-3}$ alkyl and $C_{1-3}$ alkoxy (e.g. nitro or $C_{1-2}$ alkoxy, such as methoxy);
b represents 0, 1 or 2 (e.g. 0 or 1, such as 0 when $G^2$ represents N or 1 when $G^2$ represents CH or C—$R^{10}$);
$G^1$ represents CH;
$G^2$ represents CH or N;
$Het^3$ represents a ten-membered, bicyclic heterocyclic group containing a N-atom and optionally containing one or more heteroatoms selected from N, O and S, which group is optionally substituted by one or more substituents selected from halo (e.g. chloro), nitro, $N(R^{2a})R^{2b}$, $Het^a$, $C_{1-3}$ alkyl and $OR^a$ (e.g. a ten-membered, bicyclic heterocyclic group containing one or two N-atoms, which group is optionally substituted by one to three substituents selected from halo (e.g. chloro), nitro, $C_{1-2}$ alkyl and $OR^a$);
$R^a$ represents $C_{1-2}$ alkyl or, particularly, $Het^b$;
$Het^a$ and $Het^b$ independently represent ten- or, particularly, nine-membered heterocyclic groups containing one or more (e.g. one to three) heteroatoms selected from N, O and S, which heterocyclic groups are optionally substituted by one or more substituents selected from halo, nitro, $C_{1-2}$ alkyl and $C_{1-2}$ alkoxy (e.g. nine-membered, bicyclic heterocyclic groups containing one, two or, particularly, three N-atoms, which groups are optionally substituted by one to three substituents selected from halo, methyl and methoxy);
$R^{11}$ and $R^{12}$ both represent H;
$R^{2a}$ and $R^{2b}$ independently represent, at each occurrence when used herein, H or $C_{1-2}$ alkyl.

Particular embodiments of the invention relate to compounds of formula I in which:
(a) $Q^a$ represents $Het^3$ (e.g. quinolinyl, such as quinolin-2-yl or quinolin-3-yl);
(b) $Q^a$ represents naphthyl (optionally substituted by one or more selected from OH, halo, cyano, nitro, $N(R^{2a})R^{2b}$, $C_{1-4}$ alkyl and $C_{1-4}$ alkoxy) (e.g. unsubstituted naphthyl, such as unsubstituted naphth-2-yl);
(c) $Q^a$ represents a structural fragment of formula If;
(d) $Q^a$ represents a structural fragment of formula If in which $G^2$ represents CH (e.g. phenyl optionally substituted at the 3- or 4-position by $R^{10}$, wherein $R^{10}$ is as hereinbefore defined (e.g. nitro or, particularly, methoxy));
(e) $Q^a$ represents a structural fragment of formula If in which $G^2$ represents N (e.g. 3- or 4-pyridyl);
(f) $Q^a$ represents a structural fragment of formula Ia in which $G^1$ represents CH and $R^4$ and $R^5$ are as hereinbefore defined (e.g. $R^4$ represents H and $R^5$ represents methyl).

Other particular embodiments of the invention relate to compounds of formula I in which:
(i) $Q^b$ represents a structural fragment of formula If (e.g. a structural fragment of formula If in which $G^2$ represents CH or N and b represents 0, such as pyridinylene (e.g. 2,5-pyridinylene, for example wherein the 2-position of the pyridinyl ring is bound to the C-atom bearing the substituent $R^{12}$) or phenylene (e.g. 1,4-phenylene));
(ii) $Q^b$ represents (e.g. when $Q^a$ represents Het$^3$ or a structural fragment of formula If) a structural fragment of formula Ia (e.g. a structural fragment of formula Ia in which $G^1$ represents CH and $R^4$ and $R^5$ are as hereinbefore defined (e.g. $R^4$ represents H and $R^5$ represents methyl));
(iii) $Q^b$ represents (e.g. when $Q^a$ represents a structural fragment of formula If or, particularly, Het$^3$) a structural fragment of formula Id (e.g. a structural fragment of formula Id in which $R^8$ represents $C_{1-8}$ alkyl or, particularly, H);
(iv) $Q^b$ represents (e.g. when $Q^a$ represents a structural fragment of formula If) Het$^3$ (e.g. quinolinylene, such as 2,6-quinolinylene, for example wherein the 2-position of the quinolinyl ring is bound to the C-atom bearing the substituent $R^{12}$).

Further particular embodiments of the invention relate to compounds of formula I in which:
$Q^a$ and $Q^b$ are attached trans-relative to each other;
$R^{11}$ and $R^{12}$ both represent H;
a represents 2;
each $Q^c$ independently represents a structural fragment of formula Ia or Id, as hereinbefore defined.

Thus, embodiments of the invention that may be mentioned include those in which the compound of formula I is a compound of formula Ig

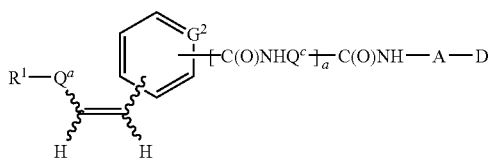

Ig wherein
the wavy lines indicate optional cis- or trans-stereochemistry;
$R^1$ represents $NO_2$, —$N(R^{2a})R^{2b}$ or, particularly, H;
a represents 1 or, particularly, 2;
$Q^a$ represents naphthyl (optionally substituted by one or more substituents selected from OH, halo, cyano, nitro, $N(R^{2a})R^{2b}$, C alkyl and $C_{1-4}$ alkoxy) or, particularly, Het$^3$ (e.g. quinolinyl, such as quinolin-2-yl or quinolin-3-yl) or a structural fragment of formula If;
$G^2$ represents CH or N; and
$R^{2a}$, $R^{2b}$, Het$^3$, $Q^c$, A and D are as hereinbefore defined.

Still further embodiments of the invention that may be mentioned include those in which, in the compound of formula Ig:
$R^1$ represents H;
a represents 2;
$Q^a$ and the 6-membered ring containing $G^2$ are attached trans-relative to each other;
$Q^a$ represents
  Het$^3$ (e.g. quinolinyl, such as quinolin-2-yl or quinolin-3-yl) or
  a structural fragment of formula If (e.g. phenyl optionally substituted at the 3- or 4-position by $R^{10}$, wherein $R^{10}$ is as hereinbefore defined (e.g. nitro or, particularly, methoxy));
$G^2$ represents CH (e.g. when $Q^a$ represents Het$^3$) or N (e.g. when $Q^a$ represents a structural fragment of formula If);
each $Q^c$ represents a structural fragment of formula Ia;
$G^1$ represents CH;
$R^4$ represents H;
$R^5$ represents $C_{1-6}$ alkyl (e.g. methyl);
A represents $C_3$ n-alkylene or, particularly, $C_2$ n-alkylene;
D represents —$N(R^{3a})R^{3b}$ or, particularly, Het$^1$;
Het$^1$ represents a six-membered heterocycle containing one N atom and either an O- or an S-atom, thus forming, for example, a thiomorpholine or, particularly, morpholine ring;
$R^{3a}$ and $R^{3b}$ represent $C_{1-4}$ alkyl (e.g. methyl).

Particular embodiments of the invention that may be mentioned include the compounds of the Examples disclosed hereinafter.

Alternative embodiments of the invention relate to compounds of formula I as hereinbefore defined, but in which:
a represents 0, 1, 2, 3 or 4; or
a represents 0.

Preferred compounds of formula I include those that bind to the minor groove of DNA.

Affinity to DNA may be measured by techniques known to those skilled in the art, such as capillary electrophoresis. Furthermore, affinity to certain sections of DNA may be determined by techniques known to those skilled in the art, such as DNA footprinting.

Preparation

Compounds of the invention may be prepared using techniques (e.g. peptide synthesis) known to those skilled in the art, using starting materials that are either commercially available, are known in the literature, or may be obtained either by analogy with the processes described hereinafter, or by conventional synthetic procedures, in accordance with standard techniques and using appropriate reagents and reaction conditions.

According to the invention there is also provided a process for the preparation of compounds of formula I which comprises:
(a) reaction of a compound of formula III,

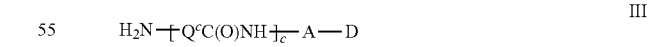

III wherein $Q^c$, D and A are as hereinbefore defined and c is as defined below, with a compound of formula IV,

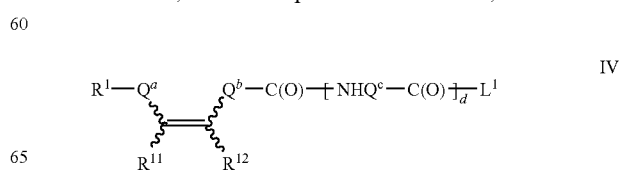

IV wherein $L^1$ represents a leaving group (such as OH, halo (e.g. Cl or Br) or —OC(O)$R^{14}$, wherein $R^{14}$ represents $C_{1-6}$ alkyl, $C_{1-6}$ alkenyl, $C_{5-6}$ cycloalkyl or aryl (which latter group is optionally substituted by one or more substituents selected from halo, cyano, nitro, $C_{1-4}$ alkyl and $C_{1-4}$ alkoxy)), c and d are both integers from 0 to 4, wherein the sum of c and d is from 1 to 4 and $R^1$, $R^{11}$, $R^{12}$, $Q^a$ to $Q^c$ and aryl are as hereinbefore defined, for example under conditions known to those skilled in the art (such as: (i) when $L^1$ represents OH, in the presence of a coupling agent (e.g. oxalyl chloride in DMF, EDC, DCC, HBTU, HATU, PyBOP or TBTU), an appropriate base (e.g. pyridine, DMAP, TEA, 2,4,6-collidine or DIPEA) and a suitable organic solvent (e.g. DCM, MeCN, EtOAc or DMF); or (ii) when $L^1$ represents halo or OC(O) $R^{14}$, in the presence of an appropriate base (e.g. pyridine, DMAP, TEA, 2,4,6-collidine or DIPEA) and a suitable organic solvent (e.g. DCM, MeCN, EtOAc or DMF));

(b) reaction of a compound of formula Va,

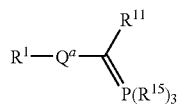

Va wherein $R^{15}$ represents aryl (which latter group is optionally substituted by one or more substituents selected from halo, cyano, nitro, $C_{1-4}$ alkyl and $C_{1-4}$ alkoxy) or $C_{1-6}$ alkyl), and $R^1$, $R^{11}$, $Q^a$ and aryl are as hereinbefore defined with a compound of formula VI

VI wherein A, a, D, $R^{12}$ $Q^b$, and $Q^c$ are as hereinbefore defined, for example under conditions known to those skilled in the art (such as in the presence of a suitable organic solvent (e.g. diethyl ether, THF, toluene));

(c) reaction of a compound of formula Vb,

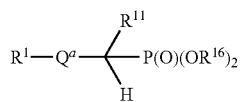

Vb wherein $R^{16}$ represents $C_{1-6}$ alkyl, and $R^1$, $R^{11}$, $Q^a$ and aryl are as hereinbefore defined with a suitable base (e.g. sodium hydride), for example under conditions known to those skilled in the art (such as in the presence of a suitable solvent (e.g. diethyl ether, THF, toluene)), followed by reaction with a compound of formula VI, as hereinbefore defined, for example under conditions known to those skilled in the art (such as in the presence of a suitable solvent (e.g. diethyl ether, THF, toluene));

(d) reaction of a compound of formula VIIa,

VIIa wherein $R^{12}$, $R^{15}$, $Q^b$, $Q^c$, a, A and D are as hereinbefore defined, with a compound of formula VIII,

VIII wherein $R^1$, $R^{11}$ and $Q^a$ are as hereinbefore defined, for example under conditions known to those skilled in the art (such as described in respect of process (b) above); or (e) reaction of a compound of formula VIIb,

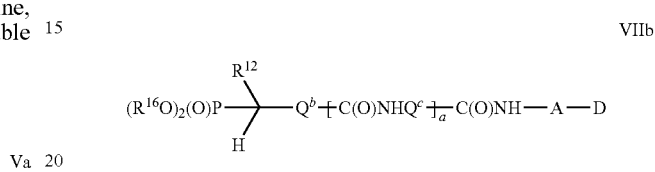

VIIb wherein $R^{12}$, $R^{16}$, $Q^b$, $Q^c$, a, A and D are as hereinbefore defined, with a suitable base (e.g. sodium hydride), for example under conditions known to those skilled in the art (such as described in process (c) above)), followed by reaction with a compound of formula VIII as hereinbefore defined, for example under conditions known to those skilled in the art (such as described in process (c) above)).

In an alternative embodiment for the preparation of compounds of formula I according to process (a) above, the integer c of the compound of formula III above and the integer d of the compound of formula IV above are both integers from 0 to 4, wherein the sum of c and d is from 0 to 4.

Compounds of formula IV may be prepared by:

(i) reaction of a compound of formula Va as defined hereinbefore with a corresponding compound of formula IX,

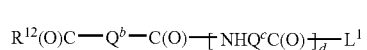

IX or a protected derivative thereof, wherein $L^1$, $Q^b$, $Q^c$, d and $R^{12}$ are as hereinbefore defined, for example under conditions known to those skilled in the art (such as described in respect of process (b) above), followed (if required) by conversion of one $L^1$ group to another (e.g. OH to halo, etc.);

(ii) reaction of a compound of formula Vb, as hereinbefore defined, with a suitable base (e.g. sodium hydride), for example under conditions known to those skilled in the art (such as those described in respect of process (c) above), followed by reaction with a compound of formula IX as hereinbefore defined (for example under conditions known to those skilled in the art, such as those described in respect of process (c) above);

(iii) reaction of a compound of formula Xa,

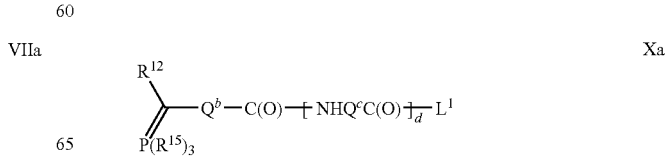

Xa or a protected derivative thereof, wherein $L^1$, $R^{12}$, $R^{15}$, $Q^b$, $Q^c$ and d are as hereinbefore defined, with a compound of formula VIII as hereinbefore defined, for example under conditions known to those skilled in the art (such as those described in relation to process (b) above); or (iv) reaction of a compound of formula Xb,

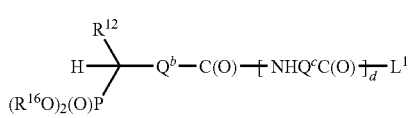
                                       Xb or a protected derivative thereof, wherein $L^1$, $R^{12}$, $R^{16}$, $Q^b$, $Q^c$ and d are as hereinbefore defined, with a suitable base (e.g. sodium hydride), for example under conditions known to those skilled in the art (such as in the presence of a suitable solvent (such as described in relation to process (c) above)), followed by reaction with a compound of formula VIII as hereinbefore defined, for example under conditions known to those skilled in the art (such as described in process (c) above).

Compounds of formula IV in which $Q^b$ represents quinoline ($Het^3$) or pyridine (a structural fragment of formula If), attached to $C(R^{12})$ via the 2-position of the ring system, and $R^{11}$ and $R^{12}$ both represent H may be prepared by reaction of a compound of formula XI,

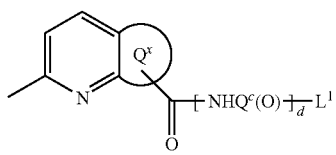
                                       XI or a protected derivative thereof, wherein $Q^x$ represents an optional fused benzene ring and $L^1$, $Q^c$, d and aryl are as hereinbefore defined, with a compound of formula XII

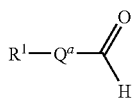
                                       XII wherein $R^1$ and $Q^a$ are as hereinbefore defined, for example under conditions known to those skilled in the art (for example conditions described in U.S. Pat. No. 4,009,174, such as in the presence of acetic anhydride and a suitable catalyst (e.g. zinc chloride) and, optionally, in the presence of a suitable solvent (e.g. an aromatic hydrocarbon such as xylene)).

Compounds of formula Va may be prepared by reaction of a compound of formula XIII,

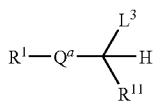
                                       XIII wherein $L^3$ is halo (e.g. Br, Cl) and $Q^a$, $R^1$ and $R^{11}$ are as hereinbefore defined, with a compound of formula XIV, $$P(R^{15})_3 \qquad\qquad\qquad\text{XIV}$$

wherein $R^{15}$ is as hereinbefore defined, for example under conditions known to those skilled in the art (such as in the presence of a suitable solvent (e.g. diethyl ether, THF, toluene) and a suitable base (e.g. sodium methoxide, n-butyl lithium, sodium hydride)), wherein the resulting compound of formula Va can be used without isolation (e.g. in a "one pot" preparation of a compound of formula I from a compound of formula XIII) or, alternatively, isolated before use.

Compounds of formula Vb may be prepared by reaction of a compound of formula XIII, as hereinbefore defined, with a compound of formula XV, $$P(O)(OR^{16})_3 \qquad\qquad\qquad\text{XV}$$

wherein $R^{16}$ is as hereinbefore defined, for example under conditions known to those skilled in the art (such as in the presence of a suitable solvent (e.g. diethyl ether, THF, toluene)).

Compounds of formula VI may be prepared by reaction of a compound of formula XVI,

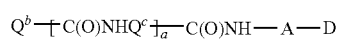
                                       XVI wherein $Q^b$, $Q^c$, a, A and D are as hereinbefore defined, with a compound of formula XVII,

                                       XVII wherein $L^3$ and $R^{12}$ are as hereinbefore defined, for example under conditions known to those skilled in the art (such as in the presence of a suitable catalyst (e.g. $FeCl_3$ or $AlCl_3$) and a suitable solvent (e.g. nitrobenzene, dichloromethane).

Compounds of formula VIIa may be prepared by reaction of a compound of formula XVIII,

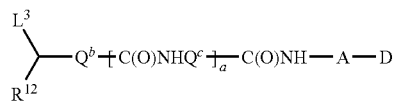
                                       XVIII wherein $L^3$, $Q^b$, $Q^c$, A, D, a and $R^{12}$ are as hereinbefore defined, with a compound of formula XIV, as hereinbefore defined, for example under conditions known to those skilled in the art (such as in the presence of a suitable solvent (e.g. diethyl ether, THF, toluene) and a suitable base (e.g. sodium methoxide, n-butyl lithium, sodium hydride)), wherein the resulting compound of formula VIIa can be used without isolation (e.g. in a "one pot" preparation of a compound of formula I from a compound of formula XVIII) or, alternatively, isolated before use.

Compounds of formula VIIb may be prepared by reaction of a compound of formula XVIII, as hereinbefore defined, with a compound of XV, as hereinbefore defined, for example under conditions known to those skilled in the art (such as in the presence of a suitable solvent (e.g. diethyl ether, THF, toluene)).

Compounds of formula IX may be prepared by reaction of a compound of formula XIX,

XIX or a protected derivative thereof, wherein $Q^b$, $Q^c$, d and $L^1$ are as hereinbefore defined, with a compound of formula XVII, as hereinbefore defined, for example under conditions known to those skilled in the art (such as those described above in relation to the synthesis of compounds of formula VI).

Compounds of formula Xa may be prepared by reaction of a compound of formula XX,

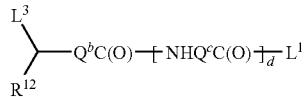

XX or a protected derivative thereof, wherein $Q^b$, $Q^c$, $L^1$, $L^3$, d and $R^{12}$ are as hereinbefore defined, with a compound of formula XIV, as hereinbefore defined, for example under conditions known to those skilled in the art (such as in the presence of a suitable solvent (e.g. diethyl ether, THF, toluene) and a suitable base (e.g. sodium methoxide, n-butyl lithium, sodium hydride)), wherein the resulting compound of formula Xa can be used without isolation (e.g. in a "one pot" preparation of a compound of formula IV from a compound of formula XX) or, alternatively, isolated before use.

Compounds of formula Xb may be prepared by reaction of a compound of formula XX, as hereinbefore defined, with a compound of XV, as hereinbefore defined, for example under conditions known to those skilled in the art (such as in the presence of a suitable solvent (e.g. diethyl ether, THF, toluene)).

Compounds of formula XIII may be prepared by reaction of a compound of formula XXI,

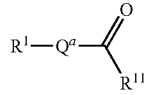

XXI wherein $R^1$, $Q^a$ and $R^{11}$ are as hereinbefore defined, with a reducing agent (e.g. LiAlH$_4$, NaBH$_4$), for example under conditions known to those skilled in the art (such as in the presence of a suitable solvent (e.g. diethyl ether, THF, toluene)), followed by reaction of the resultant intermediate alcohol with a reagent suitable for effecting the displacement of —OH with a halogen atom (e.g. thionyl chloride or sodium iodide combined with a suitable catalyst (e.g. ZrCl$_4$)), for example under conditions known to those skilled in the art (such as in the presence of a suitable solvent (e.g. diethyl ether, THF or acetonitrile).

Compounds of formula XVIII may be prepared by reaction of a compound of formula VI as hereinbefore defined, with a reducing agent (e.g. LiAlH$_4$, NaBH$_4$), for example under conditions known to those skilled in the art (such as in the presence of a suitable solvent (e.g. diethyl ether, THF, toluene)), followed by reaction of the resultant intermediate alcohol with a reagent suitable for effecting the displacement of —OH with a halogen atom (e.g. as described above).

Compounds of formula XX may be prepared by reaction of a corresponding compound of formula IX, as hereinbefore defined (or a protected derivative thereof), with a reducing agent (e.g. LiAlH$_4$, NaBH$_4$), for example under conditions known to those skilled in the art (such as in the presence of a suitable solvent (e.g. diethyl ether, THF, toluene)), followed by reaction of the resultant intermediate alcohol with a reagent suitable for effecting the displacement of —OH with a halogen atom (e.g. as described above).

Compounds of formula XXI may be prepared by reaction of a compound of formula XXII,

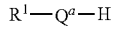

XXII wherein $R^1$ and $Q^a$ are as hereinbefore defined, with a compound of formula XXIII,

XXIII wherein $L^3$ and $R^{11}$ are as hereinbefore defined, for example under conditions known to those skilled in the art (such as in the presence of a suitable catalyst (e.g. FeCl$_3$ or AlCl$_3$) and a suitable solvent (e.g. nitrobenzene, dichloromethane).

Compounds of formulae III, VIII, XI, XII, XIV to XVII, XIX, XXII, XXIII, and derivatives thereof, are either commercially available, are known in the literature, or may be obtained either by analogy with the processes described herein or in WO 2003/059881, or by conventional synthetic procedures, in accordance with standard techniques, from readily available starting materials using appropriate reagents and reaction conditions.

Substituents on the aryl (e.g. phenyl), and heterocyclic, group(s) in compounds defined herein may be converted to other claimed substituents using techniques well known to those skilled in the art. For example, hydroxy may be converted to alkoxy, phenyl may be halogenated to give halophenyl, nitro may be reduced to give amino, halo may be displaced by cyano, etc.

The skilled person will also appreciate that various standard substituent or functional group interconversions and transformations within certain compounds of formula I will provide other compounds of formula I. For example chloro may be displaced by alkoxy, aryloxy or heteroaryloxy, carbonyl may be reduced to hydroxy or methylene and hydroxy converted to halo.

The compounds of the invention may be isolated from their reaction mixtures using conventional techniques.

It will be appreciated by those skilled in the art that, in the process described above, the functional groups of intermediate compounds may be, or may need to be, protected by protecting groups.

Functional groups which it is desirable to protect include hydroxy, amino and carboxylic acid. Suitable protecting groups for hydroxy include trialkylsilyl and diarylalkylsilyl groups (e.g. tert-butyldimethylsilyl, tert-butyldiphenylsilyl or trimethylsilyl), tetrahydropyranyl and alkylcarbonyl groups (e.g. methyl- and ethylcarbonyl groups). Suitable protecting groups for amino include benzyl, tert-butyloxycarbonyl, 9-fluorenylmethoxycarbonyl or benzyloxy-carbonyl. Suitable protecting groups for carboxylic acid include $C_{1-6}$ alkyl or benzyl esters.

The protection and deprotection of functional groups may take place before or after any of the reaction steps described hereinbefore.

Protecting groups may be removed in accordance with techniques which are well known to those skilled in the art and as described hereinafter.

The use of protecting groups is fully described in "Protective Groups in Organic Chemistry", edited by J. W. F. Mcmie, Plenum Press (1973), and "Protective Groups in Organic Synthesis", 3rd edition, T. W. Greene & P. G. M. Wutz, Wiley-Interscience (1999).

Persons skilled in the art will appreciate that, in order to obtain compounds of the invention in an alternative, and, on some occasions, more convenient, manner, the individual process steps mentioned herein may be performed in a different order, and/or the individual reactions may be performed at a different stage in the overall route (i.e. substituents may be added to and/or chemical transformations performed upon, different intermediates to those associated hereinbefore with a particular reaction). This will depend inter alia on factors such as the nature of other functional groups present in a particular substrate, the availability of key intermediates and the protecting group strategy (if any) to be adopted. Clearly, the type of chemistry involved will influence the choice of reagent that is used in the said synthetic steps, the need, and type, of protecting groups that are employed, and the sequence for accomplishing the synthesis.

Uses and Pharmaceutical Preparations

Compounds of the invention are useful because they possess pharmacological activity. They are therefore indicated as pharmaceuticals.

Thus, according to a further aspect of the invention there is provided the compounds of the invention for use as pharmaceuticals.

In particular, compounds of the invention bind to DNA, thereby displacing, or inhibiting the binding to that DNA of, enzymes or regulatory proteins. Enzymes that may be mentioned in this respect include those necessary for replication (thus providing the effect of inhibiting DNA replication) as well as those involved in transcription (thus providing the effect of inhibiting the expression of certain peptides (proteins, enzymes, etc.)).

Thus, according to a further aspect of the invention there is provided a method of inhibiting DNA replication, which method comprises contacting the DNA with an inhibitory amount of a compound of the invention.

Due to their ability to inhibit DNA replication (e.g. by inhibiting transcription by blocking the binding or displacement of regulatory proteins or DNA-enzyme complexes, such as with reverse transcriptase or topoisomerases), compounds of the invention have utility in the treatment of diseases that rely upon DNA replication for their propagation. Such diseases include cancers and those involving viruses, bacteria, fungi or other microorganisms (e.g. diseases involving parasites, such as malaria).

Thus, according to a further aspect of the invention, there is provided a method of treatment of a disease that relies upon DNA replication for its propagation (e.g. cancer or a viral, bacterial, fungal or other microbial infection), which method comprises administration of a therapeutically effective amount of a compound of the invention to a person suffering from that disease. Such treatment may be particularly useful where the person suffering from that disease is immunocompromised.

Because they have a different mode of action to many conventional anti-viral, anti-bacterial, anti-fungal or other anti-microbial (e.g. anti-parasitic) agents, compounds of the invention may be particularly useful in the treatment of viral, bacterial, fungal or other microbial (e.g. parasitic) infections where the infective agent is resistant to one or more anti-viral, anti-bacterial, anti-fungal or other anti-microbial (e.g. anti-parasitic) agents having a different mode of action. In this respect, according to a further aspect of the invention there is provided a method of treating a viral, bacterial, fungal or other microbial (e.g. parasitic) infection, where the viral, bacterial, fungal or other microbial (e.g. parasitic) infective agent is resistant to one or more anti-viral, anti-bacterial, anti-fungal or other anti-microbial (e.g. anti-parasitic) agents, respectively, that do not act by inhibiting DNA replication, which method comprises administration of a therapeutically effective amount of a compound of the invention to a person having that infection.

As well as having utility on their own in the treatment of diseases that rely upon DNA replication for their propagation, the compounds of the invention may be used in combination with one or more other compounds or treatment regimes that are used to treat such a disease. Thus, according to a further aspect of the invention, there is provided a method of treatment of a disease that relies upon DNA replication for its propagation (e.g. cancer or a viral, bacterial, fungal or other microbial infection), which method comprises administration, to a person suffering from that disease, of a therapeutically effective amount of a compound of the invention in combination with one or more other agents that are known to be effective in treating that disease.

When used herein, the term "in combination with" includes administration of the other agent(s) that is(are) known to be effective in treating the disease, before, during and/or following administration a compound of the invention. When more than one other agent is administered, the term also includes administration of the different other agents at different times relative to the time of administration of a compound of the invention.

Agents that are known to be effective in treating diseases that rely upon DNA replication for their propagation (e.g. anti-cancer, anti-viral, anti-bacterial, anti-fungal or other anti-microbial (e.g. anti-parasitic) agents) include those listed under the relevant headings in "*Martindale: The Complete Drug Reference*", $32^{nd}$ Edition, the Pharmaceutical Press, London (1999), the disclosures of which document are hereby incorporated by reference.

Anti-cancer agents also include non-chemical agents such as ionising radiation (e.g. subatomic particle radiation such as α-particles, β-particles, neutrons, protons, mesons and heavy ions or electromagnetic radiation such as high-frequency X-rays or gamma rays). Chemical anti-cancer agents that may be mentioned include:

(a) Alkylating agents including:
  (i) nitrogen mustards such as mechlorethamine ($HN_2$), cyclophosphamide, ifosfamide, melphalan (L-sarcolysin) and chlorambucil;
  (ii) ethylenimines and methylmelamines such as hexamethylmelamine, thiotepa;
  (iii) alkyl sulfonates and thiosulfonates such as busulfan, methyl methanesulfonate (MMS) and methyl methanethiosulfonate;
  (iv) nitrosoureas and nitrosoguanidines such as carmustine (BCNU), lomustine (CCNU), semustine (methyl- CCNU), streptozocin (streptozotocin) and N-methyl-N'-nitro-N-nitrosoguanidine (MNNG); and
(v) triazenes such as dacarbazine (DTIC; dimethyltriazenoimidazole-carboxamide).
(b) Antimetabolites including:
(i) folic acid analogues such as methotrexate (amethopterin);
(ii) pyrimidine analogues such as fluorouracil (5-fluorouracil; 5-FU), floxuridine (fluorodeoxyuridine; FUdR) and cytarabine (cytosine arabinoside); and
(iii) purine analogues and related inhibitors such as mercaptopurine (6-mercaptopurine; 6-MP), thioguanine (6-thioguanine; TG) and pentostatin (2'-deoxycoformycin).
(c) Natural Products including:
(i) vinca alkaloids such as vinblastine (VLB) and vincristine;
(ii) epipodophyllotoxins such as etoposide and teniposide;
(iii) antibiotics such as dactinomycin (actinomycin A, C, D or F), daunorubicin (daunomycin; rubidomycin), doxorubicin, bleomycin, plicamycin (mithramycin) and mitomycin (mitomycin A, B or C);
(iv) enzymes such as L-asparaginase; and
(v) biological response modifiers such as interferon alphenomes.
(d) Miscellaneous agents including:
(i) platinum coordination complexes such as cisplatin (cis-DDP) and carboplatin;
(ii) anthracenedione such as mitoxantrone and anthracycline;
(iii) substituted urea such as hydroxyurea;
(iv) methyl hydrazine derivatives such as procarbazine (N-methylhydrazine, MIH);
(v) adrenocortical suppressants such as mitotane (o,p'-DDD) and aminoglutethimide;
(vi) taxol and analogues/derivatives;
(vii) hormone agonists/antagonists such as flutamide and tamoxifen;
(viii) photoactivatable compounds (e.g. psoralens);
(ix) DNA topoisomerase inhibitors (e.g. m-amsacrine and camptothecin);
(x) anti-angiogenesis agents (e.g. SU6668, SU5416, combretastatin A4, angiostatin and endostatin); and
(xi) immunotherapeutic agents (e.g. radiolabelled antibodies such as Bexxar™ and Theragynr™ (Pemtumomab™)).

Anti-viral agents that may be mentioned include acyclovir, gancyclovir, AZT, ddI, amantadine hydrochloride, inosine pranobex, vidarabine, and the like.

Anti-bacterial agents that may be mentioned include natural and synthetic penicillins and cephalosporins, sulphonamides, erythromycin, kanomycin, tetracycline, chloramphenicol, rifampicin and including gentamicin, ampicillin, benzypenicillin, benethamine penicillin, benzathine penicillin, phenethicillin, phenoxy-methyl penicillin, procaine penicillin, cloxacillin, flucloxacillin, methicillin sodium, amoxicillin, bacampicillin hydrochloride, ciclacillin, mezlocillin, pivampicillin, talampicillin hydrochloride, carfecillin sodium, piperacillin, ticarcillin, mecillinam, pirmecillinan, cefaclor, cefadroxil, cefotaxime, cefoxitin, cefsulodin sodium, ceftazidime, ceftizoxime, cefuroxime, cephalexin, cephalothin, cephamandole, cephazolin, cephradine, latamoxef disodium, aztreonam, chlortetracycline hydrochloride, clomocycline sodium, demeclocydine hydrochloride, doxycycline, lymecycline, minocycline, oxytetracycline, amikacin, framycetin sulphate, neomycin sulphate, netilmicin, tobramycin, colistin, sodium fusaidate, polymyxin B sulphate, spectinomycin, vancomycin, calcium sulphaloxate, sulfametopyrazine, sulphadiazine, sulphadimidine, sulphaguanidine, sulphaurea, capreomycin, metronidazole, tinidazole, cinoxacin, ciprofloxacin, nitrofurantoin, hexamine, streptomycin, carbenicillin, colistimethate, polymyxin B, furazolidone, nalidixic acid, trimethoprim-sulfamethoxazole, clindamycin, lincomycin, cycloserine, isoniazid, ethambutol, ethionamide, pyrazinamide and the like.

Anti-fungal agents that may be mentioned include miconazole, ketoconazole, itraconazole, fluconazole, fusidic acid, amphotericin, flucytosine, griseofulvin, natamycin, nystatin, and the like.

Anti-parasitic agents (e.g. anti-malarial agents) that may be mentioned include pyrimethamine, proguanil, chloroquine, primaquine, mefloquine, quinine, tetracycline, atovaquone, artemisinin, dihydroartemisinin, artemether, arteether, artesunic acid and its salts, and sulfonamides.

When a compound of the invention is administered to a patient in combination with one or more other agents that are known to be effective in treating diseases that rely upon DNA replication for their propagation, the compound of the invention and the other agent(s) may be administered separately or, conveniently, as a single composition. Thus, according to a further aspect of the invention, there is provided a combination product comprising components:

(A) a formulation comprising a compound of the invention; and
(B) a formulation comprising one or more other chemical agents that are known to be effective in treating diseases that rely upon DNA replication for their propagation.

The combination product according to this aspect of the invention provides for the administration of a compound of the invention in conjunction with one or more other chemical agents that are known to be effective in treating diseases that rely upon DNA replication for their propagation, and may thus be presented either as separate components (i.e. (A) and (B) separately), or may be presented (i.e. formulated) as a combined preparation (i.e. presented as a single formulation including a compound of the invention and one or more other chemical agents that are known to be effective in treating diseases that rely upon DNA replication for their propagation). When components (A) and (B) are presented as separate components, the combination product may alternatively be termed "a kit-of-parts".

In this aspect of the invention, other chemical agents that are known to be effective in treating diseases that rely upon DNA replication for their propagation include those referred to or mentioned hereinbefore. Thus, in a preferred embodiment of this aspect of the invention, the other chemical agents that are known to be effective in treating diseases that rely upon DNA replication for their propagation are one or more chemical anti-cancer, anti-viral, anti-bacterial, anti-fungal and/or anti-parasitic agents (e.g. the agents referred to or mentioned hereinbefore).

In a further preferred embodiment of this aspect of the invention each of components (A) and (B) is formulated in admixture with a pharmaceutically-acceptable adjuvant, diluent or carrier.

The compounds of the invention will normally be administered orally, subcutaneously, intravenously, intraarterially, transdermally, intranasally, by inhalation, or by any other parenteral route, in the form of pharmaceutical preparations comprising the active ingredient either as a free base or a non-toxic organic or inorganic acid addition salt, in a pharmaceutically acceptable dosage form. Depending upon the disorder and patient to be treated, as well as the route of administration, the compositions may be administered at varying doses.

According to a further aspect of the invention there is thus provided a pharmaceutical formulation including a compound of the invention in admixture with a pharmaceutically acceptable adjuvant, diluent or carrier. Such formulations may be used for the treatment of diseases that rely upon DNA replication for their propagation. Thus, in one embodiment of this aspect of the invention there is provided a pharmaceutical formulation including, in admixture with a pharmaceutically acceptable adjuvant, diluent or carrier, a compound of the invention and one or more other chemical agents that are known to be effective in treating diseases that rely upon DNA replication for their propagation (e.g. one or more chemical anti-cancer, anti-viral, anti-bacterial, anti-fungal and/or anti-parasitic agents, such as the agents referred to or mentioned hereinbefore).

Suitable daily doses of the compounds of the invention in therapeutic treatment of humans are about 1 to 2000 mg/m$^2$.

The most effective mode of administration and dosage regimen for the compounds of the invention depends on several factors, including the particular condition being treated, the extent and localisation of that condition in the patient being treated, as well as the patient's state of health and their reaction to the compound being administered. Accordingly, the dosages of the compounds of the invention should be adjusted to suit the individual patient. Methods for determining the appropriate dose for an individual patient will be known to those skilled in the art.

As well as having utility in the treatment of diseases, compounds of the invention are also useful in various assay methods based upon DNA binding. For example, it is known that compounds that bind to the minor groove of DNA have the ability to stabilise DNA duplexes, as well as to stabilise a fully matched (in terms of base pairs) DNA duplex to a greater extent than a mismatched DNA duplex, thereby enabling easier discrimination between the fully matched and mismatched duplexes (e.g. in terms of the melting temperatures of the duplexes).

Thus, according to a further aspect of the invention, there is provided a method of stabilising a DNA duplex formed between first and second single strands of DNA, which method comprises contacting that DNA duplex with a compound of the invention.

Further, there is also provided a method of enhancing the difference in melting temperatures between first and second DNA duplexes, wherein each DNA duplex is formed from a first single strand of DNA that is the same in each duplex and a second single strand of DNA that is different in each duplex, which method comprises contacting each DNA duplex with a compound of the invention. In a preferred embodiment, the first DNA duplex has a greater degree of base-pair matching (e.g. it is fully matched) than the second DNA duplex, which has at least one base-pair mismatch.

Compounds that stabilise fully matched DNA duplexes to a greater extent than mismatched DNA duplexes may be used to reduce levels of "false positive" results in DNA hybridisation assay techniques, for example as described in U.S. Pat. No. 6,221,589, the disclosures of which are hereby incorporated by reference. The reduction in "false positive" results may be achieved through the use of more stringent conditions (e.g. higher wash temperatures) following a hybridisation reaction in the presence of a duplex-stabilising compound than is possible following a reaction in the absence of such a compound. Thus, there is further provided a method of increasing the maximum temperature of a wash following a DNA hybridisation reaction, the method comprising the provision of a compound of the invention to the hybridisation reaction mixture. When used herein, the term "maximum temperature of a wash following a DNA hybridisation reaction" refers to the highest possible wash temperature that does not result in a substantial loss of the "true positive" results (i.e. the fully or most highly matched DNA duplexes).

When used herein in relation to the above-mentioned methods involving DNA duplexes, the term "contacting" includes admixing of a compound of the invention with a DNA duplex. However, the term also includes attaching (e.g. covalently bonding) a compound of the invention (e.g. a compound of the invention bearing a haloalkyl group), or a derivative thereof (e.g. a compound of formula V) that bears a functional group (e.g. a hydroxy, amino or carboxylic acid group) that may be used to form a suitable attachment, to one or both of the single strands of DNA that form the duplex. Such "labeled" single strands of DNA may be used as primers, capture probes, or in a number of different assays (e.g. capture-detection assays, 5'-nuclease assays and Beacon assays).

Compounds of the invention may also possess fluorescence properties. Fluorescent compounds of the invention may be useful in various assay methods based upon DNA binding which involve or require fluorescence.

Thus, according to a further aspect of the invention, there is provided a method of detecting dsDNA in a sample, said method comprising contacting a compound of the invention with the sample and comparing the fluorescence of said compound in contact with said sample with the fluorescence of said compound in isolation, a change in fluorescence indicating the presence of DNA in the sample.

In this embodiment of the invention, a change in fluorescence may be, for example, a change in the wavelength of light emitted by the compound of the invention, a change in the wavelength of light absorbed by said compound or a change in the intensity of light emitted by said compound. Further, the dsDNA may also, in a particular embodiment, be labelled with a fluorophore. When labelled in this way (and even when not so labelled), the dsDNA can act as a donor or acceptor in a "FRET"-type assay for detecting the presence of dsDNA.

In an alternative embodiment of the invention, there is provided a method of detecting and visualising dsDNA in a sample containing dsDNA, said method comprising contacting the sample with a compound of the invention and then visualising dsDNA by irradiating the sample with ultraviolet light. In this embodiment of the invention, the sample might derive from agarose gel electrophoresis experiments or from DNA microarrays.

A specific advantage that compounds of the invention may possess is, that once bound to the minor groove of dsDNA their disassociation is relatively slow (e.g. resulting in a dissociation constant in the range of 0.1 to 10 nM for disassociating from the minor groove of DNA), meaning that the pharmacodynamic effectiveness of the compounds may last for a significantly longer period than that suggested by their plasma concentration levels in vivo. For a discussion of such an effect, see: *Nucleic Acid Res.* 26, 3053-3058 (1998); and Chapter 2 of *Pharmacokinetics and Metabolism in Drug Design*, Smith et al., Mannhold et al. Eds, Wiley-VCH, Weinheim, 2001.

In relation to the above, the dissociation constant from the minor groove of dsDNA may be determined, for example, by determination of melting temperatures of various mixtures of compounds of the invention with DNA, or by microcalorimetry measurements.

Compounds of the invention may also have the advantage that they may be more efficacious than, be less toxic than, have a broader range of activity than, be more potent than, be longer acting than, produce fewer side effects than, be more easily absorbed than, or that they may have other useful pharmacological properties over, compounds known in the prior art.

Biological Tests

The effects of compounds of the invention in relation to inhibiting the growth of various microorganisms was determined using methods known to those skilled in the art, for example in vitro methods as described in *J. Med. Chem.* 47, 2133-2156 (2004) and in vivo methods as described in *J. Med. Microbiol.* 46, 208-213 (1997), the disclosures of which documents are hereby incorporated by reference.

In Vitro Tests

In particular, minimum inhibitory concentrations (MICs) against microorganisms (e.g. *S. Aureus, Streptococcus faecalis, Aspergillus niger, Candida albicans* or *Mycobacterium fortuitum*) for compounds of the invention may be measured using procedures such as those described in A. J. Drummond and R. D. Waigh "The development of microbiological methods for phytochemical screening" *Recent Res. Devel. Phytochem.* 4, 143-152 (2000), the disclosures of which document are hereby incorporated by reference.

Sample dilutions were typically prepared by dissolving the test sample (2 mg) in sterile water (10 mL) to provide a working concentration of 200 μg/ml. The test wells on each 96 well microtitre plate were initially inoculated with culture medium (100 μL) using Mueller-Hinton Broth for antibacterial assays and Sabouraud Broth for antifungal assays. A solution of each test sample (100 μL) was added to one row of each plate and a series of doubling dilutions made for successive rows. Incubation was at 37° C. for antibacterial assay and 25° C. for antifungal assay. Plates were inspected visually for growth and Resazurin was added to each well; a distinct colour change from blue to red indicated that growth had occurred in an individual well. From the observed pattern of colour, the MIC was determined. All tests included sterility and growth controls.

In Vivo Tests

Toxicity of the compounds of the invention can also be determined by direct and indirect methods known to those skilled in the art, such as those described in *J. Immunol. Methods* 94, 57-63 (1986), the disclosures of which document are hereby incorporated by reference.

In relation to the methods described in *J. Med. Microbiol.* 46, 208-213 (1997), compounds may be evaluated in vivo using a model *S. Aureus* strain LS-1 which, when injected intravenously into mice, consistently causes transient bacteraemia followed by joint localization in 3-4 days. Normal control mice show inflammation of 50-60% of their joints within 3-4 days. The severity of joint sepsis was measured using calipers to determine the diameter of the affected joints. In general, five groups of mice normally having a mean weight of between 18-28 g (5 mice per group) are used for each compound tested, wherein each group is infected with *S. Aureus* and then provided with a certain dose of the compound to be tested (with one group acting a control).

EXAMPLES

General Experimental Procedures

Electrospray mass spectra (ES-MS) were obtained on a Fisons® VG Platform Benchtop LC-MS. Electron impact (EI-MS) and fast atom bombardment (FAB-MS) mass spectra were obtained on a Jeol® JMS-AX505HA mass spectrometer. Accurate mass recorded at the University of Glasgow on Jeol JMS-700 Mstation, high resolution magnetic sector mass spectrometer.

NMR spectra were obtained on a Bruker® AMX 400 spectrometer operating at 400 MHz for $^1$H. In $^1$H NMR spectra, the abbreviation 'exch.' signifies that the relevant resonance disappeared on treatment of the solution with $D_2O$.

HPLC purification of the final products was carried out using a Vydac protein and peptide C18 column on a gradient eluting system. The solvents were A: water+0.1% trifluoroacetic acid (TFA), and B: acetonitrile+0.1% TFA. All the final products obtained after purification by HPLC were freeze-dried and obtained as TFA salts.

IR spectra: solids were run as KBr discs and liquids as films, using a Nicolet® Impact 400D.

Column chromatography was performed with silica gel Prolabo® (200-400 mash).

Preparation 1

4-Amino-1-methyl-N-[1-methyl-5-({[2-(4-morpholinyl)ethyl]amino}carbonyl)-1H-pyrrol-3-yl]-1H-pyrrole-2-carboxamide (i) 1-Methyl-4-nitro-1H-pyrrole-2-carboxylic acid (See, for example, Suckling, C. J., Khalaf, A. I., Pitt A. R., Scobie, M., *Tetrahedron,* 2000, 56, 5225.)

$HNO_3$ (70%) (8.4 mL) was added dropwise to acetic anhydride (40 mL) at −25° C., and allowed to stir for a further 20 min. This solution was added dropwise to a solution of the commercially available 1-methyl-1H-pyrrole-2-carboxylic acid (Aldrich) (7.74 g, 61.9 mmol), in acetic anhydride (60 mL) at −25° C. and allowed to return to RT over 2 h. The solution was cooled to −40° C., at which point a precipitate formed. This was collected and washed with hexane, before being dried under reduced pressure to the desired product (2.21 g, 21%).

m.p.=199-201° C., (lit.=199-199.5° C.).

IR (KBr): 3500-2500 υ(O—H), 3141 υ(N-Me), 2920 υ(C—H), 1702 υ(C=O), 1422, 1399 υ(N—O), 1269υ(C—O) cm$^{-1}$.

$^1$H NMR (CDCl$_3$): 4.04 (3H, s, CH$_3$), 7.51 (1H, d, Ar—H, J=1.6 Hz), 7.71 (1H, d, Ar—H, J=1.6 Hz).

(ii) 1-Methyl-4-nitro-1H-pyrrole-2-carbonyl chloride (See, for example, Suckling, C. J., Khalaf, A. I., Pitt A. R., Scobie, M., *Tetrahedron,* 2000, 56, 5225.)

1-Methyl-4-nitro-1H-pyrrole-2-carboxylic acid (0.510 g, 3.02 mmol; see step (i) above) was placed in a round bottom flask with thionylchloride (7 mL) and the solution refluxed under N$_2$ for 2 h. The solvent was then removed under reduced pressure to yield the product as a white to off-white solid (0.556 g, 98%).

m.p.=91-92° C. (lit.=91-92° C.).

IR (KBr): 3126 υ(N-Me), 2974 υ(Ar—H), 1744 υ(C=O), 1511, 1314υ(N=O), 592 δ(C—Cl) cm$^{-1}$.

$^1$H NMR (DMSO): 3.91 (3H, s, CH$_3$), 7.25 (1H, d, Ar—H, J=1.6 Hz), 8.22 (1H, d, Ar—H, J=1.6 Hz).

(iii) 1-Methyl-N-[2-(4-morpholinyl)ethyl]-4-nitro-1H-pyrrole-2-carboxamide (See, for example, Kaizerman, J. A., Gross, M. I., Ge, Y, White, S Hu, W, Duan, J, Baird, E. E., Johnson, K. W., Tanaka, R. D., Moser, H. E., Berli, R. W., *J. Med. Chem.,* 2003, 46, 3914.)

1-Methyl-4-nitro-1H-pyrrole-2-carbonyl chloride (0.585 g, 4.70 mmol; see step (ii) above) in DCM (10 mL), was added dropwise to a solution of 2-(4-morpholinyl)ethanamine (0.673 g, 5.17 mmol), and NEt$_3$ (0.735 µL, 9.42 mmol), in DCM (10 mL) over 15 min. The resulting solution was allowed to stir overnight and the reaction quenched with a 5% NaOH solution (20 mL). The layers were separated and the DCM fraction collected, dried (MgSO$_4$), filtered and the solvent removed under reduced pressure to yield the sub-title compound as a white/pale yellow solid (1.166 g, 88%).

m.p.=141-143° C., (lit=143-145° C.).

$v_{max}$ KBr/cm$^{-1}$: 3325 υ(N—H), 3118, 3023 υ(Ar—H), 2967, 2865, υ(C—H), 1638 υ(C═O), 1539, 1311 υ(N═O), 1146 υ(C—O—C).

$δ_H$ $^1$H (DMSO): 2.40 (4H, m, 2(CH$_2$)), 3.31 (4H, q, (CH$_2$)—N—(CH$_2$) (J=6.8 Hz)), 3.56 (4H, t, (CH$_2$)—O—(CH$_2$) (J=4.6 Hz)), 3.89 (3H, s, N-Me), 7.39 (1H, d, Ar—H (J=1.6 Hz)), 8.10 (1H, d, Ar—H (J=1.6 Hz)), 8.33 (1H, t, NH (J=5.6 Hz)).

LREIMS: Found 283.08 (M+H) calculated for C$_{12}$H$_{18}$N$_4$O$_4$ 282.13.

(iv) 1-Methyl-4-{[(1-methyl-4-nitro-1H-pyrrol-2-yl)carbonyl]amino}-N-[2-(4-morpholinyl)ethyl]-1H-pyrrole-2-carboxamide (See, for example, Kaizerman, J. A., Gross, M. I., Ge, Y, White, S Hu, W, Duan, J, Baird, E. E., Johnson, K. W., Tanaka, R. D., Moser, H. E., Berli, R. W., *J. Med. Chem.*, 2003, 46, 3914.)

1-Methyl-N-[2-(4-morpholinyl)ethyl]-4-nitro-1H-pyrrole-2-carboxamide (1.42 g, 3.41 mmol; see step (iii) above) was dissolved in methanol (10 mL) and cooled to 0° C., Pd/C (0.055 g) was then added in small portions and the solution stirred under H$_2$ for 3 h. The solution was then filtered and the solvent removed under reduced pressure. A solution of 1-methyl-4-nitro-1H-pyrrole-2-carbonyl chloride (0.642 g, 3.42 mmol) in DCM (10 mL) was added and the mixture allowed to stir for 1 h at RT. The solvent was then removed under reduced pressure and the crude product was separated on basified silica using a 1:1 solution of methanol ethyl acetate to yield the sub-title compound.

Yield=0.923 g, 67%, m.p.>230° C.

$v_{max}$ KBr/cm$^{-1}$: 3339, 3284 υ(N—H), 3135, 3068 υ(Ar—H), 2929, 2867, υ(C—H), 1666, 1635 υ(C═O), 1537, 1306 υ(N═O), 1112 δ(C—O).

$δ_H$ $^1$H (DMSO): 2.42 (4H, m, 2(CH$_2$)), 3.30 (4H, q, (CH$_2$)—N—(CH$_2$) (J=6.8 Hz)), 3.57 (4H, t, (CH$_2$)—O—(CH$_2$) (J=4.6 Hz)), 3.80 (3H, s, N-Me), 3.94 (3H, s, N-Me), 6.82 (1H, d, Ar—H (J=1.6 Hz)), 7.20 (1H, d, Ar—H (J=1.6 Hz)), 7.57 (1H, d, Ar—H (J=1.6 Hz)), 7.93 (1H, t, NH (J=5.6 Hz)), 8.16 (1H, d, Ar—H (J=1.6 Hz)), 10.2 (1H, s, NH).

LREIMS: Found 405.29 (M+H) calculated for C$_{18}$H$_{24}$N$_6$O$_5$ 404.18.

(v) 4-Amino-1-methyl-N-[1-methyl-5-({[2-(4-morpholinyl)ethylamino}-carbonyl)-1H-pyrrol-3-yl]-1H-pyrrole-2-carboxamide 1-Methyl-4-{[(1-methyl-4-nitro-1H-pyrrol-2-yl)carbonyl]amino}-N-[2-(4-morpholinyl)ethyl]-1H-pyrrole-2-carboxamide (150 mg, 0.371 mmol; see step (iv) above) was suspended in methanol (25 mL) to which Pd/C-10% (108 mg) was added at 0° C. under a nitrogen with stirring. The reaction mixture was hydrogenated for 5 h at room temperature and atmospheric pressure. The catalyst was removed over Kieselguhr and methanol was removed under reduced pressure to give the title compound, which was used without further purification.

Preparation 2

4-{[(4-Amino-1-methyl-1H-pyrrol-2-yl)carbonyl]amino}-N-[3-(dimethylamino)-propyl]-1-methyl-1H-pyrrole-2-carboxamide (i) N-[3-(Dimethylamino)propyl]-1-methyl-4-nitro-1H-pyrrole-2-carboxamide (See, for example, Abresia, N. G. A., Malinina, L., Subirana, J. A., *J. Mol. Biol.*, 1999, 294, 657.)

A solution of 1-methyl-4-nitro-1H-pyrrole-2-carbonyl chloride (0.254 g, 1.35 mmol; see Preparation 1(ii) above) in DCM (10 mL), is added dropwise to a solution of DMPA (0.153 g, 5.05 mmol) (Aldrich), NEt$_3$ (0.152 g, 1.5 mmol), in DCM (10 mL) over 15 min. The resulting solution was allowed to stir overnight, before quenching the reaction with a 5% NaOH solution (20 mL). The DCM fraction was then dried over MgSO$_4$, filtered and the solvent removed under reduced pressure to yield the sub-title compound (0.254 g, 74%).

m.p.=127-129° C., (lit.=125-127° C.).

IR (KBr): 1498υ(C═C), 1306, 1532 υ(N═O), 1657 υ(C═O), 2794 υ(CH$_2$), 2947 υ(Ar—H), 3126 υ(N-Me), 3284 υ(N—H) cm$^{-1}$.

$^1$H NMR (DMSO): 1.62 (2H, m, CH$_2$), 2.13 (6H, s, 2(CH$_3$)), 2.24 (2H, m, CH$_2$), 3.21 (2H, m, CH$_2$), 3.90 (3H, s, CH$_3$), 7.40 (1H, d, Ar—H (J=1.6 Hz)), 8.12 (1H, d, Ar—H (J=1.6 Hz)), 8.39 (1H, t, NH (J=5.6 Hz)).

(ii) 1-Methyl-4-{[(1-methyl-4-nitro-1H-pyrrol-2-yl)carbonyl]amino}-N-[3-(dimethylamino)propyl]-1H-pyrrole-2-carboxamide (See, for example, Abresia, N. G. A., Malinina, L., Subirana, J. A., *J. Mol. Biol.*, 1999, 294, 657.)

N-[3-(Dimethylamino)propyl]-1-methyl-4-nitro-1H-pyrrole-2-carboxamide (0.241 g, 0.95 mmol; see step (i) above) was dissolved in methanol (10 mL) and cooled to 0° C., Pd/C (55 mg) was then added in small portions and the solution stirred under H$_2$ for 3 h. The solution was then filtered and the solvent removed under reduced pressure. A solution of 1-methyl-4-nitro-1H-pyrrole-2-carbonyl chloride (0.179 g 0.95 mmol; see Preparation 1(ii) above) in DCM (10 mL) was then added and allowed to stir for 1 h at RT, the solvent was removed under reduced pressure, the crude product obtained was separated on basified silica using a 1:1 solution of methanol ethyl acetate to yield the sub-title compound (0.239 g, 67%).

m.p.=191-193° C., (lit.=190-191° C.).

$v_{max}$ KBr/cm$^{-1}$, 1498 υ(C═C), 1537, 1308 υ(N═O), 1621, 1663 υ(C═O), 2821 υ(CH$_2$), 2944 υ(Ar—H), 3140 υ(N-Me), 3287 υ(N—H).

$δ_H$ $^1$H (DMSO), 1.61 (2H, m, CH$_2$), 2.14 (6H, s, N(CH$_3$)$_2$), 2.25 (2H, m, CH$_2$), 3.18 (2H, m, CH$_2$), 6.81 (1H, d, Ar—H (J=1.6 Hz)), 7.20 (1H, d, Ar—H (J=1.6 Hz)), 7.56 (1H, d, Ar—H (J=1.6 Hz)), 8.11 (1H, t, NH (J=5.6 Hz)), 8.18 (1H, d, Ar—H (J=1.6 Hz)), 10.22 (1H, s, NH).

(iii) 4-{[(4-Amino-1-methyl-1H-pyrrol-2-yl)carbonyl]amino}-N-[3-(dimethylamino)propyl]-1-methyl-1H-pyrrole-2-carboxamide 1-Methyl-4-{[(1-methyl-4-nitro-1H-pyrrol-2-yl)carbonyl]amino}-N-[2-(4-morpholinyl)ethyl]-1H-pyrrole-2-carboxamide (150 mg, 0.371 mmol; see step (ii) above) was suspended in methanol (25 mL) to which Pd/C-10% (108 mg) was added at 0° C. under a nitrogen with stirring. The reaction mixture was hydrogenated for 5 h at room temperature and atmospheric pressure. The catalyst was removed over Kieselguhr and methanol was removed under reduced pressure to give the title compound, which was used without further purification.

Preparation 3

2-{[(4-Amino-1-methyl-1H-pyrrol-2-yl)carbonyl]amino}-N-[3-(dimethylamino)-propyl]-5-isopentyl-1,3-thiazole-4-carboxamide (i) 4-Methylpentanal To a vigorously stirred suspension of pyridinium chlorochromate (Aldrich) (50 g, 0.489 mol) in DCM (250 mL) was added a solution of 4-methylpentanol (10 g, 97.8 mol) (Aldrich) in DCM (30 mL) over a period of 45 min. The temperature rose to 35° C., and the reaction mixture turned dark brown. After a total reaction time of 6 h, ether (300 mL) was added. The resulting brown solution was passed though Florisil® (50 g, 30-60 mesh, Aldrich), and the precipitate from the ether was washed with additional amount of ether (3×30 mL), which was likewise filtered. The resulting brown solution of 4-methylpentanal was concentrated to a volume of (350 mL) and used in the next step without further purification or isolation.

(ii) Methyl 2-amino-5-isopentyl-1,3-thiazole-4-carboxylate (See, for example, Wasserman, H. H.; Petersen, A. K. and Xia, M., Tetrahedron, 2003, 59, 6771-6784).

A solution prepared from Na (3 g) and methanol (50 mL, dry) was added during 45 min to a solution of methyl dichloroacetate (20 g, 0.139 mmol) and 4-methylpentanal (see step (i) above), which was stirred vigorously at 0° C. After 1 h at 0° C. ether (50 mL) and brine were added, and the layers were collected, dried (MgSO$_4$) and the volatile solvents were removed under reduced pressure to give green liquid (16.40 g), which was dissolved in methanol (60 mL, dry) containing thiourea (8.50 g). The solution was heated under reflux for 4 h, concentrated under reduced pressure and neutralized with 18 M NH$_4$OH. Extraction with DCM gave the required product (13.50 g, crude) as light brown solid. This material was subject to a column chromatography using ethyl acetate/hexane (1/1 R$_F$=0.15). The product was recrystallized from acetone-hexane to give pale yellow crystals (7.15 g, 32%), m.p.=108-110° C. Further recrystallization from pet ether (60-80) gave the sub-title compound as white crystals.

$^1$H NMR (DMSO-d$_6$): 6.95 (2H, s), 3.70 (3H, s), 2.97 (2H, t, J=7.7 Hz), 1.53 (1H, septet, J=6.6 Hz), 1.41 (2H, q, J=7.6 Hz), 0.89 (6H, d, J=6.6 Hz).

(iii) Methyl 5-isopentyl-2-{[(1-methyl-4-nitro-1H-pyrrol-2-yl)carbonyl]amino}-1,3-thiazole-4-carboxylate 1-Methyl-4-nitro-1H-pyrrole-2-carboxylic acid (500 mg, 2.94 mmol) was suspended in thionyl chloride (5 mL) then the reaction mixture was heated under reflux for 4 h. Excess thionyl chloride was removed under reduced pressure at 50° C. and the acid chloride so formed was dissolved in DCM (5 mL, dry). Methyl 2-amino-5-isopentyl-1,3-thiazole-4-carboxylate (728 mg, 3.19 mmol; see step (ii) above) was dissolved in DCM (5 mL, dry) to which NMM (0.5 mL, dry) was added with stirring at room temperature. The acid chloride solution was added to the amine solution dropwise with stirring at room temperature and the stirring was continued overnight. The reaction mixture was extracted with KOH solution (840 mg, in water 10 mL). The organic layer was extracted with brine, dried (MgSO$_4$) and the solvent removed under reduced pressure. The crude product was applied to a column chromatography using silica gel and ethyl acetate/n-hexane as eluant (1/4), R$_F$=0.20. The sub-title compound was obtained as white solid (667 mg, 60%) after recrystallization from ethyl acetate/n-hexane, m.p.=173-175° C.

$^1$H NMR (DMSO-d$_6$): 12.81 (1H, s), 8.30 (1H, d, J=1.6 Hz), 7.99 (1H, d, J=1.6 Hz), 3.97 (3H, s), 3.80 (3H, s), 3.31 (2H, t, J=7.7 Hz), 1.58 (1H, septet, J=6.6 Hz), 1.53 (2H, q, J=7.6 Hz), 0.92 (6H, d, J=6.6 Hz).

IR (KBr): 1720, 1677, 1561, 1510, 1423, 1313, 1230, 1200, 1112 cm$^{-1}$.

HRFABMS: found: 381.1223 calculated for C$_{16}$H$_{21}$O$_5$N$_4$S 381.1233.

(iv) 5-Isopentyl-2-{[(1-methyl-4-nitro-1H-pyrrol-2-yl)carbonyl]amino}-1,3-thiazole-4-carboxylic acid Methyl 5-isopentyl-2-{[(1-methyl-4-nitro-1H-pyrrol-2-yl)carbonyl]amino}-1,3-thiazole-4-carboxylate (660 mg, 1.74 mmol; see step (iii) above) was suspended in a mixture of water (25 mL) and methanol (5 mL) containing lithium hydroxide (125 mg, 5.21 mmol). The reaction mixture was stirred vigorously for 48 h at room temperature. Some of the methanol was removed under partial reduced pressure at 50° C. The cooled solution was extracted with ether and the ethereal layer was discarded. The aqueous layer was cooled to 0° C. and acidified by adding HCl (Concentrated) dropwise with stirring. The pale yellow solid was filtered off, washed with water and dried overnight at 45° C. under reduced pressure to give the sub-title compound (584 mg, 92% yield), m.p.=296-300° C.

$^1$H NMR (DMSO-d$_6$): 12.79 (2H, br), 8.29 (1H, d, J=1.6 Hz), 7.99 (1H, d, J=1.6 Hz), 3.97 (3H, s), 3.13 (2H, t, J=7.7 Hz), 1.56 (1H, septet, J=6.6 Hz), 1.53 (2H, q, J=7.6 Hz), 0.92 (6H, d, J=6.6 Hz).

IR (KBr): 1669, 1563, 1514, 1424, 1315, 1231, 1200, 1115 cm$^{-1}$.

HRFABMS: found: 367.1068 calculated for C$_{15}$H$_{19}$O$_5$N$_4$S 367.1076.

(v) N-[3-(Dimethylamino)propyl]-5-isopentyl-2-{[(1-methyl-4-nitro-1H-pyrrol-2-yl)carbonyl]amino}-1,3-thiazole-4-carboxamide 5-Isopentyl-2-{[(1-methyl-4-nitro-1H-pyrrol-2-yl)carbonyl]amino}-1,3-thiazole-4-carboxylic acid (570 mg, 1.56 mmol; see step (iv) above) was dissolved in DMF (2.5 mL, dry) to which NMM (0.5 mL, dry), HBTU (1.18 g, 3.12 mmol) and dimethylaminopropylamine (318 mg, 3.12 mmol, Aldrich) were added at room temperature with stirring. After the standard work up and purification, the sub-title compound was obtained as a yellow solid (660 mg, 94%), m.p.>230° C.

$^1$H NMR (DMSO-d$_6$): 8.31 (1H, d, J=1.6 Hz), 7.96 (1H, d, J=1.6 Hz), 3.98 (3H, s), 3.33 (2H, q, J=6.4 Hz), 3.19 (2H, t, J=7.7 Hz), 2.62 (3H, s), 1.84 (2H, quintet, J=7.7 Hz), 1.57 (1H, septet, J=6.7 Hz), 1.51 (2H, q, J=6.5 Hz), 0.91 (6H, d, J=6.3).

IR (KBr): 1674, 1642, 1561, 1502, 1421, 1310, 1120 cm$^{-1}$.

HRFABMS: found: 451.2125 calculated for C$_{20}$H$_{31}$O$_4$N$_6$S 451.2127.

(vi) 2-{[(4-Amino-1-methyl-1H-pyrrol-2-yl)carbonyl]amino}-N-[3-(dimethylamino)propyl]-5-isopentyl-1,3-thiazole-4-carboxamide N-[3-(Dimethylamino)propyl]-5-isopentyl-2-{[(1-methyl-4-nitro-1H-pyrrol-2-yl)carbonyl]amino}-1,3-thiazole-4-carboxamide (265 mg, 0.588 mmol; see step (v) above) was suspended in methanol (25 mL) to which Pd/C-10% (300 mg) was added at 0° C. under a nitrogen with stirring. The reaction mixture was hydrogenated for 3 h at room temperature and atmospheric pressure. The catalyst was removed over Kieselguhr and methanol was removed under reduced pressure to give the title compound, which was used without further purification.

Preparation 4

4-[(E)-2-(3-Methoxyphenyl)ethenyl]benzoic acid

(i) Methyl 4-[(diethoxyphosphoryl)methyl]benzoate (See, for example, *Tetrahedron*, 2002, 58, 1425-1432.)

A mixture of methyl 4-(bromomethyl)benzoate (2.50 g, 10.9 mmol) and triethylphosphite (3.62 g, 21.8 mmol, 2 molar equivalent) was heated at 160° C. under a nitrogen atmosphere for 2 h. The excess triethylphosphite was removed in vacuo to give the sub-title compound as colourless oil (3.03 g, 97%).

$^1$H NMR (DMSO-$d_6$): 7.91 (2H, d, J=8.0 Hz), 7.44 (2H, dd, J=2.4 Hz & J=8.4 Hz), 4.00 (4H, quintet, J=6.8 Hz), 3.84 (3H, s), 3.36 (2H, d, J=22.0 Hz), 1.16 (6H, t, J=6.8 Hz).

(ii) Methyl 4-[(E)-2-(3-methoxyphenyl)ethenyl]benzoate

To a solution of Methyl 4-[(diethoxyphosphoryl)methyl]benzoate (3.03 g, 10.6 mmol; see step (i) above) in THF (10 mL, dry) under a nitrogen atmosphere was added sodium hydride (0.678 g, 60%, 18.8 mmol). After cooling the reaction mixture to 0° C., m-anisaldehyde (1.54 g, 11.3 mmol in THF 20 mL, dry) was carefully added dropwise with stirring. The reaction mixture was stirred for 1 h at room temperature and then quenched with water. After neutralisation with dilute HCl, the two layers were separated. The water layer was extracted with ethyl acetate and the organic layers were combined, dried (MgSO$_4$), filtered and the solvent removed under reduced pressure to give white a solid. TLC showed two spots ($R_F$=0.80 and $R_F$=0.10, 20% ethyl acetate/n-hexane). The two compounds were separated using silica gel column chromatography (20% ethyl acetate/n-hexane).

The first fraction was methyl 4-[(E)-2-(3-methoxyphenyl)ethenyl]-benzoate (1.57 g, 55%), isolated as a white solid, m.p.=92-94° C.

$^1$H NMR (DMSO-$d_6$): 7.96 (2H, d, J=8.4 Hz), 7.74 (2H, d, J=8.4 Hz), 7.42-7.21 (4H, m), 6.88 (1H, m), 3.85 (3H, s), 3.80 (3H, s).

IR (KBr): 1708, 1595, 1438, 1280, 1244, 1174, 1105, 1033, 965, 865, 784, 697 cm$^{-1}$.

HREIMS: found 268.1100 calculated for $C_{17}H_{16}O_3$ 268.1099.

(iii) 4-[(E)-2-(3-Methoxyphenyl)ethenyl]benzoic acid

In line with step (ii) above, the second fraction isolated using silica gel column chromatography (20% ethyl acetate/n-hexane) was 4-[(E)-2-(3-methoxyphenyl)ethenyl]benzoic acid (0.250 g, 9%), isolated as a white solid, m.p.=200-205° C.

$^1$H NMR (DMSO-$d_6$): 12.88 (1H, br), 7.94 (2H, d, J=8.4 Hz), 7.72 (2H, d, J=8.4 Hz), 7.37 (2H, d, J=3.6 Hz), 7.31 (1H, t, J=8.0 Hz), 7.22 (2H, m), 6.88 (1H, m), 3.80 (3H, s).

IR (KBr): 1674, 1596, 1429, 1317, 1280, 1242, 1180, 1036, 948, 849, 770 cm$^{-1}$.

HREIMS: 254.0945 calculated for $C_{16}H_{14}O_3$ 254.0977.

Preparation 5

4-[(E)-2-(3-Quinolinyl)ethenyl]benzoic acid

(i) Methyl 4-[(E)-2-(3-quinolinyl)ethenyl]benzoate

To a solution of methyl 4-[(diethoxyphosphoryl)methyl]benzoate (0.911 g, 3.18 mmol; see Preparation 4(i) above) in THF (10 mL, dry) under a nitrogen atmosphere was added sodium hydride (0.678 g, 60%, 18.8 mmol). After cooling the reaction mixture to 0° C., quinoline-3-aldehyde (0.500 g, 3.18 mmol) in THF (10 mL, dry) was carefully added dropwise with stirring. The reaction mixture was stirred for 1 h at room temperature and then quenched with water. After neutralisation with dilute HCl, the two layers were separated, the water layer extracted with ethyl acetate and the organic layers were combined, dried (MgSO$_4$), filtered and the solvent removed under reduced pressure to give a white solid. The product was purified by silica gel column chromatography using 25% ethyl acetate/n-hexane ($R_F$=0.50) to give the sub-title compound (0.900 g, 98%), as a white solid, m.p.=92-94° C.

$^1$H NMR (DMSO-$d_6$): 9.25 (2H, d, J=2.0 Hz), 8.54 (2H, d, J=2.0 Hz), 8.01 (2H, m), 7.82 (2H, d, J=8.4 Hz), 7.75 (1H, t, J=6.8 Hz), 7.64 (2H, d, J=3.6 Hz), 7.63 (1H, t, J=8.1 Hz), 3.87 (3H, s).

IR (KBr): 1716, 1598, 1460, 1273, 1173, 750 cm$^{-1}$.

HREIMS: found: 289.1104 calculated for $C_{19}H_{15}NO_2$ 289.1103.

(ii) 4-[(E)-2-(3-Quinolinyl)ethenyl]benzoic acid

Methyl 4-[(E)-2-(3-quinolinyl)ethenyl]benzoate (0.840 mg, 3.36 mmol; see step (i) above) was suspended in methanol (10 mL) and water (20 mL) to which sodium hydroxide solution (NaOH 0.580 g, 14.5 mmol in water 10 mL) was added with stirring. The reaction mixture was heated under reflux for 2 h. At the beginning the starting material dissolved then white precipitate appeared. The reaction mixture was cooled in an ice bath then (dilute HCl was added dropwise with vigorous stirring until pH 2 was attained. The title compound formed as a yellow solid material, which was filtered off, washed with water and dried in vacuo at 60° C. (0.640 g, 69%), m.p.=287-290° C.

$^1$H NMR (DMSO-$d_6$): 12.91 (1H, br), 9.25 (1H, d, J=2.1 Hz), 8.54 (1H, d, J=2.1 Hz), 8.03-7.97 (4H, m), 7.69-7.59 (3H, m).

IR (KBr): 1694, 1586, 1541, 1423, 1310, 1272, 1172, 962, 767, 687 cm$^{-1}$.

HREIMS: found: 275.0948 calculated for $C_{18}H_{13}NO_2$ 275.0946.

Preparation 6

4-[(E)-2-(1-Methyl-1H-pyrrol-2-yl)ethenyl]benzoic acid, lithium salt (i) Methyl 4-[(f)-2-(1-methyl-1H-pyrrol-2-yl)ethenyl]benzoate To a solution of methyl 4-[(diethoxyphosphoryl)methyl]benzoate (0.820 g, 2.86 mmol; see Preparation 4(i) above) in THF (10 mL, dry) under a nitrogen atmosphere was added sodium hydride (0.573 g, 60%, 14.3 mmol). After cooling the reaction mixture to 0° C., N-methylpyrrole-2-aldehyde (0.312 g, 2.86 mmol) in THF 10 mL, dry) was carefully added dropwise with stirring. The reaction mixture was stirred for 1 h at room temperature and then quenched with water. After neutralisation with dilute HCl, the two layers were separated. The water layer was extracted with ethyl acetate and the organic layers were combined, dried ($MgSO_4$), filtered and the solvent removed under reduced pressure to give yellow solid. The product was purified by alumina column chromatography using 2% ethyl acetate/n-hexane ($R_F$=0.20) and gradually increased to 10% to give the sub-title compound (0.140 g, 20%), as a yellow solid, m.p.=95-98° C.

$^1$H NMR (DMSO-$d_6$): 7.91 (2H, d, J=8.4 Hz), 7.68 (2H, d, J=8.0 Hz), 7.35 (1H, d, J=16.4 Hz), 6.95 (1H, d, J=16.4 Hz), 6.83 (1H, t, J=2.0 Hz), 6.56 (1H, dd, J=1.5 Hz & J=3.7 Hz), 6.06 (1H, t, J=3.1 Hz), 3.84 (3H, s), 3.71 (3H, s).

IR (KBr): 1704, 1597, 1420, 1270, 1175, 1107, 955, 767, 745 cm$^{-1}$.

HREIMS: found: 241.1106 calculated for $C_{15}H_{15}NO_2$ 241.1103.

(ii) 4-[(E)-2-(1-Methyl-1H-pyrrol-2-yl)ethenyl]benzoic acid lithium salt

Methyl 4-[(E)-2-(1-methyl-1H-pyrrol-2-yl)ethenyl]benzoate (40 mg, 0.166 mmol; see step (i) above) was suspended in a mixture of methanol (1 mL) and lithium hydroxide solution (16 mg of LiOH in water 2 mL). The reaction mixture was heated at 60° C. overnight with stirring. This solution was freeze-dried and the title compound used in the next step without further purification.

Preparation 7

3-[(E)-2-(3-Methoxyphenyl)ethenyl]benzoic acid (i) 3-[(Diethoxyphosphoryl)methyl]benzoate A mixture of methyl 3-(bromomethyl)benzoate (2.51 g, 10.9 mmol) and triethylphosphite (3.62 g, 21.8 mmol, 2 molar equivalent) was heated at 160° C. under a nitrogen atmosphere for 2 h. The excess triethylphosphite was removed in vacuo to give the sub-title compound as a colourless oil (3.03 g, 97%).

$^1$H NMR (DMSO-$d_6$): 7.91 (1H, s), 7.84 (1H, d, J=6.7 Hz), 7.56 (1H, d, J=6.7 Hz), 7.46 (1H, t, J=8.0 Hz), 4.00 (4H, quintet, J=6.8 Hz), 3.85 (3H, s), 3.36 (2H, d, J=22.0 Hz), 1.16 (6H, t, J=6.8 Hz).

IR (KBr): 1722, 1590, 1442, 1289, 1251, 1197, 1103, 1035, 966, 847, 803, 753 cm$^{-1}$.

HREIMS: Found: 296.1179 calculated for $C_{15}H_{21}O_4P$ 296.1177.

(ii) Methyl-3-[(E)-2-(3-methoxyphenyl)ethenyl]benzoate

To a solution of methyl 3-[(diethoxyphosphoryl)methyl]benzoate (1.02 g, 3.56 mmol; see step (i) above) in THF (5 mL, dry) under a nitrogen atmosphere was added sodium hydride (0.212 g, 60%, 18.8 mmol). After cooling the reaction mixture to 0° C., m-anisaldehyde (0.485 g, 3.56 mmol) in THF 10 mL, dry) was carefully added dropwise with stirring. The reaction mixture was stirred for 1 h at room temperature and then quenched with water. After neutralisation with dilute HCl, the two layers were separated. The water layer was extracted with ethyl acetate and the organic layers were combined, dried ($MgSO_4$), filtered and the solvent removed under reduced pressure. The product was purified using silica gel column chromatography ($R_F$=0.80 20% ethyl acetate/n-hexane) to give the sub-title compound as a white solid (0.747 g, 78%), m.p.=92-94° C.

$^1$H NMR (DMSO-$d_6$): 8.16 (1H, s), 7.91 (1H, d, J=8.1 Hz), 7.86 (1H, d, J=8.1 Hz), 7.55-7.20 (6H, m), 6.87 (1H, dd, J=1.7 Hz & J=8.0 Hz), 3.88 (3H, s), 3.80 (3H, s).

IR (KBr): 1710, 158, 1467, 1440, 1267, 1161, 792, 744, 686 cm$^{-1}$.

HREIMS: found: 268.1101 calculated for $C_{17}H_{16}O_3$ 268.1099.

(iii) 3-[(E)-2-(3-Methoxyphenyl)ethenyl]benzoic acid

Methyl-3'-[(E)-2-(3-methoxyphenyl)ethenyl]benzoate (0.740 mg, 2.75 mmol; see step (ii) above) was suspended in methanol (10 mL) and water (20 mL) to which lithium hydroxide solution (LiOH 0.199 g, 8.27 mmol in water 10 mL) was added with stirring. The reaction mixture was heated under reflux for 4 h. The reaction mixture was cooled in an ice bath then dilute HCl was added dropwise with vigorous stirring until pH 2 was attained. The product as a white solid material was filtered off, washed with water and dried in vacuo at 60° C. to give the title compound (0.235 g, 34%), m.p.=195-198° C.

$^1$H NMR (DMSO-$d_6$): 8.12 (1H, s), 7.78 (1H, d, J=7.6 Hz), 7.63 (1H, d, J=7.6 Hz), 7.37-7.18 (7H, m), 6.83 (1H, dd, J=1.7 Hz & J=8.0 Hz), 3.80 (3H, s).

IR (KBr): 1684, 1586, 1541, 1423, 1310, 1272, 961, 767, 687 cm$^{-1}$.

HREIMS: found: 254.0935 calculated for $C_{16}H_{14}O_3$ 254.0943.

Preparation 8

1-Methyl-4-[(E)-2-(4-nitrophenyl)ethenyl]-1H-pyrrole-2-carboxylic acid (i) Diethyl 4-nitrobenzylphosphonate A mixture of 4-nitrobenzyl bromide (2.05 g, 0.949 mmol) and triethylphosphite (2.23 g, 1.34 mmol) was heated at 160° C. under a nitrogen atmosphere for 2 h. The excess triethylphosphite was removed in vacuo to give the sub-title compound as a brown oil (2.50 g, 96%).

$^1$H NMR (DMSO-$d_6$): 8.20 (2H, d, J=8.1 Hz), 7.57 (2H, dd, J=2.4 Hz & J=8.8 Hz), 3.97 (4H, q, J=7.0 Hz), 3.48 (2H, d, J=22.4 Hz), 1.18 (6H, t, J=7.0 Hz).

IR (KBr): 2982, 2910, 1601, 1521, 1392, 1347, 1254, 1028, 959, 864, 777, 695 cm$^{-1}$.

HREIMS: Found 273.0765 calculated for $C_{11}H_{16}O_5NP$ 273.0766.

(ii) Ethyl-1-methyl-4-[(E)-2-(4-nitrophenyl)ethenyl]-1H-pyrrole-2-carboxylate

To a solution of diethyl 4-nitrobenzylphosphonate (0.525 g, 1.92 mmol; see step (i) above) in THF (5 mL, dry) under a nitrogen atmosphere was added sodium hydride (0.115 g, 60%, 2.88 mmol). After cooling the reaction mixture to 0° C., ethyl 4-formyl-1-methyl-1H-pyrrole-2-carboxylate (0.348 g, 1.92 mmol) in THF 10 mL, dry) was carefully added dropwise with stirring. The reaction mixture was stirred for 1 h at room temperature and then quenched with water. After neutralisation with dilute HCl, the two layers were separated. The water layer was extracted with ethyl acetate and the organic layers were combined, dried (MgSO$_4$), filtered and the solvent removed under reduced pressure. The yellow solid was collected and triturated with warm methanol to give a yellow solid (288 mg). The mother liquor was collected and purified using silica gel column chromatography ($R_F$=0.50 50% ethyl acetate/n-hexane) to give an additional material (100 mg). The sub-title compound was isolated as a yellow solid (0.388 g, 40%), m.p.=165-168° C.

NMR (DMSO-d$_6$): 8.19 (2H, d, J=8.8 Hz), 7.73 (2H, d, J=8.8 Hz), 7.40 (1H, d, J=1.5 Hz), 7.34 (1H, d, J=16.3 Hz), 7.20 (1H, d, J=1.5 Hz), 7.09 (1H, d, J=16.3 Hz), 4.26 (2H, q, J=7.1 Hz), 3.87 (3H, s), 1.28 (3H, t, J=7.1 Hz).

IR (KBr): 1680, 1632, 1588, 1546, 1508, 1338, 1249, 1142, 1101, 980, 849, 760 cm$^{-1}$.

HREIMS: found 300.1111 calculated for $C_{16}H_{16}O_4N_2$ 300.1110.

(iii) 1-Methyl-4-[(E)-2-(4-nitrophenyl)ethenyl]-1H-pyrrole-2-carboxylic acid

Ethyl-1-methyl-4-[(E)-2-(4-nitrophenyl)ethenyl]-1H-pyrrole-2-carboxylate (0.100 mg, 0.333 mmol; see step (ii) above) was suspended in ethanol (4 mL), THF (8 mL) and water (20 mL) to which sodium hydroxide solution (NaOH 0.190 g, 4.75 mmol in water 10 mL) was added with stirring. The reaction mixture was heated under reflux for 4 h. The reaction mixture was cooled to room temperature then HCl$_{(conc.)}$ was added dropwise with vigorous stirring until pH 2 was attained. The yellow, solid material was filtered off, washed with water and dried in vacuo at 60° C. to provide the title compound (50 mg, 55%), m.p.=212-215° C. (decomposition).

$^1$H NMR (DMSO-d$_6$): 12.37 (1H, br), 8.18 (2H, d, J=8.8 Hz), 7.72 (2H, d, J=8.8 Hz), 7.36 (1H, d, J=1.5 Hz), 7.34 (1H, d, J=16.3 Hz), 7.15 (1H, d, J=1.5 Hz), 7.04 (1H, d, J=16.3 Hz), 3.86 (3H, s).

IR (KBr): 1671, 1634, 1588, 1505, 1449, 1337, 1281, 1255, 1184, 1145, 1105, 833, 802, 742, 688 cm$^{-1}$.

HREIMS: found 272.0795 calculated for $C_{14}H_{12}O_4N_2$ 272.0797.

Preparation 9

4-[(E)-2-(4-Pyridinyl)ethenyl]benzoic acid

4-Carboxybenzaldehyde (2.03 g, 13.3 mmol, Aldrich) and 4-picoline (1.24 g, 13.3 mmol, Aldrich) were placed in a round-bottomed flask, to which a 20 mL of acetic anhydride was added. The reaction mixture was heated to reflux for 24 h. The solid was filtered and the solid was washed with acetic acid then with water before being dried in vacuo, at 50° C. overnight to give the title compound as an offwhite solid (426 mg, 14%).

$^1$H NMR (DMSO-d$_6$): 7.40 (1H, d, J=16 Hz), 7.60 (2H, d, J=6 Hz), 7.62 (1H, d, J=16 Hz), 7.77 (2H, d, J=8 Hz), 7.97 (2H, d, J=8 Hz), 8.57 (2H, d, J=6 Hz), 10.0 (1H, s).

IR (KBr): 1606, 1690, 2995 cm$^{-1}$.

HRFABMS: Found 226.2424 calculated for $C_{14}H_{11}NO_2$ 225.2426.

Preparation 10

Diethyl (1-methyl-4-nitro-1H-pyrrol-2-yl)methylphosphonate (i) 1-Methyl-4-nitro-1H-pyrrole-2-carbaldehyde (See, for example, Suckling, C. J., Khalaf, A. I., Pitt A. R., Scobie, M., *Tetrahedron*, 2000, 56, 5225.)

HNO$_3$ (70%) (1.6 mL) was added dropwise to acetic anhydride (8 mL) at –25° C., and allowed to stir for a further 20 min. This solution was added dropwise to a solution of 1-methylpyrrole-2-carboxaldehyde (Aldrich) (1.74 g, 15.96 mmol), in acetic anhydride (12 mL) at –25° C. and allowed to return to RT over 2 h. The solution was cooled to –40° C., at which point a precipitate formed. The precipitate was collected and washed with hexane and then dried under reduced pressure to the sub-title compound (0.540 g, 22%).

m.p.=157-159° C., (Lit=158-160° C.).

$^1$H NMR (CDCl$_3$): 4.04 (3H, s, CH$_3$), 7.43 (1H, d, Ar—H, J=1.6 Hz), 7.68 (1H, d, Ar—H, J=1.6 Hz).

IR (KBr): 3139 υ(N-Me), 3125 υ(Ar—H), 2958 υ(C—H (COH)), 1671υ(C=O), 1504, 1311 υ(N=O) cm$^{-1}$.

Anal. Calcd. For $C_6H_6O_3N_2$ C, 46.76; H, 3.92; N, 18.18; O, 31.14. Found: C, 46.29; H, 3.68; N, 17.47.

(ii) (1-Methyl-4-nitro-1H-pyrrol-2-yl)methanol

1-Methyl-4-nitro-1H-pyrrole-2-carbaldehyde (0.400 g, 2.08 mmol; see step (i) above) was placed in 50 mL of anhydrous ethanol under N$_2$. NaBH$_4$ (0.040 g, 1.04 mmol) was added in small portions over 5 min and the solution allowed to stir for 20 min. Water (10 mL) was added slowly to quench the reaction. The organics were then extracted with ethyl acetate (2×20 mL) and the resultant organic fractions dried (MgSO$_4$), filtered and the solvent removed under reduced pressure to yield the sub-title compound as a light brown solid (0.318 g, 98%).

m.p.=89-90° C., (Lit=90.5-91.5° C.).

IR (KBr): 3521 υ(O—H), 3131 υ(N-Me), 2934, 2888 υ(Ar—H), 1490, 1412 υ(C=C), 1520, 1337 υ(N=O) cm$^{-1}$.

$^1$H NMR (CDCl$_3$): 3.67 (3H, s, N-Me), 4.40 (2H, d, CH$_2$, J=5.4 Hz), 5.18 (1H, t, OH, J=3.0 Hz), 6.57 (1H, d, Ar—H, J=1.6 Hz)), 7.92 (1H, d, Ar—H, J=1.6 Hz).

(iii) Diethyl (1-methyl-4-nitro-1H-pyrrol-2-yl)methylphosphonate (1-Methyl-4-nitro-1H-pyrrol-2-yl)methanol (0.100 g, 0.64 mmol; see step (ii) above) was taken up in DCM (5 mL), and SOCl$_2$ (5 mL) added slowly, the solution was then refluxed for 15 min and the excess SOCl$_2$ was removed under reduced pressure. The residue was heated in P(OEt)$_3$ (3 mL) for 1 h at 160° C. and the excess P(OEt)$_3$ was then removed under high vacuum (1.5 mmHg @ 70° C.) to furnish the title compound initially as a brown oil, which solidified after 48 h at 0-4° C. to a brown crystalline solid (0.173 g, 98%).

IR (NaCl): 3137 υ(N-Me), 2985 υ(Ar—H), 1556, 1438 υ(C=C), 1519, 1346 υ(N=O), 1308 υ(P=O), 1163 δ(P—O—C) cm$^{-1}$.

$^1$H NMR (CDCl$_3$): 1.20 (6H, t, CH$_3$, J=6.8 Hz), 3.08 (2H, d, (CH$_2$)P, J=20.4 Hz), 3.65 (3H, s, N-Me), 4.01 (4H, q, (CH$_2$)CH$_3$, J=6.8 Hz), 6.54 (1H, d, Ar—H, J=1.6 Hz), 7.39 (1H, d, Ar—H, J=1.6 Hz), $\delta_P$ $\delta^{31}$P (CDCl$_3$), 23.44.

HRFABMS: Found 276.0875 calculated for $C_{10}H_{17}N_2O_5P$ 276.0873

Preparation 11

Ethyl 4-formyl-1-methyl-1H-pyrrole-2-carboxylate

(i) 2-Trichloroacetyl-N-methylpyrrole (See, for example, Suckling, C. J., Khalaf, A. I., Pitt A. R., Scobie, M., *Tetrahedron*, 2000, 56, 5225.)

Trichloroacetylchloride (36.2 g, 200.65 mmol) in DCM (130 mL) was placed in a round bottom flask at room temperature under $N_2$. A solution of N-methylpyrrole (16.2 g, 200.32 mmol) (Aldrich) in DCM (70 mL) was then added dropwise over 2.5 h and the solution allowed to stir overnight. The solvent was then removed under reduced pressure to yield the crude product, which was filtered through a silica column using DCM as eluent to yield the sub-title compound as a yellow solid (31.690 g, 70%).

m.p.=62-64° C., (Lit=64-65° C.).

IR (KBr): 3137, 3119 υ(N-Me), 3005, 2952 υ(C—H), 1655 υ(C=O), 1238, 1124 υ(C—O), 742 δ(C—H) $cm^{-1}$.

$^1$H NMR ($CDCl_3$): 3.98 (3H, s, $CH_3$), 6.23 (1H, dd, Ar—H, J=2.6 Hz & J=3.9 Hz), 5.97 (1H, d, Ar—H, J=1.6 Hz), 7.51 (1H, q, Ar—H, J=7.2 Hz), $^{13}$C($CDCl_3$): 38.68 ($CH_3$), 96.52 ($CCl_3$), 109.07 (C), 122.02 (C—H), 124.18 (C—H), 133.80 (C—H), 173.04 (C=O).

(ii) Ethyl 1-methyl-1H-pyrrole-2-carboxylate (See, for example, Suckling, C. J., Khalaf, A. I., Pitt A. R., Scobie, M., *Tetrahedron*, 2000, 56, 5225.)

2-Trichloroacetyl-N-methylpyrrole (1.47 g, 6.51 mmol; see step (i) above) and EtOH (20 mL) was placed in a round bottom flask, to which NaOEt (0.33 g, 6.52 mmol) was added and the resultant mixture was heated to reflux and stirred for 1 h. The reaction was quenched with water (10 mL) and extracted with DCM (2×20 mL). The DCM fractions where combined, dried ($MgSO_4$), and reduced under vacuum to yield the sub-title compound as a yellow oil (0.926 g, 93%).

IR (KBr), 3136 υ(N-Me), 2980 υ(C—H), 1713υ(C=O), 1244, 1114 υ(C—O), 599 δ(C—H) $cm^{-1}$.

$^1$H NMR ($CDCl_3$): 1.35 (3H, t, $CH_2(CH_3)$, J=7.2 Hz), 3.93 (3H, s, $CH_3$), 4.27 (2H, q, $CH_2$, J=7.2 Hz), 6.11 (1H, dd, Ar—H, J=2.6 Hz & J=4.0 Hz), 6.78 (1H, t, $CH_2$, J=2.1 Hz), 6.94 (1H, dd, Ar—H, J=2.6 Hz & J=4.0 Hz).

(iii) Ethyl 4-formyl-1-methyl-1H-pyrrole-2-carboxylate

Ethyl 1-methyl-1H-pyrrole-2-carboxylate (3.69 g, 28.24 mmol; see step (ii) above) and $AlCl_3$ (8.02 g, 60.11 mmol) were added to a solution of nitromethane (40 mL), and 1,2-dichloroethane (40 mL) at −30° C. Dichloromethyl methyl ether (2.5 mL, 28 mmol) in 1,2-dichloroethane (10 mL) was added rapidly to the solution and the mixture was allowed to stir at −30° C. for 16 h. The solution was then poured onto ice (50 g) and the layers were separated. The aqueous layer was then extracted with ether (50 mL). The combined organic fractions were dried ($MgSO_4$), filtered and the solvent removed under reduced pressure, to yield the title compound as a crystalline brown/black solid (4.77 g, 94%).

m.p.=69-71° C., (Lit=66-68° C.).

IR (NaCl): 3129 υ(N-Me), 2981 υ(Ar—H), 2767, 2719 υ(C—H(CHO)), 1676 υ(C=O), 1541, 1500, 1471 υ(C=C) 1260, 1210 υ(C—O), 1437 δ($CH_3$, $CH_2$) $cm^1$.

$^1$H NMR ($CDCl_3$): 1.36 (3H, t, $CH_2(CH_3)$, J=7.2 Hz), 3.98 (3H, s, N-Me), 4.32 (2H, q, ($CH_2$)$CH_3$, J=7.2 Hz), 7.37 (2H, m, 2(Ar—H)), 9.76 (1H, s, CO(H)).

Preparation 12

1-Methyl-4-[(E)-2-(3-quinolinyl)ethenyl]-1H-pyrrole-2-carboxylic acid

(i) 3-Quinolinylmethanol

3-Quinolinecarbaldehyde (Aldrich) (1.04 g, 6.64 mmol) was dissolved in anhydrous ethanol (20 mL), $NaBH_4$ (0.250 g, 3.95 mmol) was then added in small portions over 10 min and the resulting solution allowed to stir for a further 30 min. Water (20 mL) was then added and the resulting solution extracted with ethyl acetate (2×30 mL). The combined organics were dried ($MgSO_4$), filtered and the solvent removed under reduced pressure to give the sub-title compound.

(ii) 3-(Chloromethyl)quinolinium chloride

3-Quinolinylmethanol (that prepared step (i) above) was dissolved in DCM (2 mL) and $SOCl_2$ (5 mL) was added (dropwise initially) to the solution, which was then refluxed for 1 h. The DCM and excess $SOCl_2$ were then removed under reduced pressure to yield the sub-title compound, which was employed directly in the next step without further purification.

(iii) Diethyl 3-quinolinylmethylphosphonate 3-(Chloromethyl)quinolinium chloride (that prepared in step (ii) above) was dissolved in water (5 mL) and washed with $NaCO_3$ (1M), the aqueous phase was then extracted with ethyl acetate (2×15 mL). The combined organics were dried over $MgSO_4$ and the solvent removed under reduced pressure. The residue was then dissolved in $POEt_3$ (3 mL) and the solution refluxed for 1 h. The excess $POEt_3$ was then removed under high vacuum to yield the sub-title compound as a viscous orange oil (1.816 g, 98%).

$ν_{max}$ KBr/$cm^{-1}$, 3056, 2982, 2931, 2907 υ(C—H), 1606 υ(C=N), 1571, 1495, 1443 υ(C=C), 1253 υ(P=O), 1052 δ(P—O—C).

$δ_H$ $^1$H($CDCl_3$), 1.25 (6H, m, 2($CH_3$)), 3.30 (2H, d, $CH_2$ (J=21.9 Hz)), 4.06 (4H, m, 2($CH_2$)), 7.55 (1H, t, Ar—H (J=7.2 Hz)), 7.70 (1H, t, Ar—H (J=7.2 Hz)), 7.81 (1H, d, Ar—H (J=8.0 Hz)), 8.09 (1H, d, Ar—H (J=8.0 Hz)), 8.12 (1H, s, Ar—H), 8.81 (1H, s, Ar—H), $δ_p$ $δ^{31}$P ($CDCl_3$), 25.77.

LREIMS: Found 280.10 (M+H) calculated for $C_{14}H_{18}NO_3P$ 279.10

(iv) Ethyl 1-methyl-4-[(E)-2-(3-quinolinyl)ethenyl]-1H-pyrrole-2-carboxylate 3-Quinolinylmethylphosphonate (0.503 g, 1.93 mmol; see step (iii) above) was dissolved in anhydrous THF (2 mL) and NaH (0.273 g, 11.37 mmol) was then added in small portions to the solution and the resulting mixture was then aged for an additional 10 min. Ethyl 4-formyl-1-methyl-1H-pyrrole-2-carboxylate (0.313 g, 1.92 mmol; see Preparation 11 above) in anhydrous THF (3 mL) was added dropwise and the solution allowed to stir for 16 h. Water (5 mL) was added to the mixture (dropwise initially) during which time the sub-title compound precipitated as a yellow solid (0.201 g, 34%).

m.p.=134-137° C.

$\nu_{max}$ KBr/cm$^{-1}$, 3001, 2924 υ(C—H), 2854 υ(N-Me) 1699 υ(C=O), 1636 υ(C=C alkene), 1600 1546, 1494, 1436 υ(C=C), 1367 δ(C—H).

$\delta_H$ $^1$H(CDCl$_3$), 1.30 (3H, t, CH$_3$ (J=7.2 Hz)), 3.88 (3H, s, N—CH$_3$), 4.25 (2H, q, CH$_2$ (J=7.0 Hz)), 7.08 (1H, d, C=C (J=16.4 Hz)), 7.19 (1H, d, Ar—H (J=1.6 Hz)), 7.35 (2H, m, Ar—H), 7.58 (1H, t, Ar—H (J=7.2 Hz)), 7.68 (1H, t, Ar—H (J=7.2 Hz)), 7.92 (1H, d, Ar—H (J=8.0 Hz)), 7.97 (1H, d, Ar—H (J=8.0 Hz)), 8.32 (1H, s, Ar—H), 9.10 (1H, d, Ar—H (J=2.0 Hz)).

HRFABMS: Found 306.1371 calculated for C$_{19}$H$_{18}$N$_2$O$_2$ 306.1368.

(v) 1-Methyl-4-[(E)-2-(3-quinolinyl)ethenyl]-1H-pyrrole-2-carboxylic acid

Ethyl 1-methyl-4-[(E)-2-(3-quinolinyl)ethenyl]-1H-pyrrole-2-carboxylate (0.137 g, 0.44 mmol; see step (iv) above) was suspended in ethanol (2 mL) and NaOH (0.052 g, 1.32 mmol) in water (5 mL) was added to the solution and the resultant mixture was refluxed for 2 h. The reaction was filtered while hot and then cooled to 0° C. Dilute HCl was then added dropwise until the title compound precipitated as a yellow solid (0.076 g, 62%).

m.p.>230° C.

$\nu_{max}$ KBr/cm$^{-1}$: 3462 υ(O—H), 2982 υ(N-Me), 2824 υ(Ar—H), 2854 υ(N-Me) 1685 υ(C=O), 1639 υ(C=C alkene), 1603 1552, 1494 υ(C=C).

$\delta_H$ $^1$H (DMSO): 3.86 (3H, s, N—CH$_3$), 6.78 (1H, d, Ar—H (J=1.6 Hz)), 6.88 (1H, d, C=C alkene (J=16.4 Hz)), 6.97 (1H, d, Ar—H (J=1.6 Hz)), 7.30 (1H, d, C=C Alkene (J=16.4 Hz)), 7.56 (1H, t, Ar—H (J=7.2 Hz)), 7.65 (1H, d, Ar—H (J=7.2 Hz)), 7.90 (1H, d, Ar—H (J=8.0 Hz)), 7.95 (1H, d, Ar—H (J=8.0 Hz)), 8.28 (1H, s, Ar—H), 9.08 (1H, s, Ar—H).

HRFABMS: Found 278.1054 calculated for C$_{17}$H$_{14}$N$_2$O$_2$ 278.1055.

Preparation 13

1-Methyl-4-[(E)-2-(2-quinolinyl)ethenyl]-1H-pyrrole-2-carboxylic acid

(i) Diethyl 2-quinolinylmethylphosphonate

The sub-title compound was prepared according to a procedure analogous to that described in Preparation 12(iii) above, using 2-(chloromethyl)quinolinium chloride in place of 3-(chloromethyl)quinolinium chloride.

Yield=1.790 g, 97%.

$\nu_{max}$ KBr/cm$^{-1}$, 3059, 2982, 2930, 2907 υ(C—H), 1618 υ(C=N), 1599, 1562, 1478, 1442 υ(C=C), 1254 υ(P=O), 1027 δ(P—O—C).

$\delta_H$ $^1$H(CDCl$_3$), 1.26 (6H, m, 2(CH$_3$)), 3.67 (2H, d, CH$_2$ (J=22.4 Hz)), 4.11 (4H, m, 2(CH$_2$)), 7.52 (2H, m, Ar—H), 7.70 (1H, t, Ar—H (J=7.2 Hz)), 7.81 (1H, d, Ar—H (J=8.0 Hz)), 8.05 (1H, d, Ar—H (J=8.0 Hz)), 8.12 (1H, d, Ar—H (J=8.0 Hz)), $\delta_P$ $\delta^{31}$P (CDCl$_3$), 25.35.

HRFABMS: Found 280.1098 (M+H) calculated for C$_{14}$H$_{18}$NO$_3$P 279.1024.

(ii) Triphenyl(2-quinolinylmethyl)phosphonium chloride 2-(Chloromethyl)quinolinium chloride (0.669 g, 1.52 mmol) (Aldrich) was dissolved in water (5 mL) and washed with Na$_2$CO$_3$ (1 M). The aqueous phase was then extracted with ethyl acetate (2×15 mL). The ethyl acetate extract was dried (MgSO$_4$) and the ethyl acetate removed under reduced pressure. The residue was dissolved in toluene (10 mL) and PPh$_3$ (0.324 g, 1.52 mmol) to provide a solution that was then refluxed for 18 h before being cooled to 0° C. The precipitate that formed was filtered and dried to yield the sub-title compound as a white solid.

Yield=0.468 g, 31.3%, m.p.>230° C.

$\nu_{max}$ KBr/cm$^{-1}$, 3053, 2990, 2964, 2903 υ(C—H), 1615 υ(C=N), 1591, 1561, 1485, 1473 υ(P—C), 1436 υ(C=C).

$\delta_H$ $^1$H (DMSO), 5.76 (2H, d, CH$_2$ (J=15.1 Hz)), 7.5 (1H, d, Ar—H, J=8.4), 7.55 (2H, t, Ar—H (J=7.0 Hz)), 7.71 (6H, m, Ar—H), 7.83 (10H, m, Ar—H), 8.35 (1H, d, Ar—H (J=8.5 Hz)).

$\delta_P$ $\delta^{31}$P (CDCl$_3$), 25.35.

HRFABMS: Found 404.1570 (M$^+$) calculated for C$_{28}$H$_{23}$NP$^+$ 404.1563.

(iii) Ethyl 1-methyl-4-[(E)-2-(2-quinolinyl)ethenyl]-1H-pyrrole-2-carboxylate Alternative I The sub-title compound was prepared according to a procedure analogous to that described in Preparation 12(iv) above, using diethyl 2-quinolinyl methylphosphonate (see step (i) above) in place of 3-quinolinyl methylphosphonate.

Yield=0.248 g, 42%, m.p.=140-142° C.

Alternative II

A solution of triphenyl(2-quinolinylmethyl)phosphonium chloride (0.40 g, 0.9 mmol; see step (ii) above) in THF (10 mL) were placed in a round bottom flask at RT under N$_2$. BuLi (325 μL of 2.5 M in hexanes, 0.8 mmol) was added dropwise, with high stirring and the solution allowed to stir for a further 1 h. Ethyl 4-formyl-1-methyl-1H-pyrrole-2-carboxylate (0.175 g, 0.9 mmol) in THF (10 mL) was then added dropwise over 10 min, and the solution allowed to stir overnight. The solvent was then removed under reduced pressure and the residue dry loaded onto silica, and the product eluted using 1:2, ethyl acetate:hexane.

Yield=0.062 g, 22%, m.p.=138-140° C.

$\nu_{max}$ KBr/cm$^{-1}$: 2997, 2894 υ(C—H), 2854 υ(N-Me) 1689 υ(C=O), 1629 υ(C=C alkene), 1552, 1488, 1428 υ(C=C), 1359 δ(C—H).

$\delta_H$ $^1$H(CDCl$_3$), 1.38 (3H, t, 2(CH$_3$) (J=7.2 Hz)), 3.95 (3H, s, N—CH$_3$), 4.31 (2H, q, CH$_2$ J=7.0 Hz)), 7.02 (1H, d, Ar—H (J=1.6 Hz)), 7.11 (1H, d, (H)C=CH (J=16.4 Hz)), 7.28 (1H, d, Ar—H (J=1.6 Hz)), 7.48 (1H, t, Ar—H (J=7.2 Hz)), 7.55 (2H, m, Ar—H), 7.72 (1H, m, Ar—H), 7.88 (1H, d, Ar—H (J=8.0 Hz)), 8.08 (2H, m, Ar—H).

HRFABMS: Found 306.1370 calculated for C$_{19}$H$_{18}$N$_2$O$_2$ 306.1368.

(iv) 1-Methyl-4-[(E)-2-(2-quinolinyl)ethenyl]-1H-pyrrole-2-carboxylic acid

The title compound was prepared according to a procedure analogous to that described in Preparation 12(v) above, using ethyl 1-methyl-4-[(E)-2-(2-quinolinyl)ethenyl]-1H-pyrrole-2-carboxylate (see step (ii) above) in place of ethyl 1-methyl-4-[(E)-2-(3-quinolinyl)ethenyl]-1H-pyrrole-2-carboxylate.

Yield=0.095 g, 78%, m.p.>230° C.

$\nu_{max}$ KBr/cm$^{-1}$: 3423 υ(O—H) 2978 υ(N-Me), 2822 υ(Ar—H), 2864 υ(N-Me) 1680 υ(C=O), 1628 υ(C=C alkene), 1598 1554, 1489 υ(C=C).

$\delta_H$ $^1$H(CDCl$_3$): 3.87 (3H, s, N—CH$_3$), 6.84 (1H, d, Ar—H (J=1.6 Hz)), 6.92 (1H, d, C=C alkene (J=16.4 Hz)), 7.13 (1H, d, Ar—H (J=1.6 Hz)), 7.48 (1H, t, Ar—H (J=7.2 Hz)), 7.62 (1H, d, C=C Alkene (J=16.4 Hz)), 7.70 (2H, m, Ar—H), 7.89 (2H, m, Ar—H), 8.22 (1H, d, Ar—H (J=8.0 Hz)).

HRFABMS: Found 278.1054 calculated for $C_{17}H_{14}N_2O_2$ 278.1055.

Preparation 14

2-[(E)-2-(2-Quinolinyl)ethenyl]-1,3-thiazole-4-carboxylic acid (i) 2,2-Diethoxyacetamide (See, for Example, Inami, K., Shiba, T., *Bull. Chem. Soc. Jpn.*, 1985, 58, 352.)

Ethyl diethoxyacetate (Aldrich) (10 mL, 56.41 mmol) was added to concentrated $NH_4OH$ (50 mL) and the mixture allowed to stir until a homogeneous solution was obtained (40 hours). The solvent was then removed under reduced pressure to yield the sub-title compound as fine white needles (8.209 g, 99%).

m.p.=47-51° C.

$v_{max}$ KBr/cm$^{-1}$: 3495, 3298 $v$(N—H), 2898$v$(C—H), $v$(N-Me) 1673 $v$(C=O), 1317 $\delta$(C—O).

$\delta_H$ $^1$H(CDCl$_3$): 1.11 (6H, t, 2(CH$_3$) (J=8.0 Hz)), 4.55 (4H, m, 2(CH$_2$)), 4.64 (1H, s, C—H), 7.25 (2H, d, NH$_2$ (J=188.0 Hz)).

LREIMS: Found 148.00 (M+H) calculated for $C_6H_{13}NO_3$ 147.09.

(ii) Diethoxyacetonitrile (See, for Example, Inami, K., Shiba, T., *Bull. Chem. Soc. Jpn.*, 1985, 58, 352.)

2,2-Diethoxyacetamide (7.13 g, 49.04 mmol; see step (i) above) was dissolved in toluene (50 mL), NEt$_3$ (10.4 mL) was added followed by P$_2$O$_5$ (9.04 g, 64.32 mmol) and the mixture stirred for 1 h. The solvent was distilled off at atmospheric pressure, the distillation apparatus was then placed under reduced pressure and the distillation continued, the sub-title compound was collected as a clear colourless liquid (4.049 g, 64%).

B.P.=100° C. at 12-15 mmHg.

$v_{max}$ KBr/cm$^{-1}$: 2983, 2937, 2896 $v$(C—H), 2247 $v$(N≡C), 1067 $\delta$(C—O).

$\delta_H$ $^1$H(CDCl$_3$): 1.27 (6H, t, 2(CH$_3$) (J=8.0 Hz)), 3.73 (4H, m, 2(CH$_2$)), 5.31 (1H, s, C—H).

LREIMS: Found 130.13 (M+H) calculated for $C_6H_{11}NO_2$ 129.08.

(iii) 2,2-Diethoxyethanethioamide (See, for example, Inami, K., Shiba, T., *Bull. Chem. Soc. Jpn.*, 1985, 58, 352.)

Diethoxyacetonitrile (0.050 g, 0.5 mmol; see step (ii) above) was placed in a 10 mL microwavable vial, methanol (5 mL) and (NH$_4$)$_2$S (54 µL, 0.5 mmol (40% wt solution in water)) was then added. The vial was then heated to 80° C. at 100 W for 15 min and the reaction then allowed to cool to RT. The solvent was then removed under reduced pressure and the residue dissolved in ethyl acetate (15 mL) and extracted with water (2×10 mL) and brine (2×5 mL). The organic layer was then dried (MgSO$_4$), filtered and concentrated under reduced pressure to yield the sub-title compound as a white/off-white solid (0.081 g, 99%).

m.p.=92-94° C.

$v_{max}$ KBr/cm$^{-1}$: 3335, 3171 $v$(N—H), 2976, 2885 $v$(C—H), 2247 $v$(N—C), 1645, 1449 $v$(C=S), 1019 $\delta$(C—O).

$\delta_H$ $^1$H(CDCl$_3$): 1.26 (6H, t, 2(CH$_3$) (J=8.0 Hz)), 3.71 (4H, m, 2(CH$_2$)), 5.05 (1H, s, C—H), 7.70 (2H, d, —N—H).

(iv) Ethyl 2-(diethoxymethyl)-1,3-thiazole-4-carboxylate (See, for example, Inami, K., Shiba, T., *Bull. Chem. Soc. Jpn.*, 1985, 58, 352.)

2,2-Diethoxyethanethioamide (0.654 g, 6.03 mmol; see step (iii) above) and ethylbromopyruvate (Aldrich) (1.28 g, 6.10 mmol) were dissolved in ethanol (10 mL) in the presence of 4 Å molecular sieves (1 g). The mixture was refluxed for 45 min and the solvent removed under reduced pressure. The residue was then dissolved in ethyl acetate (20 mL) and extracted with saturated. NaHCO$_3$ solution (2×20 mL), and brine (2×20 mL). The organic fraction was then dried (MgSO$_4$), filtered and the solvent removed under reduced pressure to yield the sub-title compound (1.452 g, 93%).

$v_{max}$ KBr/cm$^{-1}$: 3108 $v$(Ar—H), 2981, 2885, 2856 $v$(C—H), 1735 $v$(C=O), 1505 $v$(C=N), 1042 $\delta$(C—O).

$\delta_H$ $^1$H(CDCl$_3$): 1.29 (9H, m, 2(CH$_3$)), 3.71 (4H, m, 2(CH$_2$)), 4.47 (2H, q, CH$_2$ (J=7.8 Hz)), 5.70 (1H, s, C—H), 8.19 (1H, s, Ar—H).

HRFABMS: Found 260.0956 (M+H) calculated for $C_{11}H_{17}NO_4S$ 259.0878.

(v) Ethyl 2-formyl-1,3-thiazole-4-carboxylate (See, for example, Inami, K., Shiba, T., *Bull. Chem. Soc. Jpn.*, 1985, 58, 352.)

Ethyl 2-(diethoxymethyl)-1,3-thiazole-4-carboxylate (1.34 g, 5.17 mmol; see step (iv) above) was taken up in acetone (100 mL) and a solution of 1N HCl (12.8 mL) was then added. The solution was refluxed for 45 min and the solvent removed under reduced pressure. The residue was then dissolved in ethyl acetate (40 mL) and extracted with saturated NaHCO$_3$ solution (2×40 mL) and brine (2×40 mL). The organic fraction was then dried (MgSO$_4$), filtered and the solvent removed under reduced pressure to yield the sub-title compound as a light brown solid (0.937 g, 98%).

m.p.=65-67° C. (Lit=67-68° C.).

$v_{max}$ KBr/cm$^{-1}$: 3116 $v$(Ar—H), 2983, 2910, 2814 $v$(C—H), 173 $v$(C=O), 1513 $v$(C=N), 1060 $\delta$(C—O).

$\delta_H$ $^1$H(CDCl$_3$): 1.47 (3H, t, CH$_3$ (J=8.0 Hz)), 4.50 (2H, q, CH$_2$ (J=8.0 Hz)), 8.52 (1H, d, Ar—H (J=1.2 Hz)), 10.08 (1H, d, Ar—COH (J=1.2 Hz)).

HRFABMS: Found 186.0228 (M+H) calculated for $C_7H_7NO_3S$ 185.0147.

(vi) Ethyl 2-[(E)-2-(2-quinolinyl)ethenyl]-1,3-thiazole-4-carboxylate

Diethyl 2-quinolinylmethylphosphonate (0.580 g, 2.08 mmol; see Preparation 13(i) above) was dissolved in anhydrous THF (2 mL), NaH (0.273 g, 11 mmol) was then added in small portions and the resulting solution allowed to stir for 10 min. Ethyl 2-formyl-1,3-thiazole-4-carboxylate (0.387 g, 2.08 mmol; see step (v) above) in anhydrous THF (3 mL) was added dropwise and the solution allowed to stir for 16 h. Water (5 mL) was then added (dropwise initially), during which time the sub-title compound precipitated as a light brown/yellow solid.

Yield=0.232 g, 36%, m.p.=183-186° C.

$v_{max}$ KBr/cm$^{-1}$: 3124, 3043 $v$(Ar—H), 2955, 2925, 2899, 2853 $v$(C—H), 1730 $v$(C=O), 1612, 1627 $v$(C=C alkene), 1592 1553, 1479 $v$(C=C).

$\delta_H$ $^1$H(CDCl$_3$): 1.34 (3H, t, CH$_3$ (J=8.0 Hz)), 4.34 (2H, q, CH$_2$ (J=8.0 Hz)), 7.62 (1H, t, Ar—H (J=7.2 Hz)), 7.74 (1H, d, C=C alkene (J=16.1 Hz)), 7.79 (1H, t, Ar—H (J=6.8 Hz)), 7.98 (3H, m, Ar—H), 8.05 (1H, d, C=C Alkene (J=16.1 Hz)), 8.42 (1H, d, Ar—H (J=8.5 Hz)), 8.56 (1H, s, Ar—H).

HRFABMS: Found 310.0772 calculated for C$_{17}$H$_{14}$N$_2$O$_2$S 310.0776.

(vii) 2-[(E)-2-(2-Quinolinyl)ethenyl]-1,3-thiazole-4-carboxylic acid

2-[(E)-2-(2-Quinolinyl)ethenyl]-1,3-thiazole-4-carboxylate (0.137 g, 0.44 mmol; see step (vi) above) was suspended in ethanol (2 mL), NaOH (0.052 g, 1.32 mmol) in water (5 mL) was added and the solution was then refluxed for 2 h. The reaction was then hot-filtered and then cooled to 0° C., whereupon dilute HCl was added dropwise until the title compound precipitated as a yellow solid (0.103 g, 83%).

m.p.=218-220° C.

$\nu_{max}$ KBr/cm$^{-1}$: 3469 $\upsilon$(O—H), 3105, 3068 $\upsilon$(Ar—H), 2923, 2853, $\upsilon$(C—H), 1715 $\upsilon$(C=O), 1640, 1632 $\upsilon$(C=C alkene), 1599 1541, 1493 $\upsilon$(C=C), 1320 $\delta$(C—O).

$\delta_H$ $^1$H(CDCl$_3$): 7.74 (1H, t, Ar—H (J=7.2 Hz)), 7.76 (1H, d, C=C alkene (J=16.1 Hz)), 7.93 (1H, t, Ar—H (J=7.2 Hz)), 8.11 (1H, d, Ar—H (J=8.5 Hz)), 8.05 (1H, d, Ar—H (J=8.5 Hz)), 8.19 (2H, m, Ar—H), 8.24 (1H, d, C=C alkene (J=16.1 Hz)), 8.58 (1H, s, Ar—H), 8.65 (1H, d, Ar—H (J=8.5 Hz)).

HRFABMS: Found 282.0465 calculated for C$_{17}$H$_{14}$N$_2$O$_2$ 282.0463.

Preparation 15

4-[(Q-2-(2-Quinolinyl)ethenyl]benzoic acid

To a solution of methyl 4-[(diethoxyphosphoryl)methyl]benzoate (910 mg, 3.18 mmol; see Preparation 4(i) above) in THF (20 mL, dry) under a nitrogen atmosphere was added sodium hydride (520 mg, 60% dispersion in oil, 13.00 mmol) at 0° C. 2-Quinolinecarbaldehyde (500 mg, 3.18 mmol) was dissolved in THF (10 mL, dry) then added dropwise to the reaction mixture at 0° C. under N$_2$. The reaction mixture was stirred at room temperature for 1 h and then quenched with water. The pH level of the mixture was adjusted to pH 4 by the dropwise addition of HCl$_{(conc.)}$ with stirring at 0° C. The yellow solid material formed was collected by filtration and suspended in methanol (5 mL), to which a solution of sodium hydroxide was added (572 mg, 10 mL water). The reaction mixture was heated under reflux for 3 h and a yellow solid formed. The reaction mixture was extracted with ether (100 mL) and the solid material dissolved. The aqueous layer was collected and cooled to 0° C. concentrated HCl was added dropwise with stirring until pH 4, at which point a precipitate formed. The yellow precipitate was collected, washed with water and dried to give the title compound (403 mg, 46%, carboxylic acid), m.p.=265-268° C. (decomposition).

$^1$H NMR (DMSO-d$_6$): 13.01 (1H, br), 8.50 (1H, d, J=8.5 Hz), 8.07 (1H, d, J=8.5 Hz), 8.02-7.96 (5H, m), 7.87 (2H, d, J=8.4 Hz), 7.84 (1H, t, J=7.2 Hz), 7.67-7.61 (d, J=16.5 Hz & t, J=6.5 Hz).

IR (KBr): 3383, 2593, 1716, 1628, 1603, 1416, 1324, 1209, 1105, 970, 845, 747 cm$^{-1}$.

HRCIMS: Found: 276.1022 calculated for C$_{18}$H$_{14}$O$_2$N 276.1025.

Preparation 16

4-[(E)-2-(2-Chloro-3-quinolinyl)ethenyl]benzoic acid

The title compound was prepared according to a procedure analogous to that described in Preparation 15 above, using 2-chloro-3-quinolinecarbaldehyde in place of 2-quinolinecarbaldehyde to produce the title compound as; a white solid (495 mg, 61%), m.p.=190° C. (softening) then sublimed at around 270° C.

$^1$H NMR (DMSO-d$_6$): 13.00 (1H, br), 8.92 (1H, s), 8.08 (1H, d, J=7.6 Hz), 8.03-7.95 (3H, m), 7.84-7.77 (3H, m), 7.70-7.55 (3H, m).

IR (KBr): 3383, 2593, 1716, 1628, 1603, 1416, 1324, 1209, 747 cm$^{-1}$. HREIMS: Found: 309.0558 calculated for C$_{18}$H$_{12}$$^{35}$ClNO$_2$ 309.0556

Preparation 17

4-[(E)-2-(2-Naphthyl)ethenyl]benzoic acid sodium salt or sodium 4-((E)-2-(naphthalene-6-yl)vinyl)benzoate (i) Methyl 4-[(E)-2-(2-naphthyl)ethenyl]benzoate To a solution of methyl 4-[(diethoxyphosphoryl)methyl]benzoate (916 mg, 3.20 mmol; see Preparation 4(i) above) in THF (20 mL, dry) under nitrogen atmosphere was added a sodium hydride (520 mg, 60% dispersion in oil, 13.00 mmol) at 0° C. 2-Naphthaldehyde (500 mg, 3.20 mmol) was dissolved in THF (10 mL, dry) then added dropwise to the reaction mixture at 0° C. under N$_2$ and the reaction mixture stirred at room temperature for 1 h followed by quenching with water. The pH level of the mixture was adjusted to pH 4 by the dropwise addition of HCl$_{(conc.)}$ with stirring at 0° C. TLC analysis showed that it was the required product (282 mg). Extraction of the water layer with ethyl acetate followed by drying (MgSO$_4$) gave the sub-title compound (total amount 846 mg, 92%), m.p.=195-198° C.

$^1$H NMR (DMSO-d$_6$): 8.07 (1H, s), 7.99 (2H, d, J=8.4 Hz), 7.95-7.90 (3H, d & m, J=6.3 Hz), 7.81 (2H, d, J=8.4 Hz), 7.63 (1H, d, J=16.4 Hz), 7.55-7.48 (3H, d & m, J=16.4 Hz), 3.87 (3H, s).

IR (KBr): 1718, 1601, 1455, 1439, 1411, 1284, 1193, 1179, 1110, 962, 869, 819, 748, 700 cm$^{-1}$. HREIMS: Found: 288.1151 calculated for C$_{20}$H$_{16}$O$_2$ 288.1150.

(ii) 4-[(E)-2-(2-Naphthyl)ethenyl]benzoic acid sodium salt or sodium 4-((E)-2-(naphthalene-6-yl)vinyl)benzoate Methyl 4-[(E)-2-(2-naphthyl)ethenyl]benzoate (280 mg, 0.972 mmol; see step (i) above) was suspended in methanol (2 mL) and sodium hydroxide solution (NaOH 550 mg, 13.75 mmol in water 10 mL) was added. The reaction mixture was heated, with stirring, under reflux overnight. The solvent was removed under reduced pressure and the resultant white solid was triturated with water and filtered to give the title compound (285 mg, 99%).

m.p.>230° C.

$^1$H NMR (DMSO-d$_6$): 8.15-7.75 (8H, m), 7.60-7.35 (5H, m).

IR (KBr): 3393, 1717, 1583, 1535, 1418, 1283, 1102, 957, 865, 824, 741 cm$^{-1}$.

HREIMS: Found: 229.1015 calculated for $C_{18}H_{13}$ 229.1017 (decarboxylation occurred in the probe).

Preparation 18

2-{[(4-Amino-1-methyl-1H-pyrrol-2-yl)carbonyl]amino}-5-isopentyl-N-[2-(4-morpholinyl)ethyl]-1,3-thiazole-4-carboxamide (i) 5-Isopentyl-2-{[(1-methyl-4-nitro-1H-pyrrol-2-yl)carbonyl]amino}-N-[2-(4-morpholinyl)ethyl]-1,3-thiazole-4-carboxamide 5-Isopentyl-2-{[(1-methyl-4-nitro-1H-pyrrol-2-yl)carbonyl]amino}-1,3-thiazole-4-carboxylic acid (330 mg, 0.90 mmol; see Preparation 3(iv) above) was dissolved in DMF (2.5 mL, dry), to which was added NMM (0.1 mL, dry), 2-(4-morpholinyl)ethanamine (117 mg, 0.90 mmol), and HBTU (682 mg, 1.80 mmol) at room temperature with stirring. The stirring was continued at room temperature for 24 h and then the reaction mixture was extracted with sodium hydroxide solution (381 mg, 9.52 mmol in water 10 mL) and ethyl acetate (3×50 mL). The organic layers were collected, dried ($MgSO_4$) and the solvent removed under reduced pressure. The crude product was purified by column chromatography using ethyl acetate/methanol containing 1% TEA as eluent ($R_F$=0.15). The sub-title compound was obtained as pale yellow solid (400 mg, 93%).

m.p. 189-192° C.
$^1$H NMR (DMSO-$d_6$): 12.48 (1H, br), 8.30 (1H, d, J=1.6 Hz), 7.95 (1H, d, J=1.6 Hz), 7.66 (1H, t, J=5.6 Hz), 3.98 (3H, s), 3.59 (4H, t, J=4.4 Hz), 3.40 (2H, q, J=6.2 Hz), 3.20 (2H, t, J=7.7 Hz), 2.69 (3H, s), 2.45-2.40 (4H, m), 1.61-1.48 (3H, m), 0.92 (6H, d, J=6.4 Hz).
IR (KBr): 3404, 1661, 1559, 1474, 1310, 1292, 1110, 841 $cm^{-1}$.
HRFABMS: Found: 479.2074 calculated for $C_{21}H_{31}O_5N_6S$ 479.2077.

(ii) 2-{[(4-Amino-1-methyl-1H-pyrrol-2-yl)carbonyl]amino}-5-isopentyl-N-[2-(4-morpholinyl)ethyl]-1,3-thiazole-4-carboxamide 5-Isopentyl-2-{[(1-methyl-4-nitro-1H-pyrrol-2-yl)carbonyl]amino}-N-[2-(4-morpholinyl)ethyl]-1,3-thiazole-4-carboxamide (400 mg, 0.836 mmol; see step (i) above) was dissolved in methanol (25 mL) to which was added Pd/C-10% (300 mg) at 0° C. (under $N_2$) with stirring. The reaction mixture was hydrogenated for 4 h at room temperature and atmospheric pressure to give the title compound, which was used without further purification.

Preparation 19

6-{(E)-2-[4-(Methylsulfanyl)phenyl]ethenyl}nicotinic acid (i) Methyl 6-{(E)-2-[4-(methylsulfanyl)phenyl]ethenyl}nicotinate A mixture of 4-(methylsulfanyl)benzaldehyde (250 mg, 1.52 mmol), methyl 6-methylnicotinate (230 mg, 1.52 mmol), acetic anhydride (310 mg, 3.04 mmol) and a catalytic amount of zinc chloride was heated under reflux for 12 h. The reaction mixture was allowed to cool to room temperature before crushed ice was added followed by sodium hydroxide solution 10% (dropwise with stirring) until the mixture was basic (pH 8). Dichloromethane was added and the layers separated. The combined organic layers were collected, dried ($MgSO_4$) and concentrated under reduced pressure to give the crude product as brown solid. The crude mixture was purified by column chromatography (ethyl acetate/n-hexane, 1:1, $R_F$=0.80), followed by recrystallization from methanol to give the sub-title compound as pale yellow crystals (251 mg, 58%).

m.p.=157-159° C.
$^1$H NMR (DMSO-$d_6$): 9.04 (1H, d, J=2.0 Hz), 8.26 (1H, dd, J=2.2 Hz & J=8.2 Hz), 7.81 (1H, d, J=16.0 Hz), 7.65 (3H, d, J=8.3 Hz), 7.38 (1H, d, J=16.0 Hz), 7.29 (2H, d, J=8.4 Hz), 3.15 (3H, s), 2.49 (3H, s).
IR (KBr): 1712, 1586, 1435, 1280, 1114, 978, 849, 813, 774, 733 $cm^{-1}$.
HRCIMS: Found: 286.0899 calculated for $C_{16}H_{16}O_2NS$ 286.0902.

(ii) 6-{(E)-2-[4-(Methylsulfanyl)phenyl]ethenyl}nicotinic acid

Methyl 6-{(E)-2-[4-(methylsulfanyl)phenyl]ethenyl}nicotinate (80 mg, 0.280 mmol; see step (i) above) was suspended in methanol (4 mL) and a solution of sodium hydroxide (250 mg, in water 10 mL) and the reaction mixture was heated under reflux for 4 h. The solvent was removed under reduced pressure and the aqueous layer was extracted with DCM. The aqueous layer was cooled to 0° C. with ice then $HCl_{(conc.)}$ was added dropwise with stirring until pH4, where a precipitate formed. The solid material was filtered, washed with water and dried under reduced pressure to give the title compound as pale yellow solid (75 mg, 99%).

m.p.=250-253° C.
$^1$H NMR (DMSO-$d_6$): 9.02 (1H, d, J=2.0 Hz), 8.23 (1H, dd, J=2.2 Hz & J=8.2 Hz), 7.79 (1H, d, J=16.0 Hz), 7.63 (3H, m), 7.37 (1H, d, J=16.0 Hz), 7.29 (2H, d, J=8.4 Hz), 4.49 (3H, s).
IR (KBr): 3419, 2920, 2500, 1698, 1565, 1493, 1381, 1287, 1142, 1090, 967, 809, 775, 786 $cm^{-1}$.
HRFABMS Found: 272.0739 calculated for $C_{15}H_{14}O_2NS$ 272.0745.

Preparation 20

2-{(E)-2-[4-(Methylsulfanyl)phenyl]ethenyl}-6-quinolinecarboxylic acid

A mixture of 4-(methylsulfanyl)benzaldehyde (220 mg, 1.33 mmol), 2-methyl-6-quinolinecarboxylic acid (250 mg, 1.33 mmol), acetic anhydride (310 mg, 3.04 mmol), zinc chloride (catalytic amount) and xylene (1 mL) was heated at 140° C. overnight. A yellow solid material precipitated and was triturated with water and ethyl acetate containing 5% methanol then filtered. The title compound was dried under reduced pressure at 50° C. overnight and furnished a yellow solid (270 mg, 63%).

m.p.=294-297° C. (decomposition), $R_F$=0.50 (ethyl acetate, fluorescent under the UV lamp).
$^1$H NMR (DMSO-$d_6$): 13.12 (1H, br), 8.61 (1H, d, J=1.8 Hz), 8.53 (1H, d, J=8.6 Hz), 8.19 (1H, dd, J=1.8 Hz & J=8.7 Hz), 8.03 (8.7 Hz), 7.93 (1H, d, J=8.6 Hz), 7.90 (1H, d, J=16.2 Hz), 7.72 (2H, d, J=8.4 Hz), 7.49 (1H, d, J=16.3 Hz), 7.33 (2H, J=8.4 Hz), 2.52 (3H, s).
IR (KBr): 3422, 2918, 2534, 1681, 1615, 1586, 1493, 1472, 1290, 1185, 1089, 960, 820, 756 $cm^{-1}$.
HRCIMS: Found: 322.0905 calculated for $C_{19}H_{16}O_2NS$ 322.0902.

Preparation 21

6-[(E)-2-(4-Methoxyphenyl)ethenyl]nicotinic acid

(i) Methyl 6-[(E)-2-(4-methoxyphenyl)ethenyl]nicotinate

4-Methoxybenzaldehyde (210 mg, 1.52 mmol), methyl 6-methylnicotinate (230 mg, 1.52 mmol), acetic anhydride (310 mg, 3.04 mmol) and catalytic amount of zinc chloride were heated at 140° C. with stirring for 12 h. Ethyl acetate and brine were added to the cooled reaction mixture and the product was extracted. The organic layers were combined, dried ($MgSO_4$) and the solvent removed under reduced pressure. The crude product was applied to a silica gel column and the product was eluted with ethyl acetate/n-hexane (1:1 $R_F$=0.60 fluorescent under the UV lamp). Fractions containing the required product were collected and the solvents removed under reduced pressure to give the sub-title compound as a yellow solid (87 mg, 21%).

m.p.=170-173° C. [ref. m.p.=170° C.: Cluzan, R. and Katz, L. The Boots Company Ltd. U.S. Pat. No. 4,009,174, 1977].

$^1$H NMR (DMSO-$d_6$): 9.04 (1H, d, J=2.0 Hz), 8.25 (1H, dd, J=2.2 Hz & J=8.2 Hz), 7.81 (1H, d, J=16.0 Hz), 7.67-7.62 (3H, m), 7.28 (1H, d, J=16.0 Hz), 7.00 (2H, d, J=8.8 Hz), 3.88 (3H, s), 3.80 (3H, s).

IR (KBr): 1717, 1606, 1591, 1511, 1433, 1290, 1254, 1175, 1111, 1020, 844, 818, 760, 734 $cm^{-1}$.

HRCIMS: Found: 270.1127 calculated for $C_{16}H_{16}O_3N$ 270.1130.

(ii) 6-[(E-2-(4-Methoxyphenyl)ethenyl]nicotinic acid

Methyl 6-[(E)-2-(4-methoxyphenyl)ethenyl]nicotinate (80 mg, 0.297 mmol; see step (i) above) was dissolved in methanol (5 mL) to which sodium hydroxide solution (145 mg in 10 mL water) was added. The reaction mixture was heated under reflux for 3 h. The solvent was removed under partial reduced pressure and the remaining solution was cooled to 0° C. Hydrochloric acid (conc.) was added dropwise with vigorous stirring until pH4 where a precipitate formed. The yellow solid material was collected by filtration, washed with water and dried under reduced pressure at 50° C. to give the title compound (59 mg, 78%).

m.p.=230-233° C. (sublimed around 200° C.).

$^1$H NMR (DMSO-$d_6$): 9.03 (1H, d, J=2.0 Hz), 8.29 (1H, dd, J=2.1 Hz & J=8.2 Hz), 7.90-7.65 (4H, m), 7.29 (1H, d, J=16.0 Hz), 7.01 (2H, m), 3.80 (3H, s).

IR (KBr): 1717, 1681, 1635, 1595, 1513, 1292, 1250, 1173, 1023, 825 $cm^{-1}$.

HRFABMS: Found: 256.0972 calculated for $C_{15}H_{14}O_3N$ 256.0974.

Preparation 22

2-[(E)-2-(4-Methoxyphenyl)ethenyl]-6-quinolinecarboxylic acid

A mixture of 2-methyl-6-quinolinecarboxylic acid (200 mg, 0.936 mmol), 4-methoxybenzaldehyde (228 mg, 0.936 mmol), acetic anhydride (630 mg, 6.18 mmol) and a catalytic amount of zinc chloride was heated at 140° C. for 12 h with stirring. The cooled reaction mixture was extracted with water and ethyl acetate. The organic layer was collected, dried ($MgSO_4$) and the solvent was removed under reduced pressure to give dark brown solid. This material was applied to a silica gel column and the product was eluted with ethyl acetate/n-hexane (1/4). Fractions containing the required product ($R_F$=0.20 ethyl acetate/n-hexane 2/1, fluorescent under UV lamp) were collected and the solvents were removed under reduced pressure. The residue as a yellow solid was triturated with n-hexane and filtered to give the title compound (71 mg, 25%), m.p.=274-277° C. (sublimed around 240° C.).

$^1$H NMR (DMSO-$d_6$): 13.11 (1H, br), 8.60 (1H, d, J=1.8 Hz), 8.51 (1H, d, J=8.6 Hz), 8.19 (1H, dd, J=1.9 Hz & J=8.8 Hz), 7.91 (1H, d, J=8.7 Hz), 7.89 (1H, d, J=16.4 Hz), 7.72 (2H, d, 8.8 Hz), 7.38 (1H, d, J=16.3 Hz), 7.02 (2H, d, J=8.8 Hz), 3.81 (3H, s).

IR (KBr): 1682, 1615, 1593, 1510, 1467, 1289, 1252, 1170, 1030, 968, 830 $cm^{-1}$.

HREIMS. Found: 305.1055 Calculated for $C_{19}H_{15}NO_3$ 305.1052.

Preparation 23

1-Methyl-N-[1-methyl-5-({[1-methyl-5-({[2-(4-morpholinyl)ethyl]amino}-carbonyl)-1H-pyrrol-3-yl]amino}carbonyl)-1H-pyrrol-3-yl]-4-amino-1H-pyrrole-2-carboxamide

(i) 1-Methyl-N-[1-methyl-5-({[1-methyl-5-({[2-(4-morpholinyl)ethyl]amino}-carbonyl)-1H-pyrrol-3-yl]amino}carbonyl)-1H-pyrrol-3-yl]-4-nitro-1H-pyrrole-2-carboxamide 1-Methyl-4-{[(1-methyl-4-nitro-1H-pyrrol-2-yl)carbonyl]amino}-N-[2-(4-morpholinyl)ethyl]-1H-pyrrole-2-carboxamide (0.343 g, 0.85 mmol; see Preparation 1(iv) above) was dissolved in methanol (10 mL) and cooled to 0° C., Pd/C (200 mg) was then added in small portions and the solution stirred under $H_2$ for 3 h. The solution was then filtered and the solvent removed under reduced pressure. A solution of 1-methyl-4-nitro-1H-pyrrole-2-carbonyl chloride (160 g, 0.85 mmol) in DCM (10 mL) was then added and allowed to stir for 1 h at RT, the solvent was removed under reduced pressure, the crude product obtained was separated on basified silica using a 1:1 solution of methanol ethyl acetate to yield the sub-title compound.

Yield=0.259 g, 58%, M.P.>230° C.

$\nu_{max}$ KBr/$cm^{-1}$: 3334, 3279 $\upsilon$(N—H), 3135, 3068 $\upsilon$(Ar—H), 2929,2867, $\upsilon$(C—H), 1671, 1633 $\upsilon$(C=O), 1535, 1308 $\upsilon$(N=O), 1115 $\delta$(C—O).

$\delta_H$ $^1$H (DMSO): 3.13 (2H, m, $CH_2$), 3.25 (2H, m, $CH_2$), 3.58 (4H, m, ($CH_2$)—O—($CH_2$)), 3.74 (2H, m, $CH_2$), 3.82 (3H, s, N-Me), 3.86 (3H, s, N-Me), 3.96 (3H, s, N-Me), 6.98 (1H, d, Ar—H (J=1.6 Hz)), 7.05 (1H, d, Ar—H (J=1.6 Hz)), 7.22 (1H, d, Ar—H (J=1.6 Hz)), 7.26 (1H, d, Ar—H (J=1.6 Hz)), 7.60 (1H, d, Ar—H (J=1.6 Hz)), 8.18 (1H, d, Ar—H (J=1.6 Hz)), 8.28 (1H, t, N—H (J=5.6 Hz)), 9.97 (1H, s, NH), 10.12 (1H, s, NH).

LREIMS: Found 527.42 (M+H) calculated for $C_{24}H_{30}N_8O_6$ 526.25.

(ii) 1-Methyl-N-[1-methyl-5-({[1-methyl-5-({[2-(4-morpholinyl)ethyl]amino}carbonyl)-1H-pyrrol-3-yl]amino}carbonyl)-1H-pyrrol-3-yl]-4-amino-1H-pyrrole-2-carboxamide 1-Methyl-N-[1-methyl-5-({[1-methyl-5-({[2-(4-morpholinyl)ethyl]amino}-s carbonyl)-1H-pyrrol-3-yl]amino}carbonyl)-1H-pyrrol-3-yl]-4-nitro-1H-pyrrole-2-carboxamide (156 mg, 0.33 mmol; see step (i) above) was suspended in methanol (25 mL) to which Pd/C-10% (108 mg)

Example 1

4-({[4-({4-[(E)-2-(3-Methoxyphenyl)ethenyl] benzoyl}amino)-1-methyl-1H-pyrrol-2-yl] carbonyl}amino)-1-methyl-N-[2-(4-morpholinyl) ethyl]-1H-pyrrole-2-carboxamide, trifluoroacetate salt To 4-amino-1-methyl-N-[1-methyl-5-({[2-(4-morpholinyl)ethyl]amino}carbonyl)-1H-pyrrol-3-yl]-1H-pyrrole-2-carboxamide (46 mg, 0.124 mmol; see Preparation 1 above) in DMF (1 mL), HBTU (100 mg, 0.264 mmol), 4-[(E)-2-(3-methoxyphenyl)ethenyl]benzoic acid (32 mg, 0.124 mmol; see Preparation 4 above) were added at room temperature with stirring. The reaction mixture was left standing at room temperature overnight. The product was purified by HPLC (no work up required) to give the title compound as a pale yellow solid (26 mg, 29%) with no distinct melting point.

$^1$H NMR (DMSO-$d_6$): 10.32 (1H, s), 9.97 (1H, s), 9.68 (1H, br), 8.23 (1H, t, 5.6 Hz), 7.97 (2H, d, 8.4 Hz), 7.75 (2H, d, J=5.6 Hz), 7.3-7.29 (4H, m), 7.22 (2H, m), 7.12 (1H, d, J=1.5 Hz), 7.00 (1H, d, J=1.5 Hz), 6.90 (1H, dd, J=1.5 Hz & J=3.7 Hz), 3.99 (2H, m), 3.88 (3H, s), 3.83 (3H, s), 3.81 (3H, s), 3.67-3.55 (6H, m), 3.27 (2H, m), 3.14 (2H, m).

IR (KBr): 1681, 1642, 1577, 1464, 1435, 1404, 1266, 1202, 1134 cm$^{-1}$.

HRFABMS: found: 611.2971 calculated for $C_{34}H_{39}N_6O_5$ 611.2982.

Example 2

1-Methyl-4-({[1-methyl-4-({4-[(E)-2-(3-quinolinyl) ethenyl]benzoyl}amino)-1H-pyrrol-2-yl] carbonyl}amino)-N-[2-(4-morpholinyl)ethyl]-1H-pyrrole-2-carboxamide, trifluoroacetate salt To 4-amino-1-methyl-N-[1-methyl-5-({[2-(4-morpholinyl)ethyl]amino}-carbonyl)-1H-pyrrol-3-yl]-1H-pyrrole-2-carboxamide (46 mg, 0.124 mmol; see Preparation 1 above) in DMF (1 mL), HBTU (100 mg, 0.264 mmol), 4-[(E)-2-(3-quinolinyl)ethenyl]benzoic acid (34 mg, 0.123 mmol; see Preparation 5 above) were added at room temperature with stirring. The reaction mixture was left standing at room temperature overnight. The product was purified by HPLC (no work up required) to give the title compound as a pale yellow solid (36 mg, 39%) with no distinct melting point.

$^1$H NMR (DMSO-$d_6$): 10.35 (1H, s), 9.98 (1H, s), 9.55 (1H, br), 9.28 (1H, d, J=2.0 Hz), 8.59 (1H, d, J=2.0 Hz), 8.23 (1H, t, J=8.0 Hz), 8.05-7.97 (5H, m), 7.83-7.75 (4H, m), 7.70-7.60 (4H, m), 7.34 (1H, d, J=1.7 Hz), 7.21 (1H, d, J=1.7 Hz), 7.13 (1H, d, J=1.7 Hz), 7.01 (1H, d, J=1.7 Hz), 4.03-3.99 (2H, m), 3.88 (3H, s), 3.83 (3H, s), 3.69-3.63 (2H, m), 3.59-3.54 (4H, m), 3.28 (2H, m), 3.15 (2H, m).

IR (KBr): 1681, 1642, 1577, 1464, 1435, 1404, 1266, 1202, 1134 cm$^{-1}$.

HRFABMS: found: 632.2982 calculated for $C_{36}H_{38}N_7O_4$ 632.2985.

Example 3

1-Methyl-N-[1-methyl-5-({[2-(4-morpholinyl)ethyl] amino}carbonyl)-1H-pyrrol-3-yl]-4-({4-[(E)-2-(1-methyl-1H-pyrrol-2-yl)ethenyl]benzoyl}amino)-1H-pyrrole-2-carboxamide, trifluoroacetate salt (i) 1-Methyl-4-{[(1-methyl-4-amino-1H-pyrrol-2-yl) carbonyl]amino}-N-[2-(4-morpholinyl)ethyl]-1H-pyrrole-2-carboxamide 1-Methyl-4-{[(1-methyl-4-nitro-1H-pyrrol-2-yl)carbonyl]amino}-N-[2-(4-morpholinyl)ethyl]-1H-pyrrole-2-carboxamide (86 mg, 0.212 mmol; see Preparation 1 (iv) above) was suspended in methanol (25 mL) to which Pd/C-10% (80 mg) was added at 0° C. under nitrogen with stirring. The reaction mixture was hydrogenated for 4 h at room temperature and atmospheric pressure. The catalyst was removed over Kieselguhr and methanol was removed under reduced pressure to give the amine, which was dissolved in DMF (1 mL, dry). The resulting amine was utilised in the next step without purification.

(ii) 1-Methyl-N-[1-methyl-5-({[2-(4-morpholinyl) ethyl]amino}carbonyl)-1H-pyrrol-3-yl]-4-({4-[(E)-2-(1-methyl-1H-pyrrol-2-yl ethenyl]benzoyl}amino)-1H-pyrrole-2-carboxamide, trifluoroacetate salt 4-[(E)-2-(1-Methyl-1H-pyrrol-2-yl)ethenyl]benzoic acid, lithium salt (39 mg, 0.166 mmol; see Preparation 6 above) was suspended in DMF (1 mL, dry) to which HBTU (315 mg, 0.830 mmol) was added followed by the amine solution from step (i) above. The reaction mixture was left stirring at room temperature overnight. The product was purified by HPLC (no work up required) to give title compound as a pale yellow solid (23 mg, 16%) with no distinct melting point.

$^1$H NMR (DMSO-$d_6$): 10.26 (1H, s), 9.96 (1H, s), 9.55 (1H, br), 8.22 (1H, br), 7.93 (2H, d, J=8.4 Hz), 7.68 (2H, d, J=8.4 Hz), 7.32 (2H, m), 7.20 (1H, s), 7.11 (1H, s), 7.00 (1H, s), 6.95 (1H, d, J=16.2 Hz), 6.82 (1H, s), 6.53 (1H, s), 6.06 (1H, t, J=3.1 Hz), 4.02 (2H, m), 3.87 (3H, s), 3.83 (3H, s), 3.72 (3H, s), 3.69-3.66 (2H, m), 3.63-3.53 (4H, m), 3.26-3.23 (2H, m), 3.14-3.11 (2H, m).

IR (KBr): 1681, 1642, 1577, 1464, 1435, 1404, 1266, 1202, 1134 cm$^{-1}$.

HRFABMS: found: 584.2984 calculated for $C_{32}H_{38}N_7O_4$ 584.2985.

Example 4

N-[5-({[3-(Dimethylamino)propyl]amino}carbonyl)-1-methyl-1H-pyrrol-3-yl]-4-({4-[(E)-2-(3-methoxyphenyl)ethenyl]benzoyl}amino)-1-methyl-1H-pyrrole-2-carboxamide, trifluoroacetate salt To 4-{[(4-amino-1-methyl-1H-pyrrol-2-yl)carbonyl]amino}-N-[3-(dimethylamino)propyl]-1-methyl-1H-pyrrole-2-carboxamide (41 mg, 0.124 mmol; see Preparation 2 above) in DMF (1 mL), HBTU (141 mg, 0.372 mmol), 4-[(E)-2-(3-methoxyphenyl)ethenyl]benzoic acid (47 mg, 0.186 mmol; see Preparation 4 above) were added at room temperature with stirring. The reaction mixture was left standing at room temperature overnight. The product was purified by HPLC (no work up required) to give the title compound as a pale yellow solid (66 mg, 51%) with no distinct melting point.

$^1$H NMR (DMSO-$d_6$): 10.32 (1H, s), 9.94 (1H, s), 9.38 (1H, s), 8.15 (1H, t, J=5.8 Hz), 7.98 (2H, d, J=8.4 Hz), 7.75

(1H, d, J=8.4 Hz), 7.37 (2H, d, J=1.5 Hz), 7.33 (2H, m), 7.21 (2H, m), 7.19 (1H, d, J=1.5 Hz), 7.11 (1H, d, J=1.5 Hz), 6.95 (1H, d, J=1.5 Hz), 8.89 (1H, m), 3.87 (3H, s), 3.82 (3H, s), 3.81 (3H, s), 3.25 (2H, q, J=6.1 Hz), 3.06 (2H, m), 2.79 (6H, d, J=4.8 Hz), 1.84 (2H, quintet, J=6.7 Hz).

IR (KBr): 1681, 1642, 1581, 1540, 1464, 1435, 1404, 1266, 1202, 1134 cm$^{-1}$.

HRFABMS: found: 583.3036 calculated for $C_{33}H_{39}O_4N_6$ 583.3033.

Example 5

N-[5-({[3-(Dimethylamino)propyl]amino}carbonyl)-1-methyl-1H-pyrrol-3-yl]-1-methyl-4-({4-[(E)-2-(3-quinolinyl)ethenyl]benzoyl}amino)-1H-pyrrole-2-carboxamide, trifluoroacetate salt To 4-{[(4-amino-1-methyl-1H-pyrrol-2-yl)carbonyl]amino}-N-[3-(dimethylamino)propyl]-1-methyl-1H-pyrrole-2-carboxamide (41 mg, 0.124 mmol; see Preparation 2 above) in DMF (1 mL), HBTU (141 mg, 0.372 mmol), 4-[(E)-2-(3-quinolinyl)ethenyl]benzoic acid (51 mg, 0.186 mmol; see Preparation 5 above) were added at room temperature with stirring. The reaction mixture was left standing at room temperature overnight. The product was purified by HPLC (no work up required) to give the title compound as a pale yellow solid (15 mg, 19%) with no distinct melting point.

$^1$H NMR (DMSO-$d_6$): 10.35 (1H, s), 9.95 (1H, s), 9.34 (1H, br), 9.27 (1H, d, J=1.9 Hz), 8.57 (1H, d, J=1.9 Hz), 8.15 (1H, t, J=5.7 Hz), 8.02 (2H, d, J=8.5 Hz), 7.83 (2H, d, J=8.5 Hz), 7.76 (1H, dt, J=1.4 Hz & J=6.9 Hz), 7.66 (3H, m), 7.34 (1H, d, J=1.5 Hz), 7.19 (1H, d, J=1.5 Hz), 7.12 (1H, d, J=1.5 Hz), 6.95 (1H, d, J=1.5 Hz), 3.88 (3H, s), 3.82 (3H, s), 3.26 (2H, q, J=6.4 Hz), 3.10 (2H, m), 2.79 (6H, d, J=4.9 Hz), 1.84 (2H, quintet, J=7.9 Hz).

IR (KBr): 1681, 1642, 1577, 1464, 1436, 1404, 1266, 1202, 1134 cm$^{-1}$.

HRFABMS: found: 604.3038 calculated for $C_{35}H_{38}O_3N_7$ 604.3036.

Example 6

N-[5-({[3-(Dimethylamino)propyl]amino}carbonyl)-1-methyl-1H-pyrrol-3-yl]-4-({3-[(E)-2-(3-methoxyphenyl)ethenyl]benzoyl}amino-1-methyl-1H-pyrrole-2-carboxamide, trifluoroacetate salt To 4-{[(4-amino-1-methyl-1H-pyrrol-2-yl)carbonyl]amino}-N-[3-(dimethylamino)propyl]-1-methyl-1H-pyrrole-2-carboxamide (41 mg, 0.124 mmol; see Preparation 2 above) in DMF (1 mL), HBTU (141 mg, 0.372 mmol), 3-[(E)-2-(3-methoxyphenyl)ethenyl]benzoic acid (47 mg, 0.186 mmol; see Preparation 7 above) were added at room temperature with stirring. The reaction mixture was left standing at room temperature overnight. The product was purified by HPLC (no work up required) to give the title compound as a pale yellow solid (67 mg, 52%) with no distinct melting point.

$^1$H NMR (DMSO-$d_6$): 10.37 (1H, s), 9.95 (1H, s), 9.40 (1H, br), 8.17 (2H, m), 7.83 (1H, d, J=7.9 Hz), 7.79 (1H, d, J=7.9 Hz), 7.52 (1H, t, J=7.7 Hz), 7.36-7.29 (4H, m), 7.22 (2H, m), 7.19 (1H, d, J=1.5 Hz), 6.95 (1H, d, J=1.5 Hz), 6.89 (1H, m), 3.88 (3H, s), 3.82 (3H, s), 3.81 (3H, s), 3.25 (2H, q, J=6.0 Hz), 3.06 (2H, m), 2.79 (6H, d, J=4.9 Hz), 1.84 (2H, quintet, J=7.9 Hz).

IR (KBr): 1682, 1641, 1578, 1464, 1436, 1404, 1266, 1202, 1134 cm$^{-1}$.

HRFABMS: found: 583.3029 calculated for $C_{33}H_{39}O_4N_6$ 583.3033.

Example 7

N-[5-({[3-(Dimethylamino)propyl]amino}carbonyl)-1-methyl-1H-pyrrol-3-yl]-1-methyl-4-({4-[(E)-2-(4-pyridinyl)ethenyl]benzoyl}amino)-1H-pyrrole-2-carboxamide, trifluoroacetate salt (i) 1-Methyl-4-{[(1-methyl-4-amino-1H-pyrrol-2-yl)carbonyl]amino}-N-[3-(dimethylamino)propyl]-1H-pyrrole-2-carboxamide 1-Methyl-4-{[(1-methyl-4-nitro-1H-pyrrol-2-yl)carbonyl]amino}-N-[3-(dimethylamino)propyl]-1H-pyrrole-2-carboxamide (59 mg, 0.156 mmol; see Preparation 2(ii) above) was suspended in methanol (25 mL) to which Pd/C-10% (59 mg) was added at 0° C. under a nitrogen with stirring. The reaction mixture was hydrogenated for 3 h at room temperature and atmospheric pressure. The catalyst was removed over kieselguhr and methanol was removed under reduced pressure to give the amine, which was dissolved in DMF (1.5 mL, dry) and used without further purification.

(ii) N-[5-({[3-(Dimethylamino)propyl]amino}carbonyl)-1-methyl-1H-pyrrol-3-yl]-1-methyl-4-({4-[(E)-2-(4-pyridinyl)ethenyl]benzoyl}amino)-1H-pyrrole-2-carboxamide, trifluoroacetate salt To the amine solution (from step (i) above), HBTU (121 mg, 0.32 mmol), 4-[(E)-2-(4-pyridinyl)ethenyl]benzoic acid (36 mg, 0.16 mmol; see Preparation 9 above) and NMM (0.30 mL, dry) were added at room temperature with stirring. The reaction mixture was left stirring at room temperature overnight. The product was purified by HPLC (no work up required) to give title compound as yellow solid (33 mg, 34%), with no distinct melting point.

$^1$H NMR (DMSO-$d_6$): 10.38 (1H, s), 9.94 (1H, s), 9.28 (1H, br, TFA), 8.15 (1H, t, J=5.8 Hz), 8.03 (2H, d, J=8.4 Hz), 7.89 (1H, d, J=4.9 Hz), 7.85 (2H, d, J=11.6 Hz), 7.53 (2H, d, J=16.4 Hz), 7.33 (1H, d, J=1.5 Hz), 7.18 (1H, d, J=1.5 Hz), 7.12 (1H, d, J=1.5 Hz), 6.96 (1H, d, J=1.5 Hz), 3.87 (3H, s), 3.82 (3H, s), 3.25 (2H, q, J=6.1 Hz), 3.06 (2H, m), 2.79 (6H, d, J=4.8 Hz), 1.84 (2H, quintet, J=6.7 Hz).

IR (KBr): 1623, 1638, 1679, 3000, 3430 cm$^{-1}$.

HRFABMS: found: 554.2882 Calculated for $C_{31}H_{36}N_7O_3$ 554.2880.

Example 8

N-[5-({[5-({[3-(Dimethylamino)propyl]amino}carbonyl)-1-methyl-1H-pyrrol-3-yl]amino}carbonyl)-1-methyl-1H-pyrrol-3-yl]-1-methyl-4-[(E)-2-(4-nitrophenyl)-ethenyl]-1H-pyrrole-2-carboxamide trifluoro acetate salt To 1-methyl-4-[(E)-2-(4-nitrophenyl)ethenyl]-1H-pyrrole-2-carboxylic acid (40 mg, 0.146 mmol; see Preparation 8 above) and HBTU (111 mg, 0.292 mmol) were added to a DMF (1.5 mL) solution of 4-{[(4-amino-1-methyl-1H-pyrrol-2-yl)carbonyl]amino}-N-[3-(dimethyl-amino)propyl]-1-methyl-1H-pyrrole-2-carboxamide (41 mg, 0.146 mmol; see Preparation 2 above) at room temperature with stirring. The reaction mixture was left at room temperature overnight then purified by HPLC without the need to the work up. Fractions containing the required material were collected and freeze-dried to give the title compound as an orange solid (15.1 mg, 15%) with no distinct melting point.

$^1$H NMR (DMSO-$d_6$): 10.03 (1H, s), 9.91 (1H, s), 9.21 (1H, br), 8.19 (2H, d, J=8.8 Hz), 8.14 (1H, t, J=5.5 Hz), 7.75 (2H, d, J=8.8 Hz), 7.41 (1H, d, J=16.2 Hz), 7.31 (1H, d, J=1.5 Hz), 7.23 (2H, d, J=1.5 Hz), 7.17 (1H, d, J=1.5 Hz), 7.07 (1H, d, J=1.5 Hz), 6.95 (1H, d, J=1.5 Hz), 6.94 (1H, d, J=16.2 Hz), 3.90 (3H, s), 3.86 (3H, s), 3.82 (3H, s), 3.25 (2H, q, 5.9 Hz), 3.06 (2H, m), 2.79 (6H, d, J=4.5 Hz), 1.90 (2H, quintet, J=7.7 Hz).

IR (KBr): 1663, 1551, 1401, 1288, 1202, 750 cm$^{-1}$.

HRFABMS: Found: 601.2888 calculated for $C_{31}H_{37}N_8O_5$ 601.2887.

Example 9

N-[3-(Dimethylamino)propyl]-5-isopentyl-2-({[1-methyl-4-({4-[(E)-2-(3-quinolinyl)ethenyl]benzoyl}amino)-1H-pyrrol-2-yl]carbonyl}amino)-1,3-thiazole-4-carboxamide, trifluoroacetate salt To 4-{[(4-amino-1-methyl-1H-pyrrol-2-yl)carbonyl]amino}-N-[3-(dimethylamino)propyl]-1-methyl-1H-pyrrole-2-carboxamide (49 mg, 0.118 mmol; see Preparation 2 above) in DMF (1 mL), HBTU (90 mg, 0.188 mmol), 4-[(E)-2-(3-quinolinyl)ethenyl]benzoic acid (33 mg, 0.188 mmol; see Preparation 5) were added at room temperature with stirring. The reaction mixture was left standing at room temperature overnight. The product was purified by HPLC (no work up required) to give the title compound as a yellow solid (21 mg, 31%) with no distinct melting point.

$^1$H NMR (DMSO-$d_6$): 12.11 (1H, s), 10.45 (1H, s), 9.33 (1H, br), 9.28 (1H, d, J=2.0 Hz), 8.59 (1H, d, J=2.0 Hz), 8.03 (4H, m), 7.96 (1H, t, J=6.2 Hz), 7.83 (2H, d, J=8.4 Hz), 7.77 (1H, t, J=7.1 Hz), 7.65 (3H, m), 7.54 (1H, d, J=1.5 Hz), 7.46 (1H, d, J=1.5 Hz), 3.92 (3H, s), 3.36 (2H, q, J=6.4 Hz), 3.19 (2H, t, J=7.7 Hz), 3.06 (2H, m), 2.80 (6H, d, J=4.8 Hz), 1.84 (2H, quintet, J=6.7 Hz), 1.63-1.50 (3H, m), 0.93 (6H, d, J=6.3 Hz).

IR (KBr): 1681, 1642, 1581, 1540, 1464, 1435, 1404, 1266, 1202, 1134 cm$^{-1}$.

HRFABMS: Found: 678.3228 calculated for $C_{38}H_{44}N_7O_3S$ 678.3226.

Example 10

1-Methyl-N-[1-methyl-5-({[1-methyl-5-({[2-(4-morpholinyl)ethyl]amino}-carbonyl)-1H-pyrrol-3-yl]amino}carbonyl)-1H-pyrrol-3-yl]-4-[(E)-2-(3-quinolinyl)ethenyl]-1H-pyrrole-2-carboxamide, trifluoroacetate salt To 4-amino-1-methyl-N-[1-methyl-5-({[2-(4-morpholinyl)ethyl]amino}-carbonyl)-1H-pyrrol-3-yl]-1H-pyrrole-2-carboxamide (46 mg, 0.124 mmol; see Preparation 1 above) in DMF (1 mL) was added HBTU (83 mg, 0.22 mmol), 1-methyl-4-[(E)-2-(3-quinolinyl)ethenyl]-1H-pyrrole-2-carboxylic acid (31 mg, 0.11 mmol; see Preparation 12 above) and 4-methylmorpholine (25 μL, 0.22 mmol), and the resulting solution was allowed to stir for 16 h before being purified by HPLC, and the product fractions freeze dried to yield the title compound as an orange solid (0.023 g, 26%).

m.p.=No distinct m.p.

$v_{max}$ NaCl/cm$^{-1}$: 3404 υ(N—H), 3118 υ(N-Me), 2926 υ(Ar—H), 1676, 1616 υ(C=O), 1553, 1465 υ(C=C), 1257 υ(C—N) 1132 υ(C—O—C), 720 δ(C—H).

$δ_H$ $^1$H(CDCl$_3$): 3.18 (2H, m, CH$_2$), 3.38 (2H, m, CH$_2$), 3.56 (4H, m, CH$_2$), 3.83 (3H, s, NMe), 3.87 (3H, s, NMe), 3.91 (3H, s, NMe), 4.00 (2H, m, CH$_2$), 7.00 (2H, m, Ar—H and (CH=CH)), 7.08 (1H, d, Ar—H (J=1.6 Hz)), 7.21 (1H, d, Ar—H (J=1.6 Hz)), 7.25 (3H, m, Ar—H), 7.42 (1H, d, (CH=CH) (J=16.4 Hz)), 7.62 (1H, t, Ar—H (J=7.2 Hz)), 7.72 (1H, t, Ar—H (J=7.2 Hz)), 7.98 (2H, m, Ar—H), 8.25 (1H, t, NH (J=5.6 Hz)), 8.43 (1H, s, Ar—H), 9.16 (1H, s, Ar—H), 9.86 (1H, s (H)N$^+$), 9.96 (1H, s, NH), 10.04 (1H, s, NH).

HRFABMS: Found 635.3083 calculated for $C_{35}H_{39}N_8O_4$ 635.3094.

Example 11

1-Methyl-N-[1-methyl-5-({[2-(4-morpholinyl)ethyl]amino}carbonyl)-1H-pyrrol-3-yl]-4-[({1-methyl-4-[(E)-2-(2-quinolinyl)ethenyl]-1H-pyrrol-2-yl}carbonyl)-amino]-1H-pyrrole-2-carboxamide, trifluoroacetate salt To 4-amino-1-methyl-N-[1-methyl-5-({[2-(4-morpholinyl)ethyl]amino}-carbonyl)-1H-pyrrol-3-yl]-1H-pyrrole-2-carboxamide (46 mg, 0.124 mmol; see Preparation 1 above) in DMF (1 mL) was added HBTU (83 mg, 0.22 mmol), 1-methyl-4-[(E)-2-(2-quinolinyl)ethenyl]-1H-pyrrole-2-carboxylic acid (31 mg, 0.11 mmol; see Preparation 13 above) and 4-methylmorpholine (25 μL, 0.22 mmol), the resulting solution was allowed to stir for 16 h before being purified by HPLC and the product fractions freeze dried to yield the title compound (0.027 g, 26%).

m.p. No distinct m.p.

$v_{max}$ NaCl/cm$^{-1}$: 3407 υ(N—H), 3122 υ(N-Me), 2924 υ(Ar—H), 1678, 1619 υ(C=O), 155, 1464 υ(C=C), 1247 υ(C—N) 1131 υ(C—O—C), 722 δ(C—H).

$δ_H$ $^1$H(CDCl$_3$): 3.17 (2H, m, CH$_2$), 3.39 (2H, m, CH$_2$), 3.57 (4H, m, CH$_2$), 3.82 (3H, s, NMe), 3.85 (3H, s, NMe), 3.90 (3H, s, NMe), 4.00 (2H, m, CH$_2$), 7.00 (1H, d, Ar—H (J=1.6 Hz)), 7.10 (2H, m, Ar—H and (H)C=CH), 7.21 (1H, d, Ar—H (J=1.6 Hz)), 7.27 (1H, d, Ar—H (J=1.6 Hz)), 7.34 (1H, d, Ar—H (J=1.6 Hz)), 7.45 (1H, d, Ar—H (J=1.6 Hz)), 7.62 (2H, m, Ar—H), 7.83 (2H, m, Ar—H), 8.02 (3H, m, Ar—H), 8.25 (1H, t, N—H (J=5.6 Hz)), 8.50 (1H, s, NH$^+$), 9.89 (1H, s NH$^+$), 9.97 (1H, s, NH), 10.12 (1H, s, NH).

LREIMS: Found 635.27 calculated for $C_{35}H_{41}N_8O_4$ 635.31.

Example 12

N-[1-Methyl-5-({[1-methyl-5-({[2-(4-morpholinyl)ethyl]amino}carbonyl)-1H-pyrrol-3-yl]amino}carbonyl)-1H-pyrrol-3-yl]-2-[(E)-2-(2-quinolinyl)ethenyl]-1,3-thiazole-4-carboxamide, trifluoroacetate salt To 4-amino-1-methyl-N-[1-methyl-5-({[2-(4-morpholinyl)ethyl]amino}-carbonyl)-1H-pyrrol-3-yl]-1H-pyrrole-2-carboxamide (50 mg, 0.12 mmol; see Preparation 1 above) in DMF (1 mL) was added HBTU (83 mg, 0.22 mmol), 2-[(E)-2-(2-quinolinyl)ethenyl]-1,3-thiazole-4-carboxylic acid (35 mg, 0.12 mmol; see Preparation 14 above) and 4-methylmorpholine (25 μL, 0.22 mmol) and the resulting solution was allowed to stir for 16 h before being purified by HPLC and the product fractions freeze dried to yield the title compound (0.020 g, 21%).

m.p.=No distinct m.p.

$v_{max}$ NaCl/cm$^{-1}$: 3421υ(N—H), 3116 υ(N-Me), 2928 υ(Ar—H), 1677, 1647, 1638 υ(C=O), 1556, 1465 υ(C=C), 1241 υ(C—N) 1204, 1131 υ(C—O—C), 722 δ(C—H).

$δ_H$ $^1$H(CDCl$_3$): 3.17 (2H, m, CH$_2$), 3.39 (2H, m, CH$_2$), 3.57 (4H, m, CH$_2$), 3.84 (3H, s, NMe), 3.88 (3H, s, NMe), 4.00 (2H, m, CH$_2$), 7.00 (1H, d, Ar—H (J=1.6 Hz)), 7.22 (2H, m, Ar—H), 7.35 (1H, d, Ar—H (J=1.6 Hz)), 7.63 (1H, t, Ar—H (J=6.9 Hz)), 7.80 (1H, t, Ar—H (J=6.9 Hz)), 7.90 (1H, d, (H)C=CH (J=16.2 Hz)), 7.96 (1H, d, Ar—H (J=8.6 Hz)), 8.01 (2H, m, Ar—H), 8.09 (1H, d, (H)C=CH (J=16.2 Hz)), 8.24 (1H, t N—H (J=5.6 Hz)), 8.40 (1H, s, Ar—H), 8.45 (1H, d, Ar—H (J=8.6 Hz)), 9.66 (1H, s, NH$^+$), 9.98 (1H, s, N—H), 10.39 (1H, s, N—H), MS m/z calcd for M 634.30, Found 635.27 (M+H).

LREIMS: Found 639.20 calculated for C$_{33}$H$_{35}$N$_8$O$_4$S 639.25.

Example 13

1-Methyl-N-[1-methyl-5-({[2-(4-morpholinyl)ethyl] amino}carbonyl)-1H-pyrrol-3-yl]-4-({4-[(E)-2-(2-naphthyl)ethenyl]benzoyl}amino)-1H-pyrrole-2-carboxamide, trifluoroacetate salt To 4-amino-1-methyl-N-[1-methyl-5-({[2-(4-morpholinyl)ethyl]amino}-carbonyl)-1H-pyrrol-3-yl]-1H-pyrrole-2-carboxamide (46 mg, 0.124 mmol; see Preparation 1 above) in DMF (1 mL), 4-[(E)-2-(2-naphthyl)ethenyl]benzoic acid sodium salt (37 mg, 0.124 mmol; see Preparation 17 above) and HBTU (94 mg, 0.248 mmol) were added at room temperature with stirring. The reaction mixture was left standing at room temperature overnight. The product was purified by HPLC (no work up required) to give the title compound as a pale yellow solid after freeze-drying (20 mg, 22%) with no distinct melting point.

$^1$H NMR (DMSO-d$_6$): 10.33 (1H, s), 9.97 (1H, s), 9.5 (1H, br), 8.22 (1H, t, J=4.5 Hz), 8.06 (1H, s), 8.00-7.92 (6H, m), 7.81 (2H, d, J=8.4 Hz), 7.60-7.47 (4H, m), 7.34 (1H, d, J=1.6 Hz), 7.21 (1H, d, J=1.6 Hz), 7.13 (1H, d, J=1.6 Hz), 7.01 (1H, d, J=1.6 Hz), 4.02 (2H, m), 3.90 (3H, s), 3.84 (3H, s), 3.72-3.54 (6, m), 3.28-3.12 (4H, m).

IR (KBr): 1681, 1642, 1581, 1540, 1464, 1435, 1404, 1266, 1202, 1134 cm$^{-1}$.

HRFABMS: Found: 631.3030 calculated for C$_{37}$H$_{39}$N$_6$O$_4$ 631.3028.

Example 14

4-[(4-{(E)-2-[2-(1H-1,23-Benzotriazol-1-yloxy)-3-quinolinyl]ethenyl}benzoyl)-amino]-1-methyl-N-[1-methyl-5-({[2-(4-morpholinyl)ethyl] amino}carbonyl)-1H-pyrrol-3-yl]-1H-pyrrole-2-carboxamide, trifluoroacetate salt To 4-amino-1-methyl-N-[1-methyl-5-({[2-(4-morpholinyl)ethyl]amino}-carbonyl)-1H-pyrrol-3-yl]-1H-pyrrole-2-carboxamide (46 mg, 0.124 mmol; see Preparation 1 above) in DMF (1 mL), 4-[(E)-2-(2-chloro-3-quinolinyl)ethenyl] benzoic acid (38 mg, 0.124 mmol; see Preparation 16 above) and HBTU (94 mg, 0.248 mmol) were added at room temperature with stirring. The reaction mixture was left standing at room temperature overnight. The product was purified by HPLC (no work up required) to give the title compound as a pale yellow solid after freeze-drying (19 mg, 17%) with no distinct melting point.

$^1$H NMR (DMSO-d$_6$): 10.39 (1H, s), 9.97 (1H, s), 9.55 (1H, s), 9.03 (1H, s), 8.24 (2H, d, J=8.3 Hz), 8.08-8.02 (3H, m), 7.93-7.89 (2H, m), 7.85-7.77 (3H, m), 7.66-7.54 (4H, m), 7.37 (1H, d, J=7.8 Hz), 7.34 (1H, d, J=1.6 Hz), 7.21 (1H, d, J=1.6 Hz), 7.14 (1H, d, J=1.6 Hz), 7.01 (1H, d, J=1.6 Hz), 4.02 (2H, m), 3.88 (3H, s), 3.86 (3H, s), 3.69-3.53 (6H, m), 3.27-3.14 (4H, m).

IR (KBr): 1681, 1642, 1581, 1540, 1464, 1435, 1404, 1266, 1202, 1134 cm$^{-1}$.

HRFABMS: Found: 765.3267 calculated for C$_{42}$H$_{41}$N$_{10}$O$_5$ 765.3261.

Example 15

1-Methyl-N-[1-methyl-5-({[2-(4-morpholinyl)ethyl] amino}carbonyl-1H-pyrrol-3-yl]-4-({4-[(E)-2-(2-quinolinyl)ethenyl]benzoyl}amino)-1H-pyrrole-2-carboxamide, trifluoroacetate salt To 4-amino-1-methyl-N-[1-methyl-5-({[2-(4-morpholinyl)ethyl]amino}-carbonyl)-1H-pyrrol-3-yl]-1H-pyrrole-2-carboxamide (46 mg, 0.124 mmol; see Preparation 1 above) in DMF (1 mL), 4-[(E)-2-(2-quinolinyl)ethenyl]benzoic acid (34 mg, 0.124 mmol; see Preparation 15 above) and HBTU (94 mg, 0.248 mmol) were added at room temperature with stirring. The reaction mixture was left standing at room temperature overnight. The product was purified by HPLC (no work up required) to give the title compound as a pale yellow solid after freeze-drying (16 mg, 20%) with no distinct melting point.

$^1$H NMR (DMSO-d$_6$): 10.39 (1H, s), 10.08 (1H, br), 9.99 (1H, s), 8.42 (1H, d, 8.7 Hz), 8.27 (1H, t, unresolved), 8.03-7.88 (8H, m), 7.78 (1H, t, J=7.0 Hz), 7.65-7.57 (2H, m), 7.35 (1H, d, J=1.6H), 7.23 (1H, d, J=1.6 Hz), 7.13 (1H, s), 6.99 (1H, d, J=1.6 Hz), 4.01 (2H, m), 3.88 (3H, s), 3.83 (3H, s), 3.75-3.69 (4H, m), 3.60-3.40 (6H, m).

IR (KBr): 1681, 1642, 1581, 1540, 1464, 1435, 1404, 1266, 1202, 1134 cm$^{-1}$.

HRFABMS: Found: 632.2996 calculated for C$_{38}$N$_7$O$_4$ 632.2985.

Example 16

5-Isopentyl-2-({[1-methyl-4-({4-[(E)-2-(3-quinolinyl)ethenyl]benzoyl}amino)-1H-pyrrol-2-yl] carbonyl}amino)-N-[2-(4-morpholinyl)ethyl]-1,3-thiazole-4-carboxamide, trifluoroacetate salt To 2-{[(4-amino-1-methyl-1H-pyrrol-2-yl)carbonyl] amino}-5-isopentyl-N-[2-(4-morpholinyl)ethyl]-1,3-thiazole-4-carboxamide (75 mg, 0.167 mmol; see Preparation 18 above) in DMF (1 mL), 4-[(E)-2-(3-quinolinyl)ethenyl]benzoic acid (46 mg, 0.167 mmol; see Preparation 5 above) and HBTU (126 mg, 0.334 mmol) were added at room temperature with stirring. The reaction mixture was left standing at room temperature overnight. The product was purified by HPLC (no work up required) to give the title compound as a pale yellow solid after freeze-drying (33 mg, 24%) with no distinct melting point.

$^1$H NMR (DMSO-d$_6$): 12.09 (1H, s), 10.46 (1H, s), 9.71 (1H, br), 9.28 (1H, d, J=1.6 Hz), 8.58 (1H, s), 8.10 (1H, t, J=5.8 Hz), 8.03 (4H, m), 7.83 (2H, d, J=8.4 Hz), 7.77 (1H, dt, J=8.2 Hz & J=1.4 Hz), 7.71-7.60 (3H, m), 7.54 (1H, d, J=1.6 Hz), 7.45 (1H, d, J=1.6 Hz), 4.02 (2H, m), 3.93 (3H, s), 3.70-3.54 (6H, m), 3.31-3.15 (6H, m), 1.64-1.51 (3H, m), 0.93 (6H, d, J=6.3 Hz).

IR (KBr): 1671, 1552, 1288, 1202, 1134, 834, 799, 721 cm$^{-1}$.

HRFABMS: Found: 706.3179 calculated for C$_{39}$H$_{44}$O$_4$N$_7$S 706.3176.

Example 17

2-({[4-({[(E)-2-(2-Chloro-3-quinolinyl)ethenyl]benzoyl}amino)-1-methyl-1H-pyrrol-2-yl]carbonyl}amino)-5-isopentyl-N-[2-(4-morpholinyl)ethyl]-1,3-thiazole-4-carboxamide, trifluoroacetate salt To 2-{[(4-amino-1-methyl-1H-pyrrol-2-yl)carbonyl]amino}-5-isopentyl-N-[2-(4-morpholinyl)ethyl]-1,3-thiazole-4-carboxamide (75 mg, 0.167 mmol; see Preparation 18 above) in DMF (1 mL), 4-[(E)-2-(2-Naphthyl)ethenyl]benzoic acid sodium salt (46 mg, 0.167 mmol; see Preparation 16 above) and HBTU (126 mg, 0.334 mmol) were added at room temperature with stirring. The reaction mixture was left standing at room temperature overnight. The product was purified by HPLC (no work up required) to give the title compound as a pale yellow solid after freeze-drying (12 mg, 9%) with no distinct melting point.

$^1$H NMR (DMSO-d$_6$): 12.08 (1H, s), 10.49 (1H, s), 9.72 (1H, br), 9.03 (1H, s), 8.24 (1H, d, J=8.4 Hz), 8.08-7.99 (3H, m), 7.94-7.88 (1H, m), 7.85-7.79 (2H, m), 7.66-7.56 (3H, m), 7.54 (1H, d, J=1.6 Hz), 7.46 (1H, d, J=1.6 Hz), 7.37 (1H, d, J=7.9 Hz), 4.02 (2H, m), 3.93 (3H, s), 3.70-3.54 (6H, m), 3.31-3.15 (6H, m), 1.64-1.51 (3H, m), 0.93 (6H, d, J=6.3 Hz).

IR (KBr): 1663, 1551, 1502, 1401, 1288, 1202, 1137, 778, 750 cm$^{-1}$.

HRFABMS: Found: 740.2786 calculated for C$_{39}$H$_{43}$O$_4$N$_7$$^{35}$ClS 740.2737.

Example 18

2-[({4-[(4-{(E)-2-[2-(1H-1,2,3-Benzotriazol-1-yloxy)-3-quinolinyl]ethenyl}-benzoyl)amino]-1-methyl-1H-pyrrol-2-yl}carbonyl)amino]-5-isopentyl-N-[2-(4-morpholinyl)ethyl]-1,3-thiazole-4-carboxamide, trifluoroacetate salt The title compound was isolated, by HPLC purification of the reaction mixture described in Example 17 above, as a yellow solid (19 mg, 12%) with no distinct melting point.

$^1$H NMR (DMSO-d$_6$): 12.09 (1H, s), 10.49 (1H, s), 9.68 (1H, br), 9.03 (1H, s), 8.93 (1H, s), 8.23 (1H, d, J=8.4 Hz), 8.09-7.95 (6H, m), 7.90-7.77 (6H, m), 7.70 (1H, t, J=7.0 Hz), 7.65-7.57 (4H, m), 7.55 (1H, d, J=1.6 Hz), 7.46 (1H, d, J=1.6 Hz), 7.37 (1H, d, J=9.1 Hz), 12.08 (1H, s), 10.49 (1H, s), 9.72 (1H, br), 9.03 (1H, s), 8.24 (1H, d, J=8.4 Hz), 8.08-7.99 (3H, m), 7.94-7.88 (1H, m), 7.85-7.79 (2H, m), 7.66-7.56 (3H, m), 7.54 (1H, d, J=1.6 Hz), 7.46 (1H, d, J=1.6 Hz), 7.37 (1H, d, J=7.9 Hz), 4.02 (2H, m), 3.93 (3H, s), 3.70-3.54 (6H, m), 3.31-3.15 (6H, m), 1.64-1.51 (3H, m), 0.93 (6H, d, J=6.3 Hz).

IR (KBr): 1663, 1551, 1502, 1401, 1288, 1202, 1137, 778, 750 cm$^{-1}$.

HRFABMS: Found: 839.3455 calculated for C$_{45}$H$_{47}$O$_5$N$_{10}$S 839.3452.

Example 19

5-Isopentyl-2-({[1-methyl-4-({4-[(E)-2-(2-quinolinyl)ethenyl]benzoyl}amino)-1H-pyrrol-2-yl]carbonyl}amino)-N-[2-(4-morpholinyl)ethyl]-1,3-thiazole-4-carboxamide, trifluoroacetate salt To 2-{[(4-amino-1-methyl-1H-pyrrol-2-yl)carbonyl]amino}-5-isopentyl-N-[2-(4-morpholinyl)ethyl]-1,3-thiazole-4-carboxamide (75 mg, 0.167 mmol; see Preparation 18 above) in DMF (1 mL), 4-[(E)-2-(2-chloro-3-quinolinyl)ethenyl]benzoic acid (46 mg, 0.167 mmol; see Preparation 15 above) and HBTU (126 mg, 0.334 mmol) were added at room temperature with stirring. The reaction mixture was left standing at room temperature overnight. The title compound was purified by HPLC (no work up required) to give the desired material as an orange solid after freeze-drying (25 mg, 18%) with no distinct melting point.

$^1$H NMR (DMSO-d$_6$): 12.09 (1H, s), 10.49 (1H, s), 9.82 (1H, br), 8.45 (1H, d, J=8.6 Hz), 8.11 (1H, t, J=5.7 Hz), 8.05 (2H, d, J=8.3 Hz), 8.00-7.93 (4H, m), 7.92 (2H, d, J=8.4 Hz), 7.79 (1H, dd, J=8.3 & J=1.3 Hz), 7.62 (2H, m), 7.55 (1H, d, J=1.6 Hz), 7.45 (1H, d, J=1.6 Hz), 4.02 (3H, m), 3.93 (3H, s), 3.71 (3H, m), 3.56 (2H, m), 3.30 (2H, m), 3.22-3.14 (4H, m), 1.63-1.51 (3H, m), 0.93 (6H, d, J=6.4 Hz).

IR (KBr): 1663, 1551, 1502, 1401, 1288, 1202, 1137, 778, 750 cm$^{-1}$.

HRFABMS: Found: 706.3180 calculated for C$_{39}$H$_{44}$O$_4$N$_7$S 706.3175.

Example 20

5-Isopentyl-2-({[1-methyl-4-({4-[(E)-2-(2-naphthyl)ethenyl]benzoyl}amino)-1H-pyrrol-2-yl]carbonyl}amino)-N-[2-(4-morpholinyl)ethyl]-1,3-thiazole-4-carboxamide, trifluoroacetate salt To 2-{[(4-amino-1-methyl-1H-pyrrol-2-yl)carbonyl]amino}-5-isopentyl-N-[2-(4-morpholinyl)ethyl]-1,3-thiazole-4-carboxamide (75 mg, 0.167 mmol; see Preparation 18 above) in DMF (1 mL), 4-[(E)-2-(2-naphthyl)ethenyl]benzoic acid sodium salt (50 mg, 0.167 mmol; see Preparation 17 above) and HBTU (126 mg, 0.334 mmol) were added at room temperature with stirring. The reaction mixture was left standing at room temperature overnight. The title compound was purified by HPLC (no work up required) to give the desired material as a pale solid after freeze-drying (19 mg, 14%) with no distinct melting point.

$^1$H NMR (DMSO-d$_6$): 12.08 (1H, s), 10.43 (1H, s), 9.59 (1H, br), 8.10-8.07 (2H, m), 8.01 (2H, d, J=8.4 Hz), 7.94-7.91 (4H, m), 7.81 (2H, d, J=8.4 Hz), 7.55-7.45 (6H, m), 4.02 (3H, m), 3.93 (3H, s), 3.66 (3H, m), 3.57 (2H, m), 3.30 (2H, m), 3.22-3.15 (4H, m), 1.63-1.51 (3H, m), 0.93 (6H, d, J=6.4 Hz).

IR (KBr): 1663, 1551, 1502, 1401, 1288, 1202, 1137, 778, 750 cm$^{-1}$.

HRFABMS: Found: 705.3221 calculated for C$_{40}$H$_{45}$O$_4$N$_6$S 705.3223.

Example 21

5-Isopentyl-2-[({1-methyl-4-[({1-methyl-4-[(E)-2-(4-nitrophenyl)ethenyl]-1H-pyrrol-2-yl}carbonyl)amino]-1H-pyrrol-2-yl}carbonyl)amino]-N-[2-(4-morpholinyl)ethyl]-1,3-thiazole-4-carboxamide, trifluoroacetate salt To 2-{[(4-amino-1-methyl-1H-pyrrol-2-yl)carbonyl]amino}-5-isopentyl-N-[2-(4-morpholinyl)ethyl]-1,3-thiazole-4-carboxamide (75 mg, 0.167 mmol; see Preparation 18 above) in DMF (1 mL), 1-methyl-4-[(E)-2-(4-nitrophenyl)ethenyl]-1H-pyrrole-2-carboxylic acid (46 mg, 0.167 mmol; see Preparation 8 above) and HBTU (126 mg, 0.334 mmol) were added at room temperature with stirring. The reaction mixture was left standing at room temperature overnight. The product was purified by HPLC (no work up required) to give the title compound as an orange solid after freeze-drying (19 mg, 14%) with no distinct melting point.

¹H NMR (DMSO-d₆): 12.05 (1H, s), 10.15 (1H, s), 9.78 (1H, br), 8.20 (2H, d, J=8.8 Hz), 8.09 (1H, t, J=5.7 Hz), 7.76 (2H, d, J=8.8 Hz), 7.46 (1H, d, J=1.6 Hz), 7.41 (1H, d, J=16.3 Hz), 7.39 (1H, d, J=1.6 Hz), 7.32 (1H, d, J=1.6 Hz), 7.27 (1H, J=1.6 Hz), 6.95 (1H, d, J=16.3 Hz), 4.02 (3H, m), 3.90 (6H, s), 3.66 (3H, m), 3.57 (2H, m), 3.30 (2H, m), 3.22-3.15 (4H, m), 1.63-1.51 (3H, m), 0.93 (6H, d, J=6.4 Hz).

IR (KBr): 1663, 1551, 1502, 1401, 1288, 1202, 1137, 778, 750 cm⁻¹.

HRFABMS: Found: 702.2950 calculated for $C_{35}H_{42}O_6N_8S$ 702.2948.

Example 22

6-[(E)-2-(4-Methoxyphenyl)ethenyl]-N-[1-methyl-5-({[1-methyl-5-({[2-(4-morpholinyl)ethyl]amino}carbonyl-1H-pyrrol-3-yl]amino}carbonyl)-1H-pyrrol-3-yl]nicotinamide, trifluoroacetate salt (i) 4-Amino-1-methyl-N-[1-methyl-5-({[3-(4-morpholinyl)ethyl]amino}-carbonyl)-1H-pyrrol-3-yl]-1H-pyrrole-2-carboxamide 1-Methyl-4-{[(1-methyl-4-nitro-1H-pyrrol-2-yl)carbonyl]amino}-N-[2-(4-morpholinyl)ethyl]-1H-pyrrole-2-carboxamide (200 mg, 0.495 mmol; see Preparation 1(iv) above) was dissolved in methanol (25 mL) at 0° C. under nitrogen. Pd/C-10% (170 mg) was added portionwise with stirring under nitrogen at 0° C. The reaction mixture was hydrogenated for 4 h at room temperature and atmospheric pressure. The catalyst was removed over Kieselguhr and the solvent was removed under reduced pressure to give the sub-title compound. This was dissolved in DMF (1 mL, dry) and divided into four equal portions that were used, without further purification, to prepare the title compounds of Examples 22 to 25.

(ii) 6-[(E)-2-(4-Methoxyphenyl)ethenyl]-N-[1-methyl-5-({[1-methyl-5-({[2-(4-morpholinyl)ethyl]amino}carbonyl)-1H-pyrrol-3-yl]amino}carbonyl)-1H-pyrrol-3-yl]nicotinamide, trifluoroacetate salt To the first portion of DMF solution obtained from step (i) above, the following were added at room temperature with stirring: HBTU (94 mg, 0.248 mmol) and 6-[(E)-2-(4-methoxyphenyl)ethenyl]nicotinic acid (32 mg, 0.124 mmol; see Preparation 21 above). The reaction mixture was left stirring at room temperature overnight, then the product was purified by HPLC to give the title compound as an orange solid (29 mg, 32%) with no distinct melting point.

IR (KBr): 3427, 1673, 1588, 1402, 1253, 1202, 1174, 832, 720 cm⁻¹.

¹H NMR (DMSO-d₆): 10.48 (1H, s), 9.98 (2H, s & br), 9.07 (1H, s), 8.28 (1H, d, J=2.3 Hz), 8.26 (1H, d, J=2.3 Hz), 7.77 (1H, d, J=16.0 Hz), 7.67 (31H, d, J=8.8 Hz), 7.35 (1H, d, J=1.6 Hz), 7.27 (1H, d, J=16.0 Hz), 7.22 (1H, d, J=1.6 Hz), 7.12 (1H, d, J=1.6 Hz), 7.01 (3H, m), 4.01 (2H, m), 3.88 (3H, s), 3.83 (3H, s), 3.80 (3H, s), 3.73 (2H, m), 3.56 (4H, m), 3.27 (2H, m), 2.99 (2H, m).

HRFABMS: Found: 611.2990 calculated for $C_{34}H_{39}O_5N_6$ 611.2982.

Example 23

2-[(E)-2-(4-Methoxyphenyl)ethenyl]-N-[1-methyl-5-({[1-methyl-5-({[2-(4-morpholinyl)ethyl]amino}carbonyl)-1H-pyrrol-3-yl]amino}carbonyl)-1H-pyrrol-3-yl]-6-quinolinecarboxamide, trifluoroacetate salt To the second portion of DMF solution obtained from Example 22, step (i) above, the following were added at room temperature with stirring: HBTU (94 mg, 0.248 mmol) and 2-[(E)-2-(4-methoxyphenyl)ethenyl]-6-quinolinecarboxylic acid (38 mg, 0.124 mmol; see Preparation 22 above). The reaction mixture was left stirring at room temperature overnight, then the product was purified by HPLC to give the title compound as an orange solid (60 mg, 63%) with no distinct melting point.

IR (KBr): 3422, 1672, 1583, 1514, 1249, 1203, 1173, 1133, 833, 720 cm⁻¹.

¹H NMR (DMSO-d₆): 10.58 (1H, s), 10.00 (1H, s), 9.84 (1H, br), 8.55 (1H, d, J=1.6 Hz), 8.53 (1H, d, J=8.7 Hz), 8.28 (2H, m), 8.09 (1H, d, J=8.8 Hz), 7.98 (1H, d, J=8.7 Hz), 7.94 (1H, d, J=16.2 Hz), 7.73 (2H, d, J=8.6 Hz), 7.41 (1H, t, J=4.6 Hz), 7.38 (1H, d, J=1.6 Hz), 7.23 (1H, d, J=1.6 Hz), 7.16 (1H, d, J=1.6 Hz), 7.04 (3H, m), 4.02 (2H, m), 3.89 (31H, s), 3.84 (3H, s), 3.82 (31H, s), 3.73 (2H, m), 3.56 (4H, m), 3.27 (2H, m), 3.14 (2H, m).

HRFABMS: Found: 662.3089 Calculated for $C_{37}H_{40}O_5N_7$ 662.3091.

Example 24

N-[1-Methyl-5-({[1-methyl-5-({[2-(4-morpholinyl)ethyl]amino}carbonyl)-1H-pyrrol-3-yl]amino}carbonyl)-1H-pyrrol-3-yl]-2-{(E)-2-[4-(methylsulfanyl)-phenyl]ethenyl}-6-quinolinecarboxamide, trifluoroacetate salt To the third portion of DMF solution obtained from Example 22, step (i) above, the following were added at room temperature with stirring: HBTU (94 mg, 0.248 mmol) and 2-{(E)-2-[4-(methylsulfanyl)phenyl]ethenyl}-6-quinolinecarboxylic acid (40 mg, 0.124 mmol; see Preparation 20 above). The reaction mixture was left stirring at room temperature overnight, then the product was purified by HPLC to give the title compound as an orange solid (43 mg, 43%) with no distinct melting point.

IR (KBr): 3424, 1673, 1581, 1514, 1250, 1203, 1173, 1133, 833, 720 cm⁻¹.

¹H NMR (DMSO-d₆): ¹H NMR (DMSO-d₆): 10.57 (1H, s), 10.00 (1H, s), 9.67 (1H, br), 8.55 (1H, d, J=1.6 Hz), 8.50 (1H, d, J=8.7 Hz), 8.28 (2H, m), 8.09 (1H, d, J=8.8 Hz), 7.96 (1H, d, J=8.7 Hz), 7.91 (1H, d, J=16.2 Hz), 7.72 (2H, d, J=8.6 Hz), 7.50 (1H, t, J=4.6 Hz), 7.38 (1H, d, J=1.6 Hz), 7.34 (2H, d, J=8.5 Hz), 7.22 (1H, d, J=1.6 Hz), 7.16 (1H, d, J=1.6 Hz), 7.01 (1H, d, J=1.6 Hz), 4.02 (2H, m), 3.89 (3H, s), 3.84 (3H, s), 3.73 (2H, m), 3.56 (4H, m), 3.27 (2H, m), 3.14 (2H, m), 3.53 (3H, s).

HRFABMS: Found: 677.2788 Calculated for $C_{37}H_{39}N_7O_4S$ 677.2784.

Example 25

N-[1-methyl-5-({[1-methyl-5-({[2-(4-morpholinyl)ethyl]amino}carbonyl)-1H-pyrrol-3-yl]amino}carbonyl)-1H-pyrrol-3-yl]-6-{(E)-2-[4-(methylsulfanyl)-phenyl]ethenyl}nicotinamide, trifluoroacetate salt To the fourth portion of DMF solution obtained from Example 22, step (i) above, the following were added at room temperature with stirring: HBTU (94 mg, 0.248 mmol) and 6-{(E)-2-[4-(methylsulfanyl)phenyl]ethenyl}nicotinic acid (34 mg, 0.124 mmol; see Preparation 19 above). The reaction mixture was left stirring at room temperature overnight, then the product was purified by HPLC to give the title compound as an orange solid (39 mg, 42%) with no distinct melting point.

IR (KBr): 3424, 1673, 1581, 1514, 1250, 1203, 1173, 1133, 833, 720 cm$^{-1}$.

$^1$H NMR (DMSO-d$_6$): 10.49 (1H, s), 9.99 (1H, s), 9.76 (1H, br), 9.08 (1H, s), 8.29-8.24 (2H, m), 7.78 (1H, d, J=16 Hz), 7.68 (1H, d, J=8.9 Hz), 7.66 (1H, d, J=8.6 Hz), 7.36-7.29 (4H, m), 7.21 (1H, d, J=1.5 Hz), 7.11 (1H, d, J=1.5 Hz), 6.99 (1H, d, J=1.5 Hz), 4.02 (2H, m), 3.89 (3H, s), 3.84 (3H, s), 3.73 (2H, m), 3.56 (4H, m), 3.27 (2H, m), 3.14 (2H, m), 2.52 (3H, s).

HRFABMS: Found: 628.2710 Calculated for C$_{33}$H$_{38}$O$_4$N$_7$S 628.2706.

Example 26

Title compounds of the examples displayed microbicidal activity against a number of different microorganisms, as detailed in Table 1 below.

Organisms

Bacteria

| | |
|---|---|
| *Staphylococcus aureus* Strain 1 | (BSAC04(1)) (Clinical isolate from Glasgow Royal Infirmary) |
| *Staphylococcus aureus* Strain 2 | (NCTC 6571) |
| *Streptococcus faecalis* | (NCTC 775) |
| *Mycobacter fortuitum* | (NCTC 10394) |

Fungi

| | |
|---|---|
| *Candida albicans* | (NCPF3179) |
| *Aspergillus niger* | (IMI 1745) |

Example 27

Title compounds of Example 2 and Example 22 displayed microbicidal activity against a number of different strains of *Staphylococcus aureus*, as detailed in Table 2 below. BSAC03/04/05 (1)-(10) refer to collected clinical strains of *S. aureus* in the Scottish Clinical Isolates Collection.

TABLE 2

Minimum inhibitory concentrations (MICs) for title compounds of Examples 2 and 22 expressed μg/mL.

| BSAC Culture | | DRUG | |
|---|---|---|---|
| Year | Number | Example 22 | Example 2 |
| 2003 | 1 | 0.5 | 0.25 |
| 2003 | 2 | 4 | 0.25 |
| 2003 | 3 | 0.5 | 0.25 |
| 2003 | 4 | 0.5 | 0.12 |
| 2003 | 5 | 0.5 | 0.12 |
| 2003 | 6 | 1 | 0.12 |
| 2003 | 7 | 0.5 | 0.12 |
| 2003 | 8 | 0.5 | 0.06 |
| 2003 | 9 | 2 | 0.25 |
| 2003 | 10 | 0.5 | 0.25 |
| 2004 | 1 | 0.5 | 0.25 |
| 2004 | 2 | 4 | 0.5 |
| 2004 | 3 | 2 | 0.5 |
| 2004 | 4 | 2 | 0.25 |
| 2004 | 5 | 0.5 | 0.12 |
| 2004 | 6 | 0.5 | 0.25 |
| 2004 | 7 | 1 | 0.12 |
| 2004 | 8 | 1 | 0.25 |
| 2004 | 9 | 2 | 0.12 |
| 2004 | 10 | 1 | 0.12 |
| 2005 | 1 | 2 | 0.25 |
| 2005 | 2 | 8 | 1 |
| 2005 | 3 | 2 | 0.12 |
| 2005 | 4 | 0.5 | 0.25 |
| 2005 | 5 | 4 | 0.25 |
| 2005 | 6 | 0.5 | 0.12 |

TABLE 1

Minimum inhibitory concentrations (MICs) for title compounds of the examples expressed in μM and (μg/mL).

| Ex. | S aureus 1 | S. aureus 2 | St. faecalis | M. fortuitum | C. albicans | A. niger |
|---|---|---|---|---|---|---|
| 1 | 2.7 (2.0) | 11.0 (8.0) | 69 (50) | na | na | 138 (100) |
| 2 | 0.16 (0.12) | 0.32 (0.25) | 33.5 (25) | 67 (50) | 33.5 (25) | 67 (50) |
| 3 | 5.7 (4.0) | 22.9 (16.0) | 16.4 (12.5) | na | na | 143 (100) |
| 4 | 8.9 (6.25) | 17.9 (12.5) | na | na | 143 (100) | 72 (50) |
| 5 | 35 (25) | 35 (25) | 70 (50) | na | na | 70 (50) |
| 6 | nt | 72 (50) | 72 (50) | na | na | 143 (100) |
| 7 | 24 (16) | 75 (50) | 37 (25) | na | na | na |
| 8 | na | 70 (50) | 70 (50) | na | na | 140 (100) |
| 9 | na | 63 (50) | na | 126 (100) | 126 (100) | 126 (100) |
| 10 | 5.3 (4) | na | 15 (12.5) | 116 (100) | 116 (100) | na |
| 11 | 4.6 (4) | na | na | na | 134 (100) | na |
| 12 | 10 (8) | na | na | na | na | na |
| 13 | nt | 68 (50) | 136 (100) | na | na | 136 (100) |
| 14 | nt | 57 (50) | 114 (100) | na | 114 (100) | 57 (50) |
| 15 | nt | 134 (100) | na | na | 134 (100) | 134 (100) |
| 16 | nt | na | na | 122 (100) | 61 (50) | 122 (100) |
| 17 | nt | na | na | 117 (100) | 117 (100) | na |
| 18 | nt | na | na | 169 (100) | 169 (100) | na |
| 19 | nt | na | na | na | na | 122 (100) |
| 22 | 0.69 (0.5) | 17.2 (12.5) | 8.6 (6.3) | 69 (50) | 34 (25) | 69 (50) |
| 23 | 5.2 (4) | na | 32 (25) | 129 (100) | 129 (100) | 64 (50) |
| 24 | 126 (100) | 126 (100) | 26 (100) | na | 126 (100) | 126 (100) |
| 25 | 0.67 (0.5) | 67 (50) | 34 (25) | 135 (100) | 67 (50) | 135 (100) |

Key
na = not active at 100 mg/mL (i.e. MIC > 100 mg/mL)
nt = not tested

TABLE 2-continued

Minimum inhibitory concentrations (MICs) for title
compounds of Examples 2 and 22 expressed μg/mL.

| BSAC Culture | | DRUG | |
|---|---|---|---|
| Year | Number | Example 22 | Example 2 |
| 2005 | 7 | 0.5 | 0.25 |
| 2005 | 8 | 4 | 0.5 |
| 2005 | 9 | 2 | 0.25 |
| 2005 | 10 | 1 | 0.12 |

Example 28

Determination of minimal effective dose of title compound of Example 2 in *S. aureus* infection model.

Mice were infected with *S. aureus* LS-1 (50 million cfu by iv injection) and treated with graded doses of the compound of Example 2 (iv injection within 30 minutes). Each group contained 5 mice and comprised the following.

Group 1: *S. aureus* LS-1 only
Group 2: *S. aureus* LS-1 plus 60 mg/kg of the compound of Example 2
Group 3: *S. aureus* LS-1 plus 40 mg/kg of the compound of Example 2
Group 4: *S. aureus* LS-1 plus 20 mg/kg of the compound of Example 2
Group 5: *S. aureus* LS-1 plus 10 mg/kg of the compound of Example 2

Mice were assessed daily for weight loss, development of swollen joints and morbidity/mortality. The results are summarised in Tables 3 to 5.

TABLE 3

Development of swollen joints following infection

| | Days post infection | | | | | |
|---|---|---|---|---|---|---|
| | 2 | 3 | 4 | 5 | 6 | 7 |
| Group 1 | 4/20 (20) | 4/20 (20) | 6/16 (37.5) | 7/16 (44.5) | 6/16 (37.5) | 6/16 (37.5) |
| Group 2 | 0/20 (0) | 0/20 (0) | 0/16 (0) | 0/16 (0) | 0/16 (0) | 0/16 (0) |
| Group 3 | 0/20 (0) | 0/20 (0) | 2/20 (10) | 3/20 (15) | 3/20 (15) | 3/20 (15) |
| Group 4 | 1/20 (5) | 1/20 (5) | 2/20 (10) | 1/16 (6.3) | 6/20 (30) | 4/12 (33) |
| Group 5 | 1/20 (5) | 1/20 (5) | 2/20 (10) | 2/20 (10) | 5/16 (31) | 4/12 (33) |

TABLE 4

Mortality rate of mice following infection

| | Days post infection | | | | | |
|---|---|---|---|---|---|---|
| | 2 | 3 | 4 | 5 | 6 | 7 |
| Group 1 | 0/5 | 0/5 | 1/5 | 1/5 | 2/5 | 2/5 |
| Group 2 | 0/5 | 0/5 | 1/5 | 1/5 | 1/5 | 1/5 |
| Group 3 | 0/5 | 0/5 | 0/5 | 0/5 | 0/5 | 0/5 |
| Group 4 | 0/5 | 0/5 | 0/5 | 1/5 | 2/5 | 3/5 |
| Group 5 | 0/5 | 0/5 | 0/5 | 1/5 | 1/5 | 2/5 |

TABLE 5

Weight loss of mice after infection

| | Mean mouse weight (g) after | | |
|---|---|---|---|
| | Day 2 | Day 5 | Day 7 |
| Group 1 | 27.4 | 24.0 | 23.5 |
| Group 2 | 27.1 | 26.3 | 26.1 |
| Group 3 | 27.0 | 26.4 | 26.0 |
| Group 4 | 27.6 | 25.4 | 25.1 |
| Group 5 | 26.9 | 23.0 | 22.6 |

| Abbreviations | |
|---|---|
| br = | broad (in relation to NMR) |
| CE = | capillary electrophoresis |
| cfu = | colony forming units |
| d = | doublet (in relation to NMR) |
| DCM = | dichloromethane |
| DMF = | N,N-dimethylformamide |
| DMSO = | dimethylsulfoxide |
| DNA = | deoxyribose nucleic acid |
| dsDNA = | double-stranded deoxyribose nucleic acid |
| eq. = | equivalents |
| FRET = | fluorescence resonance energy transfer |
| h = | hour(s) |
| HBTU = | O-benzotriazol-1-yl-N,N,N',N'-tetramethyluronium hexafluorophosphate |
| HCl = | hydrochloric acid |
| HOBT = | 1-hydroxybenzotriazole |
| HPLC = | high performance liquid chromatography |
| HREIMS = | high resolution electron ionisation mass spectrometry |
| HRFABMS = | high resolution fast atom bombardment mass spectrometry |

-continued

| Abbreviations | |
|---|---|
| IR = | infra red (in relation to spectroscopy) |
| iv = | intravenous |
| LRESMS = | low resolution electrospray mass spectrometry |
| m = | multiplet (in relation to NMR) |
| Me = | methyl |
| min = | minute(s) |
| MIC = | minimum inhibitory concentration |
| m.p. = | melting point |
| MS = | mass spectroscopy |
| $\nu_{max}$ = | wave number (in relation to infra red spectroscopy) |
| NMM = | N-methylmorpholine |
| NMR = | nuclear magnetic resonance |
| Pd/C = | palladium on carbon |
| q = | quartet (in relation to NMR) |
| rt/RT = | room temperature |
| s = | singlet (in relation to NMR) |
| t = | triplet (in relation to NMR) |

-continued

| Abbreviations | |
|---|---|
| TEA = | triethylamine |
| THF = | tetrahydrofuran |
| TFA = | trifluoroacetic acid |

Prefixes n-, s-, i-, t- and tert- have their usual meanings: normal, secondary, iso, and tertiary.

The invention claimed is:
1. A compound of formula I,

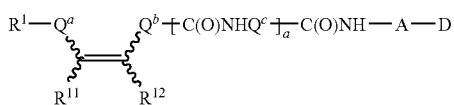

wherein
the wavy lines indicate optional cis- or trans-stereochemistry;
wherein
$R^1$ represents
H,
$R^{1a}C(O)$—NH—,
$NO_2$ or
—$N(R^{2a})R^{2b}$;
$R^{1a}$ represents
aryl (which latter group is optionally substituted by one or more substituents selected from OH, halo, cyano, nitro, $N(R^{2a})R^{2b}$, $C_{1-4}$ alkyl and $C_{1-4}$ alkoxy),
aromatic or part-aromatic $C_{13-14}$ tricyclic carbocyclyl (which latter group is optionally substituted by one or more substituents selected from OH, halo, cyano, nitro, $N(R^{2a})R^{2b}$, $C_{1-4}$ alkyl and $C_{1-4}$ alkoxy, and which latter group, if part-aromatic, is optionally substituted in the non-aromatic part by one or two oxo groups) or
$C_{1-12}$ alkyl (which latter group is optionally substituted and/or terminated by one or more substituents selected from halo and aryl (which latter group is optionally substituted by one or more substituents selected from OH, halo, cyano, nitro, $N(R^{2a})R^{2b}$, $C_{1-4}$ alkyl and $C_{1-4}$ alkoxy));
a represents 1, 2, 3 or 4;
A represents $C_{2-6}$ alkylene or
$A^1$-C(O)N(H)-$A^2$, wherein $A^2$ is attached to the group D;
$A^1$ represents $C_{1-4}$ alkylene;
$A^2$ represents $C_{2-5}$ alkylene;
D represents $Het^1$, —$N(R^{3a})R^{3b}$, —$C(=NR^{3c})N(R^{3d})R^{3e}$ or —$N(R^{3f})C(=NR^{3g})N(H)R^{3h}$;
$Het^1$ represents a four- to twelve-membered heterocyclic group containing at least one N atom and optionally one or more heteroatoms selected from N, O and S, which heterocyclic groups are optionally substituted by one or more substituents selected from =O, OH, halo, cyano, nitro, $N(R^{2a})R^{2b}$, $C_{1-4}$ alkyl and $C_{1-4}$ alkoxy;
$R^{3a}$ and $R^{3b}$ independently represent H, $C_{1-6}$ alkyl or $Het^2$;
$R^{3c}$ to $R^{3h}$ independently represent H or $C_{1-6}$ alkyl;
$Het^2$ independently represents a four- to twelve-membered heterocyclic group containing one or more heteroatoms selected from N, O and S, which heterocyclic group is optionally substituted by one or more substituents selected from =O, OH, halo, cyano, nitro, $N(R^{2a})R^{2b}$, $C_{1-4}$ alkyl and $C_{1-4}$ alkoxy;

each $Q^a$ to $Q^c$ independently represents, at each occurrence when used herein,
naphthyl (optionally substituted by one or more substituents selected from OH, halo, cyano, nitro, $N(R^{2a})R^{2b}$, $C_{1-4}$ alkyl and $C_{1-4}$ alkoxy),
$Het^3$,
or a structural fragment represented by formula Ia, Ib, Ic, Id, Ie or If,

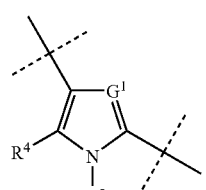

Ia

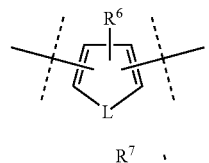

Ib

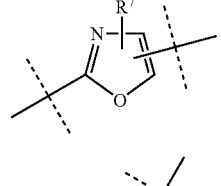

Ic

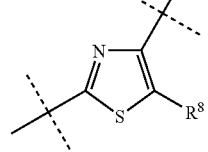

Id

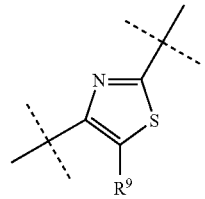

Ie

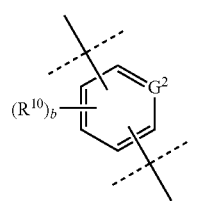

If wherein
the dashed lines indicate the positions of attachment of the fragments;
$R^4$ represents H or $C_{1-6}$ alkyl;
$R^5$ represents $C_{1-12}$ alkyl;
$R^6$, $R^7$, $R^8$ and $R^9$ independently represent H or $C_{1-12}$ alkyl;
$R^{10}$ represents, independently at each occurrence, OH, halo, cyano, nitro, $N(R^{2a})R^{2b}$, $C_{1-4}$ alkyl, —S—$C_{1-4}$ alkyl and $C_{1-4}$ alkoxy;
b represents 0, 1, 2 or 3;
$G^1$ and $G^2$ independently represent CH or N, or $G^2$ alternatively represents C—$R^{10}$;

L represents O or S;

Het$^3$ represents a nine- or ten-membered, bicyclic heterocyclic group containing one or more heteroatoms selected from N, O and S, which group is optionally substituted by one or more substituents selected from =O, halo, cyano, nitro, N(R$^{2a}$)R$^{2b}$, Het$^a$, C$_{1-4}$ alkyl and OR$^a$;

R$^a$ represents H, C$_{1-4}$ alkyl, aryl (which latter group is optionally substituted by one or more substituents selected from OH, halo, cyano, nitro, N(R$^{2a}$)R$^{2b}$, C$_{1-4}$ alkyl and C$_{1-4}$ alkoxy) or Het$^b$;

Het$^a$ and Het$^b$ independently represent four- to twelve-membered heterocyclic groups containing one or more heteroatoms selected from N, O and S, which heterocyclic groups are optionally substituted by one or more substituents selected from =O, OH, halo, cyano, nitro, N(R$^{2a}$)R$^{2b}$, C$_{1-4}$ alkyl and C$_{1-4}$ alkoxy;

R$^{11}$ and R$^{12}$ independently represent, at each occurrence when used herein, H, C$_{1-6}$ alkyl or aryl (which latter group is optionally substituted by one or more substituents selected from OH, halo, cyano, nitro, N(R$^{2a}$)R$^{2b}$, C$_{1-4}$ alkyl and C$_{1-4}$ alkoxy);

R$^{2a}$ and R$^{2b}$ independently represent, at each occurrence when used herein, H or C$_{1-4}$ alkyl, or R$^{2a}$ represents —C(O)R$^{13}$;

R$^{13}$ represents H or C$_{1-4}$ alkyl; and unless otherwise specified alkyl, alkylene, alkenylene, cycloalkylene, phenylene and naphthylene groups, as well as the alkyl part of alkoxy groups, may be substituted by one or more halo atoms;

or a pharmaceutically acceptable salt thereof, provided that the compound contains at least one Q$^a$ or Q$^b$ group that is other than a structural fragment represented by formula Ia in which G$^1$ represents CH.

2. A compound as claimed in claim 1, wherein
R$^1$ represents NO$_2$, —N(R$^{2a}$)R$^{2b}$ or H; and/or
R$^{1a}$ represents H or C$_{1-8}$ alkyl.

3. A compound as claimed in claim 1, wherein
a represents 1, 2 or 3; and/or
A represents C$_{2-6}$ alkylene.

4. A compound as claimed in claim 1, wherein
D represents Het$^1$ or —N(R$^{3a}$)R$^{3b}$;
Het$^1$ represents a five- to seven-membered heterocyclic group containing at least one N atom and optionally one or more heteroatoms selected from N, O and S, which heterocyclic groups are optionally substituted by one or more substituents selected from C$_{1-4}$ alkyl and C$_{1-4}$ alkoxy; and/or
R$^{3a}$ and R$^{3b}$ represent C$_{1-4}$ alkyl.

5. A compound as claimed in claim 1, wherein
Q$^a$ and Q$^b$ independently represent
naphthyl (optionally substituted by one or more substituents selected from halo, nitro, N(R$^{2a}$)R$^{2b}$, C$_{1-3}$ alkyl and C$_{1-3}$ alkoxy),
Het$^3$,
or a structural fragment represented by formula Ia, Id or If; and/or
Q$^c$ represents a structural fragment represented by formula Ia, Ib, Ic, Id or If.

6. A compound as claimed in claim 1, wherein
R$^4$ represents H;
R$^5$ represents C$_{1-6}$ alkyl; and/or
R$^8$ represents H or C$_{1-8}$ alkyl.

7. A compound as claimed in claim 1, wherein
R$^{10}$ represents, independently at each occurrence, OH, halo, nitro, N(R$^{2a}$)R$^{2b}$)R$^{2b}$, C$_{1-3}$ alkyl and C$_{1-3}$ alkoxy; and/or
b represents 0, 1 or 2.

8. A compound as claimed in claim 1, wherein
G$^1$ represents CH; and/or
G$^2$ represents CH or N.

9. A compound as claimed in claim 1, wherein
Het$^3$ represents a ten-membered, bicyclic heterocyclic group containing a N-atom and optionally containing one or more heteroatoms selected from N, O and S, which group is optionally substituted by one or more substituents selected from halo, nitro, N(R$^{2a}$)R$^{2b}$, Het$^a$, C$_{1-3}$ alkyl and OR$^a$;
R$^a$ represents C$_{1-2}$ alkyl or Het$^b$; and/or
Het$^a$ and Het$^b$ independently represent ten- or nine-membered heterocyclic groups containing one or more heteroatoms selected from N, O and S, which heterocyclic groups are optionally substituted by one or more substituents selected from halo, nitro, C$_{1-2}$ alkyl and C$_{1-2}$ alkoxy.

10. A compound as claimed in claim 1, wherein
R$^{11}$ and R$^{12}$ both represent H.

11. A compound as claimed in claim 1, wherein
R$^{2a}$ and R$^{2b}$ independently represent, at each occurrence when used herein, H or C$_{1-2}$ alkyl.

12. A compound as claimed in claim 1, wherein
one of Q$^a$ and Q$^b$ represents a structural fragment represented by formula If, and the other of Q$^a$ and Q$^b$ represents
naphthyl (optionally substituted by one or more substituents selected from OH, halo, cyano, nitro, N(R$^{2a}$)R$^{2b}$, C$_{1-4}$ alkyl and C$_{1-4}$ alkoxy),
Het$^3$,
or a structural fragment represented by formula Ia, Ib, Ic, Id, Ie or If, or Q$^a$ represents Het$^3$ and Q$^b$ represents
naphthyl (optionally substituted by one or more substituents selected from OH, halo, cyano, nitro, N(R$^{2a}$)R$^{2b}$, C$_{1-4}$ alkyl and C$_{1-4}$ alkoxy),
Het$^3$,
or a structural fragment represented by formula Ia, Ib, Ic, Id, Ie or If.

13. A compound as claimed in claim 12, wherein
Q$^a$ and Q$^b$ are attached trans-relative to each other;
R$^{11}$ and R$^{12}$ both represent H;
a represents 2; and/or
each Q$^c$ independently represents a structural fragment represented by formula Ia or Id.

14. A compound as claimed in claim 1 that is a compound of formula Ig

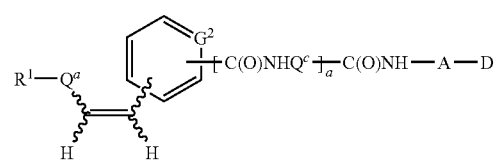

wherein
the wavy lines indicate optional cis- or trans-stereochemistry;
R$^1$ represents NO$_2$, —N(R$^{2a}$)R$^{2b}$ or H;
a represents 1 or 2;
Q$^a$ represents naphthyl (optionally substituted by one or more substituents selected from OH, halo, cyano, nitro, N(R$^{2a}$)R$^{2b}$, C$_{1-4}$ alkyl and C$_{1-4}$ alkoxy), Het$^3$ or a structural fragment represented by formula If;
G$^2$ represents CH or N; and
R$^{2a}$, R$^{2b}$, Het$^3$, Q$^c$, A and D are as defined in claim 1.

15. A compound as claimed in claim 1, wherein the compound is:
(i) 4-({[4-({4-[(E)-2-(3-methoxyphenyl)ethenyl]benzoyl}amino)-1-methyl-1H-pyrrol-2-yl]carbonyl}amino)-1-methyl-N-[2-(4-morpholinyl)ethyl]-1H-pyrrole-2-carboxamide;
(ii) 1-methyl-4-({[1-methyl-4-({4-[(E)-2-(3-quinolinyl)ethenyl]benzoyl}amino)-1H-pyrrol-2-yl]carbonyl}amino)-N-[2-(4-morpholinyl)ethyl]-1H-pyrrole-2-carboxamide;
(iii) 1-methyl-N-[1-methyl-5-({[2-(4-morpholinyl)ethyl]amino}carbonyl)-1H-pyrrol-3-yl]-4-({4-[(E)-2-(1-methyl-1H-pyrrol-2-yl)ethenyl]benzoyl}amino)-1H-pyrrole-2-carboxamide
(iv) N-[5-({[3-(dimethylamino)propyl]amino}carbonyl)-1-methyl-1H-pyrrol-3-yl]-4-({4-[(E)-2-(3-methoxyphenyl)ethenyl]benzoyl}amino)-1-methyl-1H-pyrrole-2-carboxamide;
(v) N-[5-({[3-(dimethylamino)propyl]amino}carbonyl)-1-methyl-1H-pyrrol-3-yl]-1-methyl-4-({4-[(E)-2-(3-quinolinyl)ethenyl]benzoyl}amino)-1H-pyrrole-2-carboxamide;
(vi) N-[5-({[3-(dimethylamino)propyl]amino}carbonyl)-1-methyl-1H-pyrrol-3-yl]-4-({3-[(E)-2-(3-methoxyphenyl)ethenyl]benzoyl}amino)-1-methyl-1H-pyrrole-2-carboxamide;
(vii) N-[5-({[3-(dimethylamino)propyl]amino}carbonyl)-1-methyl-1H-pyrrol-3-yl]-1-methyl-4-({4-[(E)-2-(4-pyridinyl)ethenyl]benzoyl}amino)-1H-pyrrole-2-carboxamide;
(viii) N-[5-({[5-({[3-(dimethylamino)propyl]amino}carbonyl)-1-methyl-1H-pyrrol-3-yl]amino}carbonyl)-1-methyl-1H-pyrrol-3-yl]-1-methyl-4-[(E)-2-(4-nitrophenyl)ethenyl]-1H-pyrrole-2-carboxamide;
(ix) N-[3-(dimethylamino)propyl]-5-isopentyl-2-({[1-methyl-4-({4-[(E)-2-(3-quinolinyl)ethenyl]benzoyl}amino)-1H-pyrrol-2-yl]carbonyl}amino)-1,3-thiazole-4-carboxamide;
(x) 1-methyl-N-[1-methyl-5-({[1-methyl-5-({[2-(4-morpholinyl)ethyl]amino}-carbonyl)-1H-pyrrol-3-yl]amino}carbonyl)-1H-pyrrol-3-yl]-4-[(E)-2-(3-quinolinyl)ethenyl]-1H-pyrrole-2-carboxamide;
(xi) 1-methyl-N-[1-methyl-5-({[2-(4-morpholinyl)ethyl]amino}carbonyl)-1H-pyrrol-3-yl]-4-[({1-methyl-4-[(E)-2-(2-quinolinyl)ethenyl]-1H-pyrrol-2-yl}carbonyl)amino]-1H-pyrrole-2-carboxamide;
(xii) N-[1-methyl-5-({[1-methyl-5-({[2-(4-morpholinyl)ethyl]amino}carbonyl)-1H-pyrrol-3-yl]amino}carbonyl)-1H-pyrrol-3-yl]-2-[(E)-2-(2-quinolinyl)ethenyl]-1,3-thiazole-4-carboxamide;
(xiii) 1-methyl-N-[1-methyl-5-({[2-(4-morpholinyl)ethyl]amino}carbonyl)-1H-pyrrol-3-yl]-4-({4-[(E)-2-(2-naphthyl)ethenyl]benzoyl}amino)-1H-pyrrole-2-carboxamide;
(xiv) 4-[(4-{(E)-2-[2-(1H-1,2,3-benzotriazol-1-yloxy)-3-quinolinyl]ethenyl}-benzoyl)amino]-1-methyl-N-[1-methyl-5-({[2-(4-morpholinyl)ethyl]amino}-carbonyl)-1H-pyrrol-3-yl]-1H-pyrrole-2-carboxamide;
(xv) 1-methyl-N-[1-methyl-5-({[2-(4-morpholinyl)ethyl]amino}carbonyl)-1H-pyrrol-3-yl]-4-({4[(E)-2-(2-quinolinyl)ethenyl]benzoyl}amino)-1H-pyrrole-2-carboxamide;
(xvi) 5-Isopentyl-2-({[1-methyl-4-({4-[(E)-2-(3-quinolinyl)ethenyl]benzoyl}-amino)-1H-pyrrol-2-yl]carbonyl}amino)-N-[2-(4-morpholinyl)ethyl]-1,3-thiazole-4-carboxamide;
(xvii) 2-({[4-({4-[(E)-2-(2-chloro-3-quinolinyl)ethenyl]benzoyl}amino)-1-methyl-1H-pyrrol-2-yl]carbonyl}amino)-5-isopentyl-N-[2-(4-morpholinyl)ethyl]-1,3-thiazole-4-carboxamide;
(xviii) 2-[({4-[(4-{(E)-2-[2-(1H-1,2,3-benzotriazol-1-yloxy)-3-quinolinyl]-ethenyl}benzoyl)amino]-1-methyl-1H-pyrrol-2-yl}carbonyl)amino]-5-isopentyl-N-[2-(4-morpholinyl)ethyl]-1,3-thiazole-4-carboxamide;
(xix) 5-isopentyl-2-({[1-methyl-4-({4-[(E)-2-(2-quinolinyl)ethenyl]benzoyl}-amino)-1H-pyrrol-2-yl]carbonyl}amino)-N-[2-(4-morpholinyl)ethyl]-1,3-thiazole-4-carboxamide;
(xx) 5-isopentyl-2-({[1-methyl-4({4-[(E)-2-(2-naphthyl)ethenyl]benzoyl}amino)-1H-pyrrol-2-yl]carbonyl}amino)-N-[2-(4-morpholinyl)ethyl]-1,3-thiazole-4-carboxamide;
(xxi) 5-isopentyl-2-[({1-methyl-4-[({1-methyl-4-[(E)-2-(4-nitrophenyl)ethenyl]-1H-pyrrol-2-yl}carbonyl)amino]-1H-pyrrol-2-yl}carbonyl)amino]-N-[2-(4-morpholinyl)ethyl]-1,3-thiazole-4-carboxamide;
(xxii) 6-[(E)-2-(4-methoxyphenyl)ethenyl]-N-[1-methyl-5-({[1-methyl-5-({[2-(4-morpholinyl)ethyl]amino}carbonyl)-1H-pyrrol-3-yl]amino}carbonyl)-1H-pyrrol-3-yl]nicotinamide;
(xxiii) 2-[(E)-2-(4-methoxyphenyl)ethenyl]-N-[1-methyl-5-({[1-methyl-5-({[2-(4-morpholinyl)ethyl]amino}carbonyl)-1H-pyrrol-3-yl]amino}carbonyl)-1H-pyrrol-3-yl]-6-quinolinecarboxamide;
(xxiv) N-[1-methyl-5-({[1-methyl-5-({[2-(4-morpholinyl)ethyl]amino}carbonyl)-1H-pyrrol-3-yl]amino}carbonyl)-1H-pyrrol-3-yl]-2-{(E)-2-[4-(methylsulfanyl)-phenyl]ethenyl}-6-quinolinecarboxamide;
(xxv) N-[1-methyl-5-({[1-methyl-5-({[2-(4-morpholinyl)ethyl]amino}carbonyl)-1H-pyrrol-3-yl]amino}carbonyl)-1H-pyrrol-3-yl]-6-{(E)-2-[4-(methylsulfanyl)-phenyl]ethenyl}nicotinamide,
or a pharmaceutically acceptable salt thereof.

16. A compound as claimed in claim 1, wherein the compound is 4-({[4-({4-[(E)-2-(3-methoxyphenyl)ethenyl]benzoyl}amino)-1-methyl-1H-pyrrol-2-yl]carbonyl}amino)-1-methyl-N-[2-(4-morpholinyl)ethyl]-1H-pyrrole-2-carboxamide.

17. A compound as claimed in claim 1, wherein the compound is 1-methyl-4-({[1-methyl-4-({4-[(E)-2-(3-quinolinyl)ethenyl]benzoyl}amino)-1H-pyrrol-2-yl]carbonyl}amino)-N-[2-(4-morpholinyl)ethyl]-1H-pyrrole-2-carboxamide.

18. A compound as claimed in claim 1, wherein the compound is 6-[(E)-2-(4-methoxyphenyl)ethenyl]-N-[1-methyl-5-({[1-methyl-5-({[2-(4-morpholinyl)ethyl]amino}carbonyl)-1H-pyrrol-3-yl]amino}carbonyl)-1H-pyrrol-3-yl]nicotinamide.

19. A pharmaceutical formulation including a compound as defined in claim 1 in admixture with a pharmaceutically-acceptable adjuvant, diluent or carrier.

20. A method of treatment of a bacterial or fungal infection, which method comprises administration of a therapeutically effective amount of a compound as defined in claim 1 to a person suffering from the bacterial or fungal infection.

21. A method of treating a bacterial or fungal infection, where the bacterial or fungal infection is resistant to one or more anti-bacterial or anti-fungal agents, which method comprises administration of a therapeutically effective amount of a compound as defined in claim 1 to a person having the infection, wherein:
the one or more anti-bacterial agents are members selected from the group consisting of natural and synthetic penicillins and cephalosporins, sulphonamides, erythromycin, kanomycin, tetracycline, chloramphenicol, rifampicin, gentamicin, ampicillin, benzypenicillin, benethamine penicillin, benzathine penicillin, phenethicillin, phenoxy-methyl penicillin, procaine penicillin, cloxacillin, flucloxacillin, methicillin sodium, amoxicillin, bacampicillin hydrochloride, ciclacillin, mezlocillin, pivampicillin, talampicillin hydrochloride, carfecillin sodium, piperacillin, ticarcillin, mecillinam, pirmecillinan, cefaclor, cefadroxil, cefotaxime, cefoxitin, cefsulodin sodium, ceftazidime, ceftizoxime, cefuroxime, cephalexin, cephalothin, cephamandole, cephazolin, cephradine, latamoxef disodium, aztreonam, chlortetracycline hydrochloride, clomocycline sodium, demeclocydine hydrochloride, doxycycline, lymecycline, minocycline, oxytetracycline, amikacin, framycetin sulphate, neomycin sulphate, netilmicin, tobramycin, colistin, sodium fusidate, polymyxin B sulphate, spectinomycin, vancomycin, calcium sulphaloxate, sulfametopyrazine sulphadiazine, sulphadimidine, sulphaguanidine, sulphaurea, capreomycin, metronidazole, tinidazole, cinoxacin, ciprofloxacin, nitrofurantoin, hexamine, streptomycin, carbenicillin, colistimethate, polymyxin B, furazolidone, nalidixic acid, trimethoprim-sulfamethoxazole, clindamycin, lincomycin, cycloserine, isoniazid, ethambutol, ethionamide and pyrazinamide; and the one or more anti-fungal agents are members selected from the group consisting of miconazole, ketoconazole, itraconazole, fluconazole, fusidic acid, amphotericin, flucytosine, griseofulvin, natamycin and nystatin.

22. A method of treatment of a bacterial or fungal infection, which method comprises administration, to a person suffering from the bacterial or fungal infection, of a therapeutically effective amount of a compound as defined in claim 1 in combination with one or more other compounds, wherein the other compounds are known to be effective in treating the bacterial or fungal infection, and wherein the one or more other compounds are:

anti-bacterial agents selected from the group consisting of natural and synthetic penicillins and cephalosporins, sulphonamides, erythromycin, kanomycin, tetracycline, chloramphenicol, rifampicin, gentamicin, ampicillin, benzypenicillin, benethamine penicillin, benzathine penicillin, phenethicillin, phenoxy-methyl penicillin, procaine penicillin, cloxacillin, flucloxacillin, methicillin sodium, amoxicillin, bacampicillin hydrochloride, ciclacillin, mezlocillin, pivampicillin, talampicillin hydrochloride, carfecillin sodium, piperacillin, ticarcillin, mecillinam, pirmecillinan, cefaclor, cefadroxil, cefotaxime, cefoxitin, cefsulodin sodium, ceftazidime, ceftizoxime, cefuroxime, cephalexin, cephalothin, cephamandole, cephazolin, cephradine, latamoxef disodium, aztreonam, chlortetracycline hydrochloride, clomocycline sodium, demeclocydine hydrochloride, doxycycline, lymecycline, minocycline, oxytetracycline, amikacin, framycetin sulphate, neomycin sulphate, netilmicin, tobramycin, colistin, sodium fusidate, polymyxin B sulphate, spectinomycin, vancomycin, calcium sulphaloxate, sulfametopyrazine, sulphadiazine, sulphadimidine, sulphaguanidine, sulphaurea, capreomycin, metronidazole, tinidazole, cinoxacin, ciprofloxacin, nitrofurantoin, hexamine, streptomycin, carbenicillin, colistimethate, polymyxin B, furazolidone, nalidixic acid, trimethoprim-sulfamethoxazole, clindamycin, lincomycin, cycloserine, isoniazid, ethambutol, ethionamide and pyrazinamide; or anti-fungal agents selected from the group consisting of miconazole, ketoconazole, itraconazole, fluconazole, fusidic acid, amphotericin, flucytosine, griseofulvin, natamycin and nystatin.

23. A combination product comprising components:
(A) a formulation comprising a compound as defined in claim 1; and
(B) a formulation comprising one or more other compounds, wherein the other compounds are known to be effective in treating a bacterial or fungal infection, and wherein the one or more other compounds are:

anti-bacterial agents selected from the group consisting of natural and synthetic penicillins and cephalosporins, sulphonamides, erythromycin, kanomycin, tetracycline, chloramphenicol, rifampicin, gentamicin, ampicillin, benzypenicillin, benethamine penicillin, benzathine penicillin, phenethicillin, phenoxy-methyl penicillin, procaine penicillin, cloxacillin, flucloxacillin, methicillin sodium, amoxicillin, bacampicillin hydrochloride, ciclacillin, mezlocillin, pivampicillin, talampicillin hydrochloride, carfecillin sodium, piperacillin, ticarcillin, mecillinam, pirmecillinan, cefaclor, cefadroxil, cefotaxime, cefoxitin, cefsulodin sodium, ceftazidime, ceftizoxime, cefuroxime, cephalexin, cephalothin, cephamandole, cephazolin, cephradine, latamoxef disodium, aztreonam, chlortetracycline hydrochloride, clomocycline sodium, demeclocydine hydrochloride, doxycycline, lymecycline, minocycline, oxytetracycline, amikacin, framycetin sulphate, neomycin sulphate, netilmicin, tobramycin, colistin, sodium fusidate, polymyxin B sulphate, spectinomycin, vancomycin, calcium sulphaloxate, sulfametopyrazine, sulphadiazine, sulphadimidine, sulphaguanidine, sulphaurea, capreomycin, metronidazole, tinidazole, cinoxacin, ciprofloxacin, nitrofurantoin, hexamine, streptomycin, carbenicillin, colistimethate, polymyxin B, furazolidone, nalidixic acid, trimethoprim-sulfamethoxazole, clindamycin, lincomycin, cycloserine, isoniazid, ethambutol, ethionamide and pyrazinamide; or anti-fungal agents selected from the group consisting of miconazole, ketoconazole, itraconazole, fluconazole, fusidic acid, amphotericin, flucytosine, griseofulvin, natamycin and nystatin.

24. A combination product as claimed in claim 23, wherein each of components (A) and (B) is formulated in admixture with a pharmaceutically-acceptable adjuvant, diluent or carrier.

25. A combination product as claimed in claim 23, wherein (A) and (B) are presented as separate components.

26. A combination product as claimed in claim 23, wherein (A) and (B) are presented as a single formulation.

27. A method of inhibiting DNA replication, which method comprises contacting the DNA with an inhibitory amount of a compound as defined in claim 1.

28. A method of detecting dsDNA in a sample, said method comprising contacting a compound as defined in claim 1 with the sample and comparing the fluorescence of said compound in contact with said sample with the fluorescence of said compound in isolation, a change in fluorescence indicating the presence of DNA in the sample.

29. A process for the preparation of compounds of formula I as defined in claim 1 which comprises:
(a) reaction of a compound of formula III,

III wherein $Q^c$, D and A are as defined in claim 1 and c is as defined below, with a compound of formula IV,

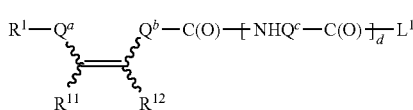

IV wherein $L^1$ represents a leaving group, c and d are both integers from 0 to 4, wherein the sum of c and d is from 1 to 4 and $R^1$, $R^{11}$, $R^{12}$ and $Q^a$ to $Q^c$ are as defined in claim 1;

(b) reaction of a compound of formula Va,

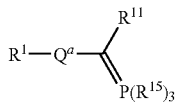

Va wherein $R^{15}$ represents aryl (which latter group is optionally substituted by one or more substituents selected from halo, cyano, nitro, $C_{1-4}$ alkyl and $C_{1-4}$ alkoxy) or $C_{1-6}$ alkyl), and $R^1$, $R^{11}$, $Q^a$ and aryl are as defined in claim 1 with a compound of formula VI

VI wherein A, a, D, $R^{12}$ $Q^b$, and $Q^c$ are as defined in claim 1;
(c) reaction of a compound of formula Vb,

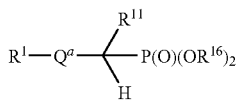

Vb wherein $R^{16}$ represents $C_{1-6}$ alkyl, and $R^1$, $R^{11}$ and $Q^a$ are as defined in claim 1 with a suitable base, followed by reaction with a compound of formula VI as defined above;

(d) reaction of a compound of formula VIIa,

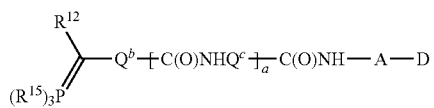

VIIa wherein $R^{12}$, $Q^b$, $Q^c$, a, A and D are as defined in claim 1 and $R^{15}$ is as defined above, with a compound of formula VIII,

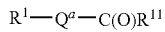

VIII wherein $R^1$, $R^{11}$ and $Q^a$ are as defined in claim 1; or
(e) reaction of a compound of formula VIIb,

VIIb wherein $R^{12}$, $Q^b$, $Q^c$, a, A and D are as defined in claim 1 and $R^{16}$ is as defined in (c) above, with a suitable base, followed by reaction with a compound of formula VIII as defined above.

* * * * *